US012630616B2

(12) United States Patent
Hardy et al.

(10) Patent No.: US 12,630,616 B2
(45) Date of Patent: May 19, 2026

(54) COMPLEMENT C2 BINDING PROTEINS AND USES THEREOF

(71) Applicant: CSL Innovation Pty Ltd, Melbourne (AU)

(72) Inventors: Matthew Hardy, Doreen (AU); Con Panousis, Bundoora (AU); Rodrigo Morales, Port Melbourne (AU)

(73) Assignee: CSL Innovation Pty Ltd, Melbourne (AU)

( * ) Notice: Subject to any disclaimer, the term of this patent is extended or adjusted under 35 U.S.C. 154(b) by 1083 days.

(21) Appl. No.: 17/634,606

(22) PCT Filed: Aug. 12, 2020

(86) PCT No.: PCT/AU2020/050841
§ 371 (c)(1),
(2) Date: Feb. 11, 2022

(87) PCT Pub. No.: WO2021/026609
PCT Pub. Date: Feb. 18, 2021

(65) Prior Publication Data
US 2022/0332804 A1      Oct. 20, 2022

(30) Foreign Application Priority Data

Aug. 12, 2019    (AU) ................................ 2019902900

(51) Int. Cl.
*C07K 16/18*        (2006.01)
*A61K 39/00*        (2006.01)

(52) U.S. Cl.
CPC ........ *C07K 16/18* (2013.01); *A61K 2039/505* (2013.01); *C07K 2317/33* (2013.01); *C07K 2317/524* (2013.01); *C07K 2317/526* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,196,265 A | 4/1980 | Koprowski et al. | |
| 4,676,980 A | 6/1987 | Segal et al. | |
| 4,816,567 A | 3/1989 | Cabilly et al. | |
| 5,225,539 A | 7/1993 | Winter | |
| 5,252,714 A | 10/1993 | Harris et al. | |
| 5,530,101 A | 6/1996 | Queen et al. | |
| 5,565,332 A | 10/1996 | Hoogenboom et al. | |
| 5,585,089 A | 12/1996 | Queen et al. | |
| 5,731,168 A | 3/1998 | Carter et al. | |
| 5,807,715 A | 9/1998 | Morrison et al. | |
| 5,885,793 A | 3/1999 | Griffiths et al. | |

| | | | |
|---|---|---|---|
| 6,180,370 B1 * | 1/2001 | Queen ..................... | A61P 19/02 |
| | | | 435/69.6 |
| 6,248,516 B1 | 6/2001 | Winter et al. | |
| 6,300,064 B1 | 10/2001 | Knappik et al. | |
| 7,083,784 B2 | 8/2006 | Dall'Acqua et al. | |
| 7,927,592 B2 * | 4/2011 | Fung ....................... | A61P 37/08 |
| | | | 424/130.1 |
| 2006/0263367 A1 | 11/2006 | Fey et al. | |
| 2007/0135620 A1 | 6/2007 | Chamberlain et al. | |
| 2011/0111406 A1 | 5/2011 | Igawa et al. | |
| 2016/0244526 A1 | 8/2016 | Igawa et al. | |

FOREIGN PATENT DOCUMENTS

| | | | | |
|---|---|---|---|---|
| EP | 0154316 B1 | 9/1989 | | |
| EP | 0569141 A2 | 11/1993 | | |
| EP | 0401384 B1 | 3/1996 | | |
| WO | 9216221 A1 | 10/1992 | | |
| WO | 9404678 A1 | 3/1994 | | |
| WO | 9407921 A1 | 4/1994 | | |
| WO | 9534326 A1 | 12/1995 | | |
| WO | 9749805 A2 | 12/1997 | | |
| WO | 9844001 A1 | 10/1998 | | |
| WO | 9945132 A1 | 9/1999 | | |
| WO | 9957134 A1 | 11/1999 | | |
| WO | 200034317 A2 | 6/2000 | | |
| WO | WO-0151512 A2 * | 7/2001 | ....... | C07K 14/43559 |
| WO | 2001070818 A1 | 9/2001 | | |
| WO | 2001051512 A3 | 3/2002 | | |
| WO | 2002066630 A1 | 8/2002 | | |
| WO | 2002080967 A1 | 10/2002 | | |
| WO | 2004064724 A2 | 8/2004 | | |
| WO | 2004108158 A1 | 12/2004 | | |
| WO | 2005118629 A1 | 12/2005 | | |
| WO | 2006033386 A1 | 3/2006 | | |

(Continued)

OTHER PUBLICATIONS

Yoshida, Yoko et al. "Pathogenesis of Atypical Hemolytic Uremic Syndrome." Journal of atherosclerosis and thrombosis vol. 26,2 (2019): 99-110. doi: 10.5551/jat.RV17026 (Year: 2019).*

Ayehu G, Atari M, Hassanein M, et al. C3 Glomerulopathy. [Updated Nov. 5, 2024]. In: StatPearls [Internet]. Treasure Island (FL): StatPearls Publishing; Jan. 2025 (Year: 2025).*

Maillard, Nicolas et al. "Current Understanding of the Role of Complement in IgA Nephropathy." Journal of the American Society of Nephrology : JASN vol. 26,7 (2015): 1503-12. doi: 10.1681/ASN.2014101000 (Year: 2015).*

Harboe, Morten, and Tom Eirik Mollnes. "The alternative complement pathway revisited." Journal of cellular and molecular medicine vol. 12,4 (2008): 1074-84. doi:10.1111/j.1582-4934.2008.00350.x (Year: 2008).*

(Continued)

*Primary Examiner* — Michael Szperka
*Assistant Examiner* — Lia E Taylor
(74) *Attorney, Agent, or Firm* — McNeill PLLC

(57) ABSTRACT

The present disclosure relates to proteins comprising antigen binding sites that bind to human complement C2 (C2). The present disclosure also relates to methods of inhibiting complement activity in a subject as well as methods of treating or preventing complement-mediated disorders.

18 Claims, 7 Drawing Sheets

Specification includes a Sequence Listing.

(56)                  References Cited

FOREIGN PATENT DOCUMENTS

| WO | 2010080538 A1 | 7/2010 |
| WO | 2011051489 A2 | 5/2011 |
| WO | 2011103076 A1 | 8/2011 |
| WO | 2012044831 A1 | 4/2012 |
| WO | 2012112188 A1 | 8/2012 |
| WO | 2013075066 A2 | 5/2013 |
| WO | 2014072481 A1 | 5/2014 |
| WO | 2014179657 A1 | 11/2014 |
| WO | 2014189378 A1 | 11/2014 |
| WO | 2015063611 A4 | 12/2015 |
| WO | 2017132259 A1 | 8/2017 |

OTHER PUBLICATIONS

Janeway, Charles A. "Immunobiology: The Immune System in Health and Disease." 2001 (Year: 2001).*

Kipriyanov, Sergey M., and Fabrice Le Gall. "Generation and production of engineered antibodies." Molecular biotechnology 26.1 ( 2004): 39-60. (Year: 2004).*

Bonvin, Pauline et al., "De novo isolation of antibodies with pH-dependent binding properties", mAbs 2015, 7(2): 294-302.

Igawa, Tomoyuki et al., "Sweeping antibody as a novel therapeutic antibody modality capable of eliminating soluble antigens from circulation", Immunological Reviews 2016, 270: 132-151.

Al-Lazikani et al., "Standard Conformations for the Canonical Structures of Immunoglobulins", J. Mol. Biol. (1997) 273: 927-948.

Armour et al., "Recombinant human IgG molecules lacking Fcγ receptor I binding and monocyte triggering activities", Eur. J. Immunol. 1999. 29: 2613-2624.

Bork et al., "Structural Classification, Sequence Patterns and Common Core", J. Mol. Biol. (1994) 242: 309-320.

Boswell et al., "Effects of Charge on Antibody Tissue Distribution and Pharmacokinetics", Bioconjugate Chem. 2010, 21: 2153-2163.

Chia et al., "Half-life—extended recombinant coagulation factor IX-albumin fusion protein is recycled via the FcRn-mediated pathway", J. Biol. Chem. (2018) 293(17): 6363-6373.

Chothia et al., "Canonical Structures for the Hypervariable Regions of Immunoglobulins", J. Mol. Biol. (1987) 196: 901-917.

Chothia et al., "Conformations of immunoglobulin hypervariable regions", Nature, Dec. 28, 1989, 342(21): 877-883.

Chowdhury, Partha S., "Engineering Hot Spots for Affinity Enhancement of Antibodies", Methods in Molecular Biology, 2008, 207: 179-196.

Cunningham et al., "High-Resolution Epitope Mapping of hGH-Receptor Interactions by Alanine-Scanning Mutagenesis", Science Reports, 1989, 244: 1081-1085.

Dall'Acqua et al., "Modulation of the Effector Functions of a Human IgG1 through Engineering of Its Hinge Region", J Immunol 2006; 177:1129-1138.

Edelman et al., "The Covalent Structure of an Entire γG Immunoglobulin Molecule", Biochemistry, 1969, 63: 78-85.

Francis, Gillian E., "Protein modification and fusion proteins", Focus on Growth Factors, 3(2): 4-10 (1992).

Hezareh et al., "Effector Function Activities of a Panel of Mutants of a Broadly Neutralizing Antibody against Human Immunodeficiency Virus Type 1", J. Virol. 2001, 75(24): 12161-12168.

Honegger et al., "Yet Another Numbering Scheme for Immunoglobulin Variable Domains: An Automatic Modeling and Analysis Tool", J. Mol. Biol. (2001) 309: 657-670.

Hoogenboom, Hennie R., "Overview of Antibody Phage-Display Technology and Its Applications", Methods in Molecular Biology, 2001, 178: 1-37.

Horiuchi et al., "Site-directed mutagenesis of the region around Cys-241 of complement component C2. Evidence for a C4b binding site.", The Journal of Immunology, 1991; 147: 584-589.

International Preliminary Report on Patentability from PCT/AU2020/050841, mailed Nov. 29, 2021, 16 pages.

International Search Report and Written Opinion of PCT/AU2020/050841 mailed Sep. 23, 2020, 14 pages.

Kim et al., "Identifying amino acid residues that influence plasma clearance of murine IgG1 fragments by site-directed mutagenesis", Eur. J. Immunol. 1994. 24: 542-548.

Kim et al., "Localization of the site of the murine IgG1 molecule that is involved in binding to the murine intestinal Fc receptor", Eur. J. Immunol. 1994. 24: 2429-2434.

Krishnan et al., "The Crystal Structure of C2a, the Catalytic Fragment of Classical Pathway C3 and C5 Convertase of Human Complement", J. Mol. Biol. (2007) 367: 224-233.

Largaespada et al., "The ABL-MYC retrovirus generates antigen-specific plasmacytomas by in vitro infection of activated B lymphocytes from spleen and other murine lymphoid organs", Journal of Immunological Methods (1996) 197: 85-95.

Le Lamer et al., "Translation of TRO40303 from myocardial infarction models to demonstration of safety and tolerance In a randomized Phase 1 trial", Journal of Translational Medicine, 2014, 12:38 (15 pages).

Lefranc et al., "IMGT unique numbering for immunoglobulin and T cell receptor variable domains and Ig superfamily V-like domains", Developmental and Comparative Immunology (2003) 27: 55-77.

Mackness et al., "Antibody Fc engineering for enhanced neonatal Fc receptor binding and prolonged circulation half-life", mAbs, 11(7): 1276-1288, 2019.

Malik et al., "Polyethylene Glycol (PEG)-modified Granulocyte-Macrophage Colony-stimulating Factor (GM-CSF) with Conserved Biological Activity", Experimental Hematology, 20: 1028-1035 (1992).

Milder et al., "Structure of Complement Component C2a: Implications for Convertase Formation and Substrate Binding", Structure, 14: 1587-1597, Oct. 2006.

Mortensen et al., "Solution Structures of Complement C2 and Its C4 Complexes Propose Pathway-specific Mechanisms for Control and Activation of the Complement Proconvertases", The Journal of Biological Chemistry, 291 (32): 16494-16507, Aug. 5, 2016.

Murtaugh et al., "A Combinatorial Histidine Scanning Library Approach to Engineer Highly pH-Dependent Protein Switches", Protein Science 2011, 20: 1619-1631.

Reis et al., "Applying complement therapeutics to rare diseases", Clinical Immunology, (2015) 161: 225-240.

Schindelin et al., "Fiji: an open-source platform for biological-image analysis", Nature Methods, Jul. 2012, 9 (7):676-682.

Shields et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry, Mar. 2, 2001, 276 (9): 6591-6604.

Written Opinion of the International Preliminary Examining Authority from PCT/AU2020/050841 mailed Jan. 19, 2021, 7 pages.

* cited by examiner pH 7.4

- RF16-191 huC2 pH7.4
- RF16-203 huC2 pH7.4
- RF16-214 huC2 pH7.4
- RF16-226 huC2 pH7.4
- RF16-242 huC2 pH7.4
- RF16-207 huC2 pH7.4
- RF16-240 huC2 pH7.4
- chBM4-huG1k pH7.4 ug/ml anti-C2 mab pH 5.5

- RF16-191 huC2 pH5.5
- RF16-203 huC2 pH5.5
- RF16-214 huC2 pH5.5
- RF16-226 huC2 pH5.5
- RF16-242 huC2 pH5.5
- RF16-207 huC2 pH5.5
- RF16-240 huC2 pH5.5
- chBM4-huG1k pH5.5 ug/ml anti-C2 mab

A

B

COMPLEMENT C2 BINDING PROTEINS AND USES THEREOF

RELATED APPLICATION DATA

This application is a national phase entry pursuant to 35 U.S.C. § 371 of International Application No. PCT/AU2020/050841, filed Aug. 12, 2020, which claims priority from Australian Patent Application No 2019902900 filed on Aug. 12, 2019, entitled "Complement C2 binding proteins and uses thereof". These applications are hereby incorporated by reference in their entireties.

SEQUENCE LISTING

The present application is filed together with a Sequence Listing in electronic form. The entire contents of the Sequence Listing are hereby incorporated by reference.

FIELD

The present disclosure relates to proteins that bind to complement C2 (C2) and uses thereof, e.g., in therapies for treating or preventing complement-mediated disorders.

BACKGROUND

The complement system is a vital component of the humoral response against invading pathogens. However, over-activation of complement is associated with pathology, e.g. in antibody-mediated transplant rejection, fibrosis and chronic autoimmune conditions. Complement C2 (C2), also known as complement component 2 is an early activator of the complement system. C2 (732 amino acids, ~100 kDa) is produced in the liver as an inactive zymogen consisting of five domains: three N-terminal complement-control-proteins ("CCP", amino acids 13-223), a von Willebrand factor A-type (VWA) domain, and a C-terminal trypsin-like serine proteinase (SP) domain. C2 becomes rapidly activated by complement component C4b, which in itself is activated following antibody deposition (classical pathway) or carbohydrate recognition (lectin pathway) at the pathogen or cellular surface. The C4bC2 complex is cleaved by C1s or MASP2 into C2a and C2b. C2a is the larger, enzymatically active fragment which is incorporated into the C3 convertase. The smaller fragment, C2b is released into the fluid phase.

Targeting C2 offers an opportunity to regulate the classical and lectin complement pathways without significantly impacting the alternative complement pathway. Thus, there is a need for agents that can inhibit C2 and/or reduce the amount of C2 in circulation in order to, for example, treat or prevent a complement-mediated disorder.

SUMMARY

The present inventors have produced a class of proteins comprising antigen binding sites (e.g., Fabs and antibodies) that bind to human complement C2 (C2). These proteins bind to C2 with a higher affinity at neutral pH (i.e., approximately 7.3) relative to early endosomal pH (i.e., approximately 6.0). The inventors consider that this permits the proteins to bind to C2 in circulation, while releasing the C2 within the endosome for degradation, prior to recycling of the C2-binding protein.

The present disclosure therefore provides a protein comprising an antigen binding site which binds to C2 with greater affinity at a neutral pH than at an acidic pH. In some examples, the neutral pH is a pH in the range of 7.0 to 7.5. In some examples, the acidic pH is a pH in the range of 5.5 to 6.0.

The present disclosure also provides a protein comprising an antigen binding site which binds to C2 with greater affinity at pH 7.3 than at pH 6.0. Without wishing to be bound by theory, such proteins can bind to C2 at neutral pH, but then have an increased propensity to dissociate from C2 once internalized into the acidic early endosome (approximately pH 6.0). This pH-dependent binding to C2 allows binding of the protein to C2 in circulation, followed by internalization of the protein-C2 complex, dissociation of C2 in the endosome and trafficking of C2 to the lysosome for degradation, and recycling of the protein back to the cell surface via the neonatal Fc receptor (FcRn), thereby reducing the concentration of C2 in circulation. These proteins may be referred to as "sweeping" or "sweeper" proteins, or as "recycling" proteins.

In some examples, the protein binds to the same epitope in C2 as that bound by:

(i) RF16-226G (comprising a heavy chain variable region ($V_H$) comprising a sequence set forth in SEQ ID NO: 2 and a light chain variable region ($V_L$) comprising a sequence set forth in SEQ ID NO: 6);

(ii) RF16-214G (comprising a $V_H$ comprising a sequence set forth in SEQ ID NO: 3 and a $V_L$ comprising a sequence set forth in SEQ ID NO: 7);

(iii) RF16-242G (comprising a $V_H$ comprising a sequence set forth in SEQ ID NO: 4 and a $V_L$ comprising a sequence set forth in SEQ ID NO: 81);

(iv) RF16-226 (comprising a $V_H$ comprising a sequence set forth in SEQ ID NO: 2 and a $V_L$ comprising a sequence set forth in SEQ ID NO: 9);

(v) RF16-214 (comprising a $V_H$ comprising a sequence set forth in SEQ ID NO: 3 and a $V_L$ comprising a sequence set forth in SEQ ID NO: 10);

(vi) RF16-242 (comprising a $V_H$ comprising a sequence set forth in SEQ ID NO: 5 and a $V_L$ comprising a sequence set forth in SEQ ID NO: 11);

(vii) RF16-191 (comprising a $V_H$ comprising a sequence set forth in SEQ ID NO: 46 and a $V_L$ comprising a sequence set forth in SEQ ID NO: 50); or (viii) RF16-203 (comprising a $V_H$ comprising a sequence set forth in SEQ ID NO: 47 and a $V_L$ comprising a sequence set forth in SEQ ID NO: 51).

In some examples, the protein binds to the same epitope in C2 as that bound by:

(i) RF16-226G (comprising a heavy chain variable region ($V_H$) comprising a sequence set forth in SEQ ID NO: 2 and a light chain variable region ($V_L$) comprising a sequence set forth in SEQ ID NO: 6);

(ii) RF16-214G (comprising a $V_H$ comprising a sequence set forth in SEQ ID NO: 3 and a $V_L$ comprising a sequence set forth in SEQ ID NO: 7); or (iii) RF16-242G (comprising a $V_H$ comprising a sequence set forth in SEQ ID NO: 4 and a $V_L$ comprising a sequence set forth in SEQ ID NO: 8).

In some examples, the protein binds to an epitope in C2 that overlaps with the epitope bound by:

(i) RF16-226G (comprising a heavy chain variable region ($V_H$) comprising a sequence set forth in SEQ ID NO: 2 and a light chain variable region ($V_L$) comprising a sequence set forth in SEQ ID NO: 6);

(ii) RF16-214G (comprising a $V_H$ comprising a sequence set forth in SEQ ID NO: 3 and a $V_L$ comprising a sequence set forth in SEQ ID NO: 7);

(iii) RF16-242G (comprising a $V_H$ comprising a sequence set forth in SEQ ID NO: 4 and a $V_L$ comprising a sequence set forth in SEQ ID NO: 8);

(iv) RF16-226 (comprising a $V_H$ comprising a sequence set forth in SEQ ID NO: 2 and a $V_L$ comprising a sequence set forth in SEQ ID NO: 9);

(v) RF16-214 (comprising a $V_H$ comprising a sequence set forth in SEQ ID NO: 3 and a $V_L$ comprising a sequence set forth in SEQ ID NO: 10);

(vi) RF16-242 (comprising a $V_H$ comprising a sequence set forth in SEQ ID NO: 5 and a $V_L$ comprising a sequence set forth in SEQ ID NO: 11);

(vii) RF16-191 (comprising a $V_H$ comprising a sequence set forth in SEQ ID NO: 46 and a $V_L$ comprising a sequence set forth in SEQ ID NO: 50); or (viii) RF16-203 (comprising a $V_H$ comprising a sequence set forth in SEQ ID NO: 47 and a $V_L$ comprising a sequence set forth in SEQ ID NO: 51).

In some examples, the protein binds to an epitope in C2 that overlaps with the epitope bound by:

(i) RF16-226G (comprising a heavy chain variable region ($V_H$) comprising a sequence set forth in SEQ ID NO: 2 and a light chain variable region ($V_L$) comprising a sequence set forth in SEQ ID NO: 6);

(ii) RF16-214G (comprising a $V_H$ comprising a sequence set forth in SEQ ID NO: 3 and a $V_L$ comprising a sequence set forth in SEQ ID NO: 7); or (iii) RF16-242G (comprising a $V_H$ comprising a sequence set forth in SEQ ID NO: 4 and a $V_L$ comprising a sequence set forth in SEQ ID NO: 8).

In some examples, the protein competitively inhibits binding of any one or more of the following antibodies to C2:

(i) RF16-226G (comprising a heavy chain variable region ($V_H$) comprising a sequence set forth in SEQ ID NO: 2 and a light chain variable region ($V_L$) comprising a sequence set forth in SEQ ID NO: 6);

(ii) RF16-214G (comprising a $V_H$ comprising a sequence set forth in SEQ ID NO: 3 and a $V_L$ comprising a sequence set forth in SEQ ID NO: 7);

(iii) RF16-242G (comprising a $V_H$ comprising a sequence set forth in SEQ ID NO: 4 and a $V_L$ comprising a sequence set forth in SEQ ID NO: 8);

(iv) RF16-226 (comprising a $V_H$ comprising a sequence set forth in SEQ ID NO: 2 and a $V_L$ comprising a sequence set forth in SEQ ID NO: 9);

(v) RF16-214 (comprising a $V_H$ comprising a sequence set forth in SEQ ID NO: 3 and a $V_L$ comprising a sequence set forth in SEQ ID NO: 10);

(vi) RF16-242 (comprising a $V_H$ comprising a sequence set forth in SEQ ID NO: 5 and a $V_L$ comprising a sequence set forth in SEQ ID NO: 11);

(vii) RF16-191 (comprising a $V_H$ comprising a sequence set forth in SEQ ID NO: 46 and a $V_L$ comprising a sequence set forth in SEQ ID NO: 50); or (viii) RF16-203 (comprising a $V_H$ comprising a sequence set forth in SEQ ID NO: 47 and a $V_L$ comprising a sequence set forth in SEQ ID NO: 51).

In some examples, the protein competitively inhibits binding of any one or more of the following antibodies to C2:

(i) RF16-226G (comprising a $V_H$ comprising a sequence set forth in SEQ ID NO: 2 and a $V_L$ comprising a sequence set forth in SEQ ID NO: 6);

(ii) RF16-214G (comprising a $V_H$ comprising a sequence set forth in SEQ ID NO: 3 and a $V_L$ comprising a sequence set forth in SEQ ID NO: 7); or (iii) RF16-242G (comprising a $V_H$ comprising a sequence set forth in SEQ ID NO: 4 and a $V_L$ comprising a sequence set forth in SEQ ID NO: 8).

The present inventors have shown that antibodies RF16-226G, RF16-214G, RF16-242G, RF16-226, RF16-214, RF16-242, RF16-191, and RF16-203 bind to C2 in a pH-dependent manner and bind to C2 on a unique epitope relative to non-pH-dependent antibodies. Thus, as the skilled person would appreciate, other proteins that competitively inhibit binding of, or bind to the same epitope as, one of these antibodies would also be expected to have pH-dependent binding qualities. Suitable methods for determining the epitope of a binding protein, or determining competitive inhibition of binding, are described herein.

In some examples, the protein binds to C2 at pH 7.3 with an affinity which is at least 1.5-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 11-fold greater, or at least 12-fold greater than at pH 6.0.

In one example, the protein binds to C2 at pH 7.3 with an affinity which is at least 2-fold greater than at pH 6.0. In one example, the protein binds to C2 at pH 7.3 with an affinity which is at least 10-fold greater than at pH 6.0.

In some examples, the protein binds to C2 at pH 7.3 with an affinity of at least about 500 nM, at least about 250 nM, at least about 100 nM, at least about 50 nM, at least about 30 nM, at least about 15 nM, or at least about 10 nM, wherein affinity is determined in an assay in which the protein is immobilized and C2 is contacted with the immobilized protein. Suitable methods for determining the affinity of a protein for C2 are described herein.

In one example, the protein binds to C2 at pH 7.3 with an affinity of at least about 30 nM, wherein affinity is determined in an assay in which the protein is immobilized and C2 is contacted with the immobilized protein.

In some examples, the protein binds to C2 at pH 6.0 with an affinity of at most about 20 nM, at most about 35 nM, at most about 50 nM, at most about 75 nM, at most about 100 nM, or at most about 120 nM, wherein affinity is determined in an assay in which the protein is immobilized and C2 is contacted with the immobilized protein.

In some examples, the protein binds to C2 at pH 6.0 with an affinity of at most 50 nM, wherein affinity is determined in an assay in which the protein is immobilized and C2 is contacted with the immobilized protein.

In one example, the protein binds to C2 at pH 7.3 with an affinity of at least about 30 nM and the protein binds to C2 at pH 6.0 with an affinity of at most 50 nM, wherein affinity is determined in an assay in which the protein is immobilized and C2 is contacted with the immobilized protein.

In some examples, the affinity of the protein to C2 is not sensitive to $Ca^{2+}$ concentration. In one example, the affinity of the protein to C2 in the presence of about 2 mM $Ca^{2+}$ is similar to the affinity of the protein to C2 in the absence of $Ca^{2+}$ (i.e., 0 mM $Ca^{2+}$). In some examples, the affinities of the protein to C2 in the presence of about 2 mM $Ca^{2+}$ and the absence of $Ca^{2+}$ are within 4-fold, 3-fold, 2-fold, 1.5-fold, or 1.2-fold of one another. In some examples, the affinities of the protein to C2 in the presence of about 2 mM $Ca^{2+}$ and the absence of $Ca^{2+}$ are determined at pH 7.3. In some examples, the affinities of the protein to C2 in the presence of about 2 mM $Ca^{2+}$ and the absence of $Ca^{2+}$ are determined at pH 6.0.

In one example, the affinities of the protein to C2 in the presence of about 2 mM $Ca^{2+}$ and the absence of $Ca^{2+}$ are within 2-fold of one another.

In some examples, the affinity of the protein to C2 in the presence of about 2 mM $Ca^{2+}$ is lower, or is no more than 4-fold, 3-fold, 2-fold, 1.5-fold, or 1.2-fold higher, than the affinity of the protein to C2 in the absence of (i.e., 0 mM) $Ca^{2+}$.

In some examples, the protein binds to both human and cynomolgus monkey C2, e.g., with a similar affinity. Such proteins are advantageous as they facilitate pre-clinical studies in a closely related non-human mammal.

In some examples, the affinities of the protein to human and cynomolgus monkey C2 are within 5-fold of one another. In some examples, the affinities of the protein to human and cynomolgus monkey C2 are within 4-fold, 3-fold, 2-fold, or 1.5-fold of one another.

In some examples, the protein binds to cynomolgus monkey C2 at pH 7.3 with an affinity of at least about 500 nM, at least about 250 nM, at least about 100 nM, at least about 50 nM, at least about 30 nM, at least about 15 nM, or at least about 10 nM, wherein affinity is determined in an assay in which the protein is immobilized and cynomolgus monkey C2 is contacted with the immobilized protein.

In some examples, the protein binds to cynomolgus monkey C2 at pH 6.0 with an affinity of at most about 20 nM, at most about 35 nM, at most about 50 nM, at most about 75 nM, at most about 100 nM, or at most about 120 nM, wherein affinity is determined in an assay in which the protein is immobilized and cynomolgus monkey C2 is contacted with the immobilized protein.

In some examples, the protein binds to cynomolgus monkey C2 at pH 7.3 with an affinity which is at least 1.5-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 11-fold greater, or at least 12-fold greater than at pH 6.0.

In some examples, the protein does not detectably bind to dog C2, rat C2, rabbit C2, pig C2, and/or sheep C2.

In some examples, the protein binds to mouse C2. In some examples, the protein binds to mouse C2 with an affinity of at least 1000 nM, or at least 500 nM, or at least 200 nM. In one example, the protein binds to mouse C2 with an affinity of at least 200 nM.

In some examples, the affinity of the protein for a polypeptide of SEQ ID NO: 1 in which an alanine is substituted for one of:

(i) the lysine at position 443 of SEQ ID NO:1;
(ii) the histidine at position 331 of SEQ ID NO:1; or
(iii) the lysine at position 457 of SEQ ID NO:1,
is lower than the affinity of the protein to a polypeptide of SEQ ID NO: 1.

The present inventors have shown that the above amino acids in C2 are involved in the binding of pH-dependent binding proteins.

In some examples, the affinity of the protein for a polypeptide of SEQ ID NO: 1 in which an alanine is substituted for the lysine at position 443 is lower than the affinity of the protein for a polypeptide of SEQ ID NO: 1. In some examples, the affinity of the protein to a polypeptide of SEQ ID NO: 1 in which an alanine is substituted for the histidine at position 331 is lower than the affinity of the protein to a polypeptide of SEQ ID NO: 1. In some examples, the affinity of the protein to a polypeptide of SEQ ID NO: 1 in which an alanine is substituted for the lysine at position 457 is lower than the affinity of the protein to a polypeptide of SEQ ID NO: 1.

In some examples, the affinity of the protein to
(i) a polypeptide of SEQ ID NO: 1 in which an alanine is substituted for the lysine at position 443; and
(ii) a polypeptide of SEQ ID NO: 1 in which an alanine is substituted for the histidine at position 331, is lower than the affinity of the protein to a polypeptide of SEQ ID NO: 1.

In some examples, the affinity of the protein to
(i) a polypeptide of SEQ ID NO: 1 in which an alanine is substituted for the lysine at position 443;
(ii) a polypeptide of SEQ ID NO: 1 in which an alanine is substituted for the histidine at position 331; and
(iii) a polypeptide of SEQ ID NO: 1 in which an alanine is substituted for the lysine at position 457,
is lower than the affinity of the protein to a polypeptide of SEQ ID NO: 1.

In some examples, the affinity of the protein for a polypeptide of SEQ ID NO: 1 in which an alanine is substituted for the lysine at position 274, the phenylalanine at position 437, the aspartic acid at position 454, the methionine at position 648, the asparagine at position 703, the leucine at position 706, or the proline at position 724 is lower than the affinity of the protein to a polypeptide of SEQ ID NO: 1. In some examples, the affinity of the protein for a polypeptide of SEQ ID NO: 1 in which a serine is substituted for the alanine at position 717 is lower than the affinity of the protein to a polypeptide of SEQ ID NO: 1.

In some examples, the affinity of the protein to
(i) a polypeptide of SEQ ID NO: 1 in which an alanine is substituted for the lysine at position 443;
(ii) a polypeptide of SEQ ID NO: 1 in which an alanine is substituted for the histidine at position 331;
(iii) a polypeptide of SEQ ID NO: 1 in which an alanine is substituted for the lysine at position 457;
(iv) a polypeptide of SEQ ID NO: 1 in which an alanine is substituted for the lysine at position 274;
(v) a polypeptide of SEQ ID NO: 1 in which an alanine is substituted for the phenylalanine at position 437;
(vi) a polypeptide of SEQ ID NO: 1 in which an alanine is substituted for the aspartic acid at position 454;
(vii) a polypeptide of SEQ ID NO: 1 in which an alanine is substituted for the methionine at position 648;
(viii) a polypeptide of SEQ ID NO: 1 in which an alanine is substituted for the asparagine at position 703;
(ix) a polypeptide of SEQ ID NO: 1 in which an alanine is substituted for the leucine at position 706;
(x) a polypeptide of SEQ ID NO: 1 in which an alanine is substituted for the proline at position 724; and
(xi) a polypeptide of SEQ ID NO: 1 in which a serine is substituted for the alanine at position 717,
is lower than the affinity of the protein to a polypeptide of SEQ ID NO: 1.

In some examples, the affinity of the protein for a polypeptide of SEQ ID NO: 1 in which an alanine is substituted for the leucine at position 439, the leucine at position 453, the phenylalanine at position 270, the isoleucine at position 271, the lysine at position 274, the glutamic acid at position 275, the aspartic acid at position 282, or the isoleucine at position 320 is lower than the affinity of the protein to a polypeptide of SEQ ID NO: 1.

In some examples, the affinity of the protein for the polypeptide comprising the substitution is at least 5-fold, 10-fold, 15-fold, or 20-fold lower than the affinity of the protein to the polypeptide of SEQ ID NO:1. In some examples, the affinity of the protein for the polypeptide comprising the substitution is at least 10-fold lower than the affinity of the protein to the polypeptide of SEQ ID NO: 1. In some examples, the affinity of the protein for the polypeptide comprising the substitution is at least 20-fold lower than the affinity of the protein to the polypeptide of SEQ ID NO: 1.

In some examples, the protein does not detectably bind to the polypeptide comprising the alanine substitution at position 443 of SEQ ID. NO: 1. In some examples, the protein does not detectably bind to the polypeptide comprising the alanine substitution at position 331 of SEQ ID NO: 1. In some examples, the protein does not detectably bind to the polypeptide comprising the alanine substitution at position 457 of SEQ ID NO: 1.

In some examples, the protein does not detectably bind to
(i) a polypeptide of SEQ ID NO: 1 in which an alanine is substituted for the lysine at position 443; and
(ii) a polypeptide of SEQ ID NO: 1 in which an alanine is substituted for the histidine at position 331.

In some examples, the protein does not detectably bind to
(i) a polypeptide of SEQ ID NO: 1 in which an alanine is substituted for the lysine at position 443; and
(ii) a polypeptide of SEQ ID NO: 1 in which an alanine is substituted for the histidine at position 331; and
(iii) a polypeptide of SEQ ID NO: 1 in which an alanine is substituted for the lysine at position 457.

Additional forms of a polypeptide comprising the amino acids of SEQ ID NO: 1 with or without other substitutions bound or not significantly bound or not detectably bound by a protein of the present disclosure are described herein and are to be taken to apply mutatis mutandis to the present examples of the disclosure.

In some examples, the protein binds to an epitope comprising residues within the von Willebrand factor A-type (VWA) domain of C2. In some examples, the protein binds to an epitope comprising residues within the peptidase S1 domain of C2. In some examples, the protein binds to an epitope comprising residues within the VWA domain and the peptidase S1 domain of C2. In some examples, at least 50%, at least 60%, at least 70%, at least 80%, or at least 90% of the residues in the epitope are within the VWA domain of C2. In some examples, at least 50% of the residues in the epitope are within the VWA domain of C2. In some examples, at least 90% of the residues in the epitope are within the VWA domain of C2.

In some examples, the protein binds to an epitope comprising residues within one or two or three regions selected from 266-284, 318-333, and 428-459 of SEQ ID NO: 1. In some examples, the protein binds to an epitope comprising residues within the regions 266-284, 318-333, and 428-459 of SEQ ID NO: 1. In some examples, the protein binds to an epitope comprising the amino acids at positions 274, 331, 443, and 457 of SEQ ID NO: 1. In some examples, the protein binds to an epitope comprising at least 5, at least 6, at least 7, at least 8, at least 9, at least 10, or all of the amino acids at positions 274, 331, 437, 443, 454, 457, 648, 703, 706, 717, and 724 of SEQ ID NO: 1. In some examples, the protein binds to an epitope comprising the amino acids at positions 274, 331, 437, 443, 454, 457, 648, 703, 706, 717, and 724 of SEQ ID NO: 1.

In some examples, the protein inhibits the human classical complement pathway and/or the lectin complement pathway with an $IC_{50}$ of at least 50 nM or at least 10 nM, wherein the $IC_{50}$ is determined by a Wieslab® complement assay. Advantageously, such proteins can, in addition to reducing the concentration of C2 in circulation by virtue of their pH-dependent binding, also directly inhibit complement activity.

In some examples, the protein inhibits the human classical complement pathway and/or the human lectin complement pathway with an $IC_{50}$ of at least 500 nM, at least 250 nM, at least 100 nM, at least 50 nM, at least 25 nM or at least 10 nM, wherein the $IC_{50}$ is determined by a Wieslab® complement assay. In some examples, the protein inhibits the human classical complement pathway and/or the human lectin complement pathway with an $IC_{50}$ of at least 25 nM, wherein the $IC_{50}$ is determined by a Wieslab® complement assay.

Methods for determining the inhibitory activity of the protein will be apparent to the skilled person and/or described herein. In one example, complement inhibitory activity is determined using an in vitro assay. For example, complement activity is measured using an enzyme immunoassay (e.g., an immunoassay that measures complement activation, such as a Wieslab® complement assay kit). For example, complement inhibitory activity is determined using labelled antibodies specific for an antigen or an epitope produced during complement activation (e.g., C5b-9 or an epitope present in C5b-C9). In one example, the wells of a microtitre plate are coated with specific activators of the classical, lectin or alternative pathway. In one example, the protein of the disclosure is incubated with normal human serum and appropriate assay diluent (i.e., a diluent comprising appropriate blocking components to ensure specific activation of the classical, lectin or alternative pathway) and added to microtitre plate wells coated with specific activators of the classical, lectin or alternative pathway and the amount of C5b-9 complex formed is detected using a specific alkaline phosphatase labelled antibody to the C5b-9. In one example, the amount of complement activation product (i.e., C5b-9) produced is proportional to the functional activity of the complement pathway. In one example, the half-maximal inhibitor concentration (i.e., $IC_{50}$) is determined. In another example, complement inhibitory activity is determined using a hemolysis assay (e.g., classical pathway (i.e., CH50) and alternative pathway (ApH50) inhibition assays).

In some examples, the protein inhibits the cynomolgus monkey classical complement pathway and/or the cynomolgus monkey lectin complement pathway with an $IC_{50}$ of at least 500 nM, at least 250 nM, at least 100 nM, at least 50 nM, at least 25 nM or at least 10 nM, wherein the $IC_{50}$ is determined by a Wieslab® complement assay. In some examples, the protein inhibits the cynomolgus monkey classical complement pathway and/or the cynomolgus monkey lectin complement pathway with an $IC_{50}$ of at least 25 nM, wherein the $IC_{50}$ is determined by a Wieslab® complement assay.

In some examples, the protein inhibits C1s-mediated proteolysis of C2. Thus, in some examples, the protein is able to inhibit activation of C2 by preventing release of the enzymatically active C2a fragment. Inhibition of C1s-mediated proteolysis of C2 by proteins described herein can be measured in vitro using the methods described in the Examples, or any other method known in the art. For example, mixtures containing C2 with and without the protein can be incubated with varying concentrations of C1s. Following incubation with C1s, the amount of C2a (the larger enzymatically active fragment of C2) and/or C2b (the smaller inactive fragment) produced by proteolysis can be measured using e.g., SDS-PAGE for reactions with and without the protein. Inhibition of C1s-mediated proteolysis of C2 occurs if, at a given concentration of C2 and C1s, the amount of C2a and/or C2b produced is less in the presence of the protein relative to the absence of the protein.

In some examples, the protein does not detectably bind to C2a. In some examples, the protein does not detectably bind to human C2a.

In some examples, the protein does not detectably bind to C2b. In some examples, the protein does not detectably bind to human C2b.

In some examples, the protein comprises a $V_H$. In some examples, the protein comprises a $V_L$. In some examples, the protein comprises a $V_H$ and a $V_L$.

In some examples, the protein comprises (i) a $V_H$ comprising a complementarity determining region (CDR) 1 comprising a sequence at least about 70%, 80%, or 90% identical to any of the sequences set forth in SEQ ID NOs: 12-14, 54 or 60, a CDR2 comprising a sequence at least about 70%, 80%, or 90% identical to any of the sequences set forth in SEQ ID NOs: 15-17, 55 or 61, and a CDR3 comprising a sequence at least about 70%, 80%, or 90% identical to any of the sequences set forth in SEQ ID NOs: 18-20, 56 or 62; and/or (ii) a $V_L$ comprising a CDR1 comprising a sequence at least about 70%, 80%, or 90% identical to any of the sequences set forth in SEQ ID NOs: 21-23, 57 or 63, a CDR2 comprising a sequence at least about 70%, 80%, or 90% identical to any of the sequences set forth in SEQ ID NOs: 24-26, 58 or 64, and a CDR3 comprising a sequence at least about 70%, 80%, or 90% identical to any of the sequences set forth in SEQ ID NOs: 27-29, 59 or 65.

In some examples, the protein comprises (i) a $V_H$ comprising a complementarity determining region (CDR) 1 comprising a sequence at least about 70%, 80%, or 90% identical to any of the sequences set forth in SEQ ID NOs: 12-14, a CDR2 comprising a sequence at least about 70%, 80%, or 90% identical to any of the sequences set forth in SEQ ID NOs: 15-17 and a CDR3 comprising a sequence at least about 70%, 80%, or 90% identical to any of the sequences set forth in SEQ ID NOs: 18-20; and/or (ii) a $V_L$ comprising a CDR1 comprising a sequence at least about 70%, 80%, or 90% identical to any of the sequences set forth in SEQ ID NOs: 21-23, a CDR2 comprising a sequence at least about 70%, 80%, or 90% identical to any of the sequences set forth in SEQ ID NOs: 24-26 and a CDR3 comprising a sequence at least about 70%, 80%, or 90% identical to any of the sequences set forth in SEQ ID NOs: 27-29.

In some examples, the protein comprises a $V_H$ comprising a CDR1, a CDR2, and a CDR3 comprising the sequences set forth in SEQ ID NOs: 40, 41, and 42 respectively. In some examples, the protein comprises a $V_L$ comprising a CDR1, a CDR2, and a CDR3 comprising the sequences set forth in SEQ ID NOs: 43, 44, and 45 respectively.

In some examples, the protein comprises a $V_H$ comprising a CDR1, a CDR2, and a CDR3 comprising the sequences set forth in SEQ ID NOs: 40, 41, and 42 respectively and a $V_L$ comprising a CDR1, a CDR2, and a CDR3 comprising the sequences set forth in SEQ ID NOs: 43, 44, and 45 respectively.

In some examples, the protein comprises a $V_H$ comprising a CDR1, a CDR2, and a CDR3 comprising the sequences set forth in SEQ ID NOs: 66, 67, and 68 respectively. In some examples, the protein comprises a $V_L$ comprising a CDR1, a CDR2, and a CDR3 comprising the sequences set forth in SEQ ID NOs: 69, 70, and 71 respectively.

In some examples, the protein comprises a $V_H$ comprising a CDR1, a CDR2, and a CDR3 comprising the sequences set forth in SEQ ID NOs: 66, 67, and 68 respectively and a $V_L$ comprising a CDR1, a CDR2, and a CDR3 comprising the sequences set forth in SEQ ID NOs: 69, 70, and 71 respectively.

In some examples, the protein comprises (i) a $V_H$ comprising a CDR1 comprising a sequence having no more than 2 amino acid substitutions relative to SEQ ID NO: 12, a CDR2 comprising a sequence having no more than 4 amino acid substitutions relative to SEQ ID NO: 15, and a CDR3 comprising a sequence having no more than 2 amino acid substitutions relative to SEQ ID NO: 18, and a $V_L$ comprising a CDR1 comprising a sequence having no more than 3 amino acid substitutions relative to SEQ ID NO: 21, a CDR2 comprising a sequence having no more than 2 amino acid substitutions relative to SEQ ID NO: 24, and a CDR3 comprising a sequence having no more than 3 amino acid substitutions relative to SEQ ID NO: 27;

(ii) a $V_H$ comprising a CDR1 comprising a sequence having no more than 2 amino acid substitutions relative to SEQ ID NO: 13, a CDR2 comprising a sequence having no more than 4 amino acid substitutions relative to SEQ ID NO: 16, and a CDR3 comprising a sequence having no more than 3 amino acid substitutions relative to SEQ ID NO: 19, and a $V_L$ comprising a CDR1 comprising a sequence having no more than 3 amino acid substitutions relative to SEQ ID NO: 22, a CDR2 comprising a sequence having no more than 2 amino acid substitutions relative to SEQ ID NO: 25, and a CDR3 comprising a sequence having no more than 3 amino acid substitutions relative to SEQ ID NO: 28;

(iii) a $V_H$ comprising a CDR1 comprising a sequence having no more than 2 amino acid substitutions relative to SEQ ID NO: 14, a CDR2 comprising a sequence having no more than 4 amino acid substitutions relative to SEQ ID NO: 17, and a CDR3 comprising a sequence having no more than 3 amino acid substitutions relative to SEQ ID NO: 20, and a $V_L$ comprising a CDR1 comprising a sequence having no more than 3 amino acid substitutions relative to SEQ ID NO: 23, a CDR2 comprising a sequence having no more than 2 amino acid substitutions relative to SEQ ID NO: 26, and a CDR3 comprising a sequence having no more than 3 amino acid substitutions relative to SEQ ID NO: 29;

(iv) a $V_H$ comprising a CDR1 comprising a sequence having no more than 2 amino acid substitutions relative to SEQ ID NO: 54, a CDR2 comprising a sequence having no more than 4 amino acid substitutions relative to SEQ ID NO: 55, and a CDR3 comprising a sequence having no more than 3 amino acid substitutions relative to SEQ ID NO: 56 and, a $V_L$ comprising a CDR1 comprising a sequence having no more than 3 amino acid substitutions relative to SEQ ID NO: 57, a CDR2 comprising a sequence having no more than 2 amino acid substitutions relative to SEQ ID NO: 58, and a CDR3 comprising a sequence having no more than 3 amino acid substitutions relative to SEQ ID NO: 59; or (v) a $V_H$ comprising a CDR1 comprising a sequence having no more than 2 amino acid substitutions relative to SEQ ID NO: 60, a CDR2 comprising a sequence having no more than 4 amino acid substitutions relative to SEQ ID NO: 61, and a CDR3 comprising a sequence having no more than 3 amino acid substitutions relative to SEQ ID NO: 62, and a V_L comprising a CDR1 comprising a sequence having no more than 3 amino acid substitutions relative to SEQ ID NO: 63, a CDR2 comprising a sequence having no more than 2 amino acid substitutions relative to SEQ ID NO: 64, and a CDR3 comprising a sequence having no more than 3 amino acid substitutions relative to SEQ ID NO: 65.

In some examples, the amino acid substitutions are conservative amino acid substitutions.

In some examples, the protein comprises (i) a V_H comprising a CDR1, a CDR2, and a CDR3 comprising the sequences set forth in SEQ ID NOs: 12, 15, and 18 respectively and a V_L comprising a CDR1, a CDR2, and a CDR3 comprising the sequences set forth in SEQ ID NOs: 21, 24, and 27 respectively;

(ii) a V_H comprising a CDR1, a CDR2, and a CDR3 comprising the sequences set forth in SEQ ID NOs: 13, 16, and 19 respectively and a V_L comprising a CDR1, a CDR2, and a CDR3 comprising the sequences set forth in SEQ ID NOs: 22, 25, and 28 respectively;

(iii) a V_H comprising a CDR1, a CDR2, and a CDR3 comprising the sequences set forth in SEQ ID NOs: 14, 17, and 20 respectively and a V_L comprising a CDR1, a CDR2, and a CDR3 comprising the sequences set forth in SEQ ID NOs: 23, 26, and 29 respectively;

(iv) a V_H comprising a CDR1, a CDR2, and a CDR3 comprising the sequences set forth in SEQ ID NOs: 54, 55, and 56 respectively and a V_L comprising a CDR1, a CDR2, and a CDR3 comprising the sequences set forth in SEQ ID NOs: 57, 58, and 59 respectively; or (v) a V_H comprising a CDR1, a CDR2, and a CDR3 comprising the sequences set forth in SEQ ID NOs: 60, 61, and 62 respectively and a V_L comprising a CDR1, a CDR2, and a CDR3 comprising the sequences set forth in SEQ ID NOs: 63, 64, and 65 respectively.

In some examples, the protein comprises (i) a V_H comprising a CDR1, a CDR2, and a CDR3 comprising the sequences set forth in SEQ ID NOs: 12, 15, and 18 respectively and a V_L comprising a CDR1, a CDR2, and a CDR3 comprising the sequences set forth in SEQ ID NOs: 21, 24, and 27 respectively;

(ii) a V_H comprising a CDR1, a CDR2, and a CDR3 comprising the sequences set forth in SEQ ID NOs: 13, 16, and 19 respectively and a V_L comprising a CDR1, a CDR2, and a CDR3 comprising the sequences set forth in SEQ ID NOs: 22, 25, and 28 respectively; or (iii) a V_H comprising a CDR1, a CDR2, and a CDR3 comprising the sequences set forth in SEQ ID NOs: 14, 17, and 20 respectively and a V_L comprising a CDR1, a CDR2, and a CDR3 comprising the sequences set forth in SEQ ID NOs: 23, 26, and 29 respectively.

In some examples, the protein comprises (i) a V_H comprising a CDR1, a CDR2, and a CDR3 consisting of the sequences set forth in SEQ ID NOs: 12, 15, and 18 respectively and a V_L comprising a CDR1, a CDR2, and a CDR3 consisting of the sequences set forth in SEQ ID NOs: 21, 24, and 27 respectively;

(ii) a V_H comprising a CDR1, a CDR2, and a CDR3 consisting of the sequences set forth in SEQ ID NOs: 13, 16, and 19 respectively and a V_L comprising a CDR1, a CDR2, and a CDR3 consisting of the sequences set forth in SEQ ID NOs: 22, 25, and 28 respectively;

(iii) a V_H comprising a CDR1, a CDR2, and a CDR3 consisting of the sequences set forth in SEQ ID NOs: 14, 17, and 20 respectively and a V_L comprising a CDR1, a CDR2, and a CDR3 consisting of the sequences set forth in SEQ ID NOs: 23, 26, and 29 respectively;

(iv) a V_H comprising a CDR1, a CDR2, and a CDR3 consisting of the sequences set forth in SEQ ID NOs: 54, 55, and 56 respectively and a V_L comprising a CDR1, a CDR2, and a CDR3 consisting of the sequences set forth in SEQ ID NOs: 57, 58, and 59 respectively; or (v) a V_H comprising a CDR1, a CDR2, and a CDR3 consisting of the sequences set forth in SEQ ID NOs: 60, 61, and 62 respectively and a V_L comprising a CDR1, a CDR2, and a CDR3 consisting of the sequences set forth in SEQ ID NOs: 63, 64, and 65 respectively.

In some examples, the protein comprises (i) a V_H comprising a CDR1, a CDR2, and a CDR3 consisting of the sequences set forth in SEQ ID NOs: 12, 15, and 18 respectively and a V_L comprising a CDR1, a CDR2, and a CDR3 consisting of the sequences set forth in SEQ ID NOs: 21, 24, and 27 respectively;

(ii) a V_H comprising a CDR1, a CDR2, and a CDR3 consisting of the sequences set forth in SEQ ID NOs: 13, 16, and 19 respectively and a V_L comprising a CDR1, a CDR2, and a CDR3 consisting of the sequences set forth in SEQ ID NOs: 22, 25, and 28 respectively; or (iii) a V_H comprising a CDR1, a CDR2, and a CDR3 consisting of the sequences set forth in SEQ ID NOs: 14, 17, and 20 respectively and a V_L comprising a CDR1, a CDR2, and a CDR3 consisting of the sequences set forth in SEQ ID NOs: 23, 26, and 29 respectively.

In some examples, the protein comprises a V_H comprising a CDR1, a CDR2, and a CDR3 comprising sequences which are at least 70%, 80%, or 90% identical to the sequences set forth in SEQ ID NOs: 12, 15, and 18 respectively. In some examples, the protein comprises a V_L comprising a CDR1, a CDR2, and a CDR3 comprising sequences which are at least 70%, 80%, or 90% identical to the sequences set forth in SEQ ID NOs: 21, 24, and 27 respectively.

In some examples, the protein comprises a V_H comprising a CDR1, a CDR2, and a CDR3 comprising the sequences set forth in SEQ ID NOs: 12, 15, and 18 respectively. In some examples, the protein comprises a V_L comprising a CDR1, a CDR2, and a CDR3 comprising the sequences set forth in SEQ ID NOs: 21, 24, and 27 respectively.

In some examples, the protein comprises a V_H comprising a CDR1, a CDR2, and a CDR3 comprising the sequences set forth in SEQ ID NOs: 12, 15, and 18 respectively and a V_L comprising a CDR1, a CDR2, and a CDR3 comprising the sequences set forth in SEQ ID NOs: 21, 24, and 27 respectively.

In some examples, the protein comprises (i) a V_H comprising a sequence at least about 70%, 80%, 90%, or 95% identical to any of the sequences set forth in SEQ ID NOs: 2-5, 46 or 47; and/or (ii) a V_L comprising a sequence at least about 70%, 80%, 90%, or 95% identical to any of the sequences set forth in SEQ ID NOs: 6-11, 50 or 51.

In some examples, the protein comprises (i) a V_H comprising a sequence at least about 70%, 80%, 90%, or 95% identical to any of the sequences set forth in SEQ ID NOs: 2-5; and/or (ii) a V$_L$ comprising a sequence at least about 70%, 80%, 90%, or 95% identical to any of the sequences set forth in SEQ ID NOs: 6-11.

In some examples, the protein comprises (i) a V$_H$ comprising a sequence at least about 70%, 80%, 90%, or 95% identical to the sequence set forth in SEQ ID NO: 2 and a V$_L$ comprising a sequence at least about 70%, 80%, 90%, or 95% identical to the sequence set forth in SEQ ID NO: 6 or 9;

(ii) a V$_H$ comprising a sequence at least about 70%, 80%, 90%, or 95% identical to the sequence set forth in SEQ ID NO: 3 and a V$_L$ comprising a sequence at least about 70%, 80%, 90%, or 95% identical to the sequence set forth in SEQ ID NO: 7 or 10;

(iii) a V$_H$ comprising a sequence at least about 70%, 80%, 90%, or 95% identical to the sequence set forth in SEQ ID NO: 4 and a V$_L$ comprising a sequence at least about 70%, 80%, 90%, or 95% identical to the sequence set forth in SEQ ID NO: 8;

(iv) a V$_H$ comprising a sequence at least about 70%, 80%, 90%, or 95% identical to the sequence set forth in SEQ ID NO: 5 and a V$_L$ comprising a sequence at least about 70%, 80%, 90%, or 95% identical to the sequence set forth in SEQ ID NO: 11;

(v) a V$_H$ comprising a sequence at least about 70%, 80%, 90%, or 95% identical to the sequence set forth in SEQ ID NO: 46 and a V$_L$ comprising a sequence at least about 70%, 80%, 90%, or 95% identical to the sequence set forth in SEQ ID NO: 50; or (vi) a V$_H$ comprising a sequence at least about 70%, 80%, 90%, or 95% identical to the sequence set forth in SEQ ID NO: 47 and a V$_L$ comprising a sequence at least about 70%, 80%, 90%, or 95% identical to the sequence set forth in SEQ ID NO: 51.

In some examples, the protein comprises (i) a V$_H$ comprising a sequence at least about 70%, 80%, 90%, or 95% identical to the sequence set forth in SEQ ID NO: 2 and a V$_L$ comprising a sequence at least about 70%, 80%, 90%, or 95% identical to the sequence set forth in SEQ ID NO: 6 or 9;

(ii) a V$_H$ comprising a sequence at least about 70%, 80%, 90%, or 95% identical to the sequence set forth in SEQ ID NO: 3 and a V$_L$ comprising a sequence at least about 70%, 80%, 90%, or 95% identical to the sequence set forth in SEQ ID NO: 7 or 10;

(iii) a V$_H$ comprising a sequence at least about 70%, 80%, 90%, or 95% identical to the sequence set forth in SEQ ID NO: 4 and a V$_L$ comprising a sequence at least about 70%, 80%, 90%, or 95% identical to the sequence set forth in SEQ ID NO: 8; or (iv) a V$_H$ comprising a sequence at least about 70%, 80%, 90%, or 95% identical to the sequence set forth in SEQ ID NO: 5 and a V$_L$ comprising a sequence at least about 70%, 80%, 90%, or 95% identical to the sequence set forth in SEQ ID NO: 11.

In some examples, the protein comprises (i) a V$_H$ comprising a sequence set forth in SEQ ID NO: 2 and a V$_L$ comprising a sequence set forth in SEQ ID NO: 6 or 9;

(ii) a V$_H$ comprising a sequence set forth in SEQ ID NO: 3 and a V$_L$ comprising a sequence set forth in SEQ ID NO: 7 or 10;

(iii) a V$_H$ comprising a sequence set forth in SEQ ID NO: 4 and a V$_L$ comprising a sequence set forth in SEQ ID NO: 8;

(iv) a V$_H$ comprising a sequence set forth in SEQ ID NO: 5 and a V$_L$ comprising a sequence set forth in SEQ ID NO: 11;

(v) a V$_H$ comprising a sequence set forth in SEQ ID NO: 46 and a V$_L$ comprising a sequence set forth in SEQ ID NO: 50; or (vi) a V$_H$ comprising a sequence set forth in SEQ ID NO: 47 and a V$_L$ comprising a sequence set forth in SEQ ID NO: 51.

In some examples, the protein comprises (i) a V$_H$ comprising a sequence set forth in SEQ ID NO: 2 and a V$_L$ comprising a sequence set forth in SEQ ID NO: 6 or 9;

(ii) a V$_H$ comprising a sequence set forth in SEQ ID NO: 3 and a V$_L$ comprising a sequence set forth in SEQ ID NO: 7 or 10;

(iii) a V$_H$ comprising a sequence set forth in SEQ ID NO: 4 and a V$_L$ comprising a sequence set forth in SEQ ID NO: 8; or (iv) a V$_H$ comprising a sequence set forth in SEQ ID NO: 5 and a V$_L$ comprising a sequence set forth in SEQ ID NO: 11.

In some examples, the protein comprises (i) a V$_H$ comprising a sequence at least about 70%, 80%, 90%, or 95% identical to the sequence set forth in SEQ ID NO: 46 and a V$_L$ comprising a sequence at least about 70%, 80%, 90%, or 95% identical to the sequence set forth in SEQ ID NO: 50;

(ii) a V$_H$ comprising a sequence at least about 70%, 80%, 90%, or 95% identical to the sequence set forth in SEQ ID NO: 47 and a V$_L$ comprising a sequence at least about 70%, 80%, 90%, or 95% identical to the sequence set forth in SEQ ID NO: 51;

(iii) a V$_H$ comprising a sequence at least about 70%, 80%, 90%, or 95% identical to the sequence set forth in SEQ ID NO: 48 and a V$_L$ comprising a sequence at least about 70%, 80%, 90%, or 95% identical to the sequence set forth in SEQ ID NO: 52; or (iv) a V$_H$ comprising a sequence at least about 70%, 80%, 90%, or 95% identical to the sequence set forth in SEQ ID NO:49 and a V$_L$ comprising a sequence at least about 70%, 80%, 90%, or 95% identical to the sequence set forth in SEQ ID NO: 53.

In some examples, the protein comprises (i) a V$_H$ comprising a sequence set forth in SEQ ID NO: 46 and a V$_L$ comprising a sequence set forth in SEQ ID NO: 50;

(ii) a V$_H$ comprising a sequence set forth in SEQ ID NO: 47 and a V$_L$ comprising a sequence set forth in SEQ ID NO: 51;

(iii) a V$_H$ comprising a sequence set forth in SEQ ID NO: 48 and a V$_L$ comprising a sequence set forth in SEQ ID NO: 52; or (iv) a V$_H$ comprising a sequence set forth in SEQ ID NO:49 and a V$_L$ comprising a sequence set forth in SEQ ID NO: 53.

In some examples, the protein comprises (i) a V$_H$ comprising a CDR1, a CDR2, and a CDR3 comprising the sequences set forth in SEQ ID NOs: 54, 55, and 56 respectively and a V$_L$ comprising a CDR1, a CDR2, and a CDR3 comprising the sequences set forth in SEQ ID NOs: 57, 58, and 59 respectively; or (ii) a V$_H$ comprising a CDR1, a CDR2, and a CDR3 comprising the sequences set forth in SEQ ID NOs: 60, 61, and 62 respectively and a V$_L$ comprising a CDR1, a CDR2, and a CDR3 comprising the sequences set forth in SEQ ID NOs: 63, 64, and 65 respectively.

In some examples, the protein comprises a $V_H$ and a $V_L$, wherein the $V_H$ and $V_L$ bind to form a Fv comprising the antigen binding site.

In some examples, the $V_H$ and the $V_L$ are in a single polypeptide chain. In some examples, the protein is:
(i) a single chain Fv fragment (scFv);
(ii) a dimeric scFv (di-scFv); or
(iii) at least one of (i) and/or (ii) linked to a constant region of an antibody, a fragment crystallizable (Fc) region or a heavy chain constant domain ($C_H$) 2 and/or $C_H$3.

In some examples, the $V_L$ and $V_H$ are in separate polypeptide chains. In some examples, the protein is:
(i) a diabody;
(ii) a triabody;
(iii) a tetrabody;
(iv) a Fab;
(v) a F(ab')$_2$;
(vi) a Fv; or
(vii) one of (i) to (vi) linked to a constant region of an antibody, an Fc region or a $C_H$2 and/or $C_H$3.

In some examples, the protein comprises an Fc region. In some examples, the protein is an antibody. In some examples, the protein is a naked antibody.

In some examples, the protein comprises one or more amino acid substitutions in the Fc region which increases the protein's affinity to neonatal Fc receptor (FcRn). Without wishing to be bound by theory, such amino acid substitutions may enhance the proteins "sweeping" capabilities by increasing the proportion of the proteins that are recycled into circulation after binding to FcRn. In some examples, the one or more amino acid substitutions increase the affinity of the protein to FcRn at pH 6.0.

In some examples, the one or more amino acid substitutions are selected from M252Y, S254T, T256E, V308P, N286E, M428L, N434A, and N434Y according to the EU numbering system of Kabat. In some examples, the protein comprises the following amino acid substitutions in its Fc region:
(i) M252Y,
(ii) N286E or V308P, and
(iii) N434Y.

In some examples, the protein is an antibody comprising a heavy chain comprising an amino acid sequence at least about 70%, 80%, 90%, 95%, or 98% identical to a sequence set forth in any one of SEQ ID NOs: 30-33 and a light chain comprising an amino acid sequence at least about 70%, 80%, 90%, 95%, or 98% identical to a sequence set forth in any one of SEQ ID NOs: 34-39.

In some examples, the protein is an antibody comprising a heavy chain comprising an amino acid sequence set forth in any one of SEQ ID NOs: 30-33 and a light chain comprising an amino acid sequence set forth in any one of SEQ ID NOs: 34-39.

In some examples, the protein is an antibody comprising
(i) a heavy chain comprising a sequence at least about 70%, 80%, 90%, or 95% identical to the sequence set forth in SEQ ID NO: 30 and a light chain comprising a sequence at least about 70%, 80%, 90%, or 95% identical to the sequence set forth in SEQ ID NO: 34 or 37;
(ii) a heavy chain comprising a sequence at least about 70%, 80%, 90%, or 95% identical to the sequence set forth in SEQ ID NO: 31 and a light chain comprising a sequence at least about 70%, 80%, 90%, or 95% identical to the sequence set forth in SEQ ID NO: 35 or 38;

(iii) a heavy chain comprising a sequence at least about 70%, 80%, 90%, or 95% identical to the sequence set forth in SEQ ID NO: 32 and a light chain comprising a sequence at least about 70%, 80%, 90%, or 95% identical to the sequence set forth in SEQ ID NO: 36; or
(iv) a heavy chain comprising a sequence at least about 70%, 80%, 90%, or 95% identical to the sequence set forth in SEQ ID NO: 33 and a light chain comprising a sequence at least about 70%, 80%, 90%, or 95% identical to the sequence set forth in SEQ ID NO: 39.

In some examples, the protein comprises
(i) a heavy chain comprising a sequence set forth in SEQ ID NO: 30 and a light chain comprising a sequence set forth in SEQ ID NO: 34 or 37;
(ii) a heavy chain comprising a sequence set forth in SEQ ID NO: 31 and a light chain comprising a sequence set forth in SEQ ID NO: 35 or 38;
(iii) a heavy chain comprising a sequence set forth in SEQ ID NO: 32 and a light chain comprising a sequence set forth in SEQ ID NO: 36; or
(iv) a heavy chain comprising a sequence set forth in SEQ ID NO: 33 and a light chain comprising a sequence set forth in SEQ ID NO: 39.

In some examples, the protein is an antibody comprising a heavy chain comprising an amino acid sequence set forth in SEQ ID NO: 30. In some examples, the protein is an antibody comprising a light chain comprising an amino acid sequence set forth in SEQ ID NO: 34.

In some examples, the protein is an antibody comprising a heavy chain comprising an amino acid sequence set forth in SEQ ID NO: 30 and a light chain comprising an amino acid sequence set forth in SEQ ID NO: 34.

In some examples, the protein is chimeric, de-immunized, humanized, human or primatized. In some examples, the protein is a human protein.

In some examples, the protein is conjugated to another compound. In one example, the other compound is a half-life extending moiety. In one example, the other compound is an immune modulator. In one example, the other compound is an immunosuppressant. In one example, the other compound is a detectable label. In one example, the other compound is one that is known to inhibit complement activity and/or is used to treat or prevent complement-mediated disorders.

Reference herein to a protein or antibody that "binds to" C2 provides literal support for a protein or antibody that "binds specifically to" C2.

The present disclosure also provides antigen binding domains or antigen binding fragments of the foregoing proteins or antibodies.

In one example, a protein or antibody as described herein comprises a constant region of an IgG4 antibody or a stabilized constant region of an IgG4 antibody. In one example, the protein or antibody comprises an IgG4 constant region with a proline at position 241 (according to the numbering system of Kabat (Kabat et al., Sequences of Proteins of Immunological Interest Washington DC United States Department of Health and Human Services, 1987 and/or 1991)).

The C-terminal lysine of the heavy chain constant region of a whole antibody of the disclosure may be removed, for example, during production or purification of the antibody, or by recombinantly engineering the nucleic acid encoding a heavy chain of the antibody. Accordingly, whole antibodies may comprise antibody populations with all C-terminal lysine residues removed, antibody populations with no C-terminal lysine residues removed, and antibody populations having a mixture of antibodies with and without the C-terminal lysine residue. In some examples, the antibody populations may additionally comprise antibodies in which the C-terminal lysine residue is removed in one of the heavy chain constant regions. Similarly, a composition of whole antibodies may comprise the same or a similar mix of antibody populations with or without the C-terminal lysine residue.

The protein of the disclosure may also comprise one or more other post-translational modifications (PTMs). PTMs of antibodies are well known in the art and include, but are not limited to, glycosylation, deamidation, isomerization, oxidation, and pyroglutamylation. For example, the protein may comprise one or more Asn or Gln residues which are deamidated to form Asp or Glu residues respectively. In this regard, reference to a sequence of amino acids herein (e.g., a SEQ ID NO) refers to the sequence of amino acids that exists at the time the protein is synthesized (e.g., by a ribosome). Thus, as a skilled person would appreciate, any SEQ ID NO provided herein encompasses the sequence of amino acids as synthesized, as well as any post-translationally modified versions thereof. For example, a SEQ ID NO comprising an Asn residue encompasses a protein having an Asn at that position and, if it has been deamidated, an Asp or isoAsp as well. A composition comprising a protein of the disclosure may comprise a mixture of proteins with and without a particular PTM. Additionally, such a composition may comprise proteins with different PTMs.

In one example, a protein of the disclosure comprises a $V_H$ disclosed herein linked or fused to an IgG4 constant region or stabilized IgG4 constant region (e.g., as discussed above) and the $V_L$ is linked to or fused to a kappa light chain constant region.

In one example, a protein as described herein is isolated and/or recombinant.

In one example, a protein of the disclosure is conjugated to another compound, for example, a detectable label or a compound that extends the half-life of the protein, such as polyethylene glycol or an albumin binding protein. In other examples, the protein is conjugated to a chemotherapeutic, such as a cytotoxic compound.

The present disclosure also provides a nucleic acid encoding the protein of the present disclosure.

In one example, the nucleic acid is included in an expression construct in which the nucleic acid is operably linked to a promoter. Such an expression construct can be in a vector, e.g., a plasmid.

In examples of the disclosure directed to single polypeptide chain proteins, the expression construct may comprise a promoter linked to a nucleic acid encoding that polypeptide chain.

In examples directed to multiple polypeptide chains that form a protein, an expression construct comprises a nucleic acid encoding a polypeptide comprising, e.g., a $V_H$ operably linked to a promoter and a nucleic acid encoding a polypeptide comprising, e.g., a $V_L$ operably linked to a promoter.

In another example, the expression construct is a bi-cistronic expression construct, e.g., comprising the following operably linked components in 5' to 3' order:
(i) a promoter
(ii) a nucleic acid encoding a first polypeptide;
(iii) an internal ribosome entry site; and
(iv) a nucleic acid encoding a second polypeptide,
wherein the first polypeptide comprises a $V_H$ and the second polypeptide comprises a $V_L$, or vice versa.

The present disclosure also contemplates separate expression constructs one of which encodes a first polypeptide comprising a $V_H$ and another of which encodes a second polypeptide comprising a $V_L$. For example, the present disclosure also provides a composition comprising:
(i) a first expression construct comprising a nucleic acid encoding a polypeptide comprising a $V_H$ operably linked to a promoter; and
(ii) a second expression construct comprising a nucleic acid encoding a polypeptide comprising a $V_L$ operably linked to a promoter.

The present disclosure also provides an isolated or recombinant cell expressing a protein of the disclosure.

In one example, the cell comprises the expression construct of the disclosure or:
(i) a first expression construct comprising a nucleic acid encoding a polypeptide comprising a $V_H$ operably linked to a promoter; and
(ii) a second expression construct comprising a nucleic acid encoding a polypeptide comprising a $V_L$ operably linked to a promoter.

Examples of cells of the present disclosure include bacterial cells, yeast cells, insect cells or mammalian cells.

The present disclosure additionally provides methods for producing a protein or antibody of the disclosure. For example, such a method involves maintaining the expression construct(s) of the disclosure under conditions sufficient for the protein to be produced.

In one example, a method for producing a protein or antibody of the disclosure comprises culturing the cell of the disclosure under conditions sufficient for the protein or antibody to be produced and, optionally, secreted.

In one example, the method for producing a protein of the disclosure additionally comprises isolating the protein and, optionally, formulating the protein or antibody into a pharmaceutical composition.

The present disclosure additionally provides a composition comprising a protein of the disclosure and a pharmaceutically acceptable carrier.

The present disclosure additionally provides a method of inhibiting complement activity in a subject, the method comprising administering a protein of the disclosure or a composition of the disclosure to the subject.

The present disclosure additionally provides a method of treating or preventing a complement-mediated disorder in a subject, the method comprising administering a protein of the disclosure or a composition of the disclosure to the subject.

The present disclosure additionally provides a protein of the disclosure for use in treating or preventing a complement-mediated disorder in a subject.

The present disclosure additionally provides use of a protein of the disclosure in the manufacture of a medicament for the treatment or prevention of a complement-mediated disorder.

In one example, the subject suffers from a complement-mediated disorder. In one example, the subject has been diagnosed as suffering from a complement-mediated disorder. In one example, the subject is receiving treatment for a complement-mediated disorder.

In one example of any method described herein, the protein or composition comprising the protein of the present disclosure is administered before or after the development of a complement-mediated disorder. In one example of any method described herein, the protein or composition comprising the protein of the present disclosure is administered before the development of the complement-mediated disorder. In one example of any method described herein, the protein or composition comprising the protein of the present disclosure is administered after the development of the complement-mediated disorder.

In one example, the subject is at risk of developing a complement-mediated disorder.

In one example, the protein or composition comprising the protein is administered before or after the onset of symptoms of a complement-mediated disorder. In one example, the protein or composition comprising the protein is administered before the onset of symptoms of a complement-mediated disorder. In one example, the protein or composition comprising the protein is administered after the onset of symptoms of a complement-mediated disorder. In one example, the protein or composition comprising the protein of the present disclosure is administered at a dose that alleviates or reduces one or more of the symptoms of a complement-mediated disorder. Symptoms of complement-mediated disorders are described herein.

In one example, the complement-mediated disorder is caused by primary dysregulation of the complement system, an autoimmune disorder, an acute injury and/or an inflammatory condition. In some examples, the complement-mediated disorder is a chronic disorder. In some examples, the complement-mediated disorder is an acute disorder.

In some examples, the complement-mediated disorder is selected from the group consisting of hereditary angioedema, paroxysmal nocturnal haemoglobinuria (PNH), atypical haemolytic uraemic syndrome (aHUS), thrombocytopenia purpura (TTP), thrombotic microangiopathy, C3 glomerulopathy, membranoproliferative glomerulonephritis (including anti-Thy 1 glomerulonephritis, anti-conA diffuse proliferative glomerulonephritis and/or passive heymann nephritis), transplant rejection (including lung transplant (including Graft salvage or antibody mediated rejection) and/or renal transplant (including antibody mediated rejection), neuromyelitis optica, multiple sclerosis, Guillain-Barré syndrome, myasthenia gravis (including autoimmune myasthenia gravis, demyelinating allergic encephalomyelitis, IgG immune complex alveolitis, reverse passive arthus reaction), lupus nephritis (including acute lupus nephritis or chronic lupus nephritis), systemic lupus erythematosus (SLE), IgA nephropathy, rheumatoid arthritis, Crohn's disease, ulcerative colitis, autoimmune haemolytic anemia, *pemphigus* (including *pemphigus vulgaris*), pemphigoid (including bullous pemphigoid), anti-phospholipid syndrome, polytrauma, neurotrauma, haemodialysis, post-infection HUS, macular degeneration, uveitis, ANCA-associated vasculitis, atherosclerosis, mood disorders, asthma, chronic obstructive pulmonary disease (COPD), chronic inflammatory demyelinating polyneuropathy (CIDP), anaphylaxis, sepsis, cerebral malaria, psoriatic arthropathy, dermatomyositis, osteoarthritis, dementia, glaucoma, diabetic angiopathy, myocardial infarction, ischemic stroke (with or without reperfusion), haemorrhagic stroke, post-bypass surgery, anti-glomerular basement membrane (GBM) nephritis (or Goodpasture's syndrome), autoimmune epilepsy, dermatitis herpetiformis, eosinophilic granulomatosis with polyangiitis (EGPA; or Churg-Strauss syndrome), traumatic brain injury, somatic trauma, hidradenitis suppurativa, Sjögren's syndrome, Sjögren's syndrome vasculitis, trauma (including glycogen induced peritonitis, thermal trauma, nerve crush and/or closed head injury), ischemia reperfusion injury (IRI; including myocardial IRI, intestinal IRI, liver IRI and/or pancreatic IRI) and acute respiratory distress syndrome (or acute lung injury).

In one example, the complement-mediated disorder is selected from the group consisting of transplant rejection (e.g., antibody mediated rejection), ischemia reperfusion injury before, during or after transplantation (including lung transplant and/or renal transplant), delayed graft function (including lung transplant and/or renal transplant), neuromyelitis optica, myasthenia gravis, a glomerular pathology, lupus nephritis, IgA nephropathy, bullous pemphigoid, anti-phospholipid syndrome, uveitis, a neurological disorder, Parkinson's disease, Huntington's disease, cerebral infarction, motor neuron disease, autoimmune haemolytic anemia, ANCA-associated vasculitis, chronic inflammatory demyelinating polyneuropathy (CIDP) and anti-glomerular basement membrane (GBM) nephritis. In one example, the subject has a condition requiring prophylactic treatment.

In one example, the complement-mediated disorder is selected from the group consisting of transplant rejection (including delayed graft function, graft salvage and antibody mediated rejection), a nephropathy, ischemia-reperfusion injury, neuromyelitis optica, myasthenia gravis, a glomerular pathology, lupus nephritis (acute and chronic), IgA nephropathy, bullous pemphigoid, anti-phospholipid syndrome, uveitis, a neurological disorder, Parkinson's disease, Huntington's disease, cerebral infarction, motor neuron disease, autoimmune haemolytic anemia, ANCA-associated vasculitis chronic inflammatory demyelinating polyneuropathy, ischemic stroke (with and without reperfusion), traumatic brain injury, somatic trauma and anti-glomerular basement membrane (GBM) nephritis.

In one example, the complement-mediated disorder is associated with an organ transplant (e.g., transplant rejection). In one example, the organ transplant is a solid organ transplant.

In one example, the complement-mediated disorder is transplant rejection (e.g., antibody mediated rejection). In one example, the transplant is a solid organ transplant.

In one example, the complement-mediated disorder is ischemia reperfusion injury before, during or after transplantation (including lung transplant and/or renal transplant). In one example, the transplantation is a solid organ transplantation.

In one example, the complement-mediated disorder is delayed graft function (including lung transplant and/or renal transplant). In one example, the delayed graft function is associated with a solid organ transplant.

In one example, the complement-mediated disorder is neuromyelitis optica.

In one example, the complement-mediated disorder is myasthenia gravis. For example, the myasthenia gravis is autoimmune myasthenia gravis, demyelinating allergic encephalomyelitis, IgG immune complex alveolitis or reverse passive arthus reaction.

In one example, the complement-mediated disorder is a glomerular pathology.

In one example, the complement-mediated disorder is lupus nephritis. For example, the lupus nephritis is acute lupus nephritis or chronic lupus nephritis.

In one example, the complement-mediated disorder is systemic lupus erythematosus (SLE).

In one example, the complement-mediated disorder is IgA nephropathy.

In one example, the complement-mediated disorder is pemphigoid. For example, the pemphigoid is bullous pemphigoid.

In one example, the complement-mediated disorder is anti-phospholipid syndrome.

In one example, the complement-mediated disorder is uveitis.

In one example, the complement-mediated disorder is a neurological disorder.

In one example, the complement-mediated disorder is Parkinson's disease.

In one example, the complement-mediated disorder is Huntington's disease.

In one example, the complement-mediated disorder is cerebral infarction.

In one example, the complement-mediated disorder is motor neuron disease.

In one example, the complement-mediated disorder is autoimmune haemolytic anemia.

In one example, the complement-mediated disorder is ANCA-associated vasculitis.

In one example, the complement-mediated disorder is chronic inflammatory demyelinating polyneuropathy.

In one example, the complement-mediated disorder is hereditary angioedema.

In one example, the complement-mediated disorder is paroxysmal nocturnal haemoglobinuria (PNH).

In one example, the complement-mediated disorder is atypical haemolytic uraemic syndrome (aHUS).

In one example, the complement-mediated disorder is thrombocytopenic purpura (TTP).

In one example, the complement-mediated disorder is thrombotic microangiopathy.

In one example, the complement-mediated disorder is C3 glomerulopathy.

In one example, the complement-mediated disorder is membranoproliferative glomerulonephritis. For example, the glomerulonephritis is anti-Thy 1 glomerulonephritis, anti-conA diffuse proliferative glomerulonephritis and/or passive heymann nephritis.

In one example, the complement-mediated disorder is transplant rejection. For example, the transplant is a solid organ transplant such as a lung transplant (including Graft salvage or antibody mediated rejection) and/or renal transplant (including antibody mediated rejection).

In one example, the complement-mediated disorder is multiple sclerosis.

In one example, the complement-mediated disorder is Guillain-Barré syndrome.

In one example, the complement-mediated disorder is rheumatoid arthritis.

In one example, the complement-mediated disorder is an inflammatory bowel disease. For example, the inflammatory bowel disease is Crohn's disease or ulcerative colitis.

In one example, the complement mediate disorder is *pemphigus*. For example, the *pemphigus* is *pemphigus vulgaris*.

In one example, the complement-mediated disorder is polytrauma.

In one example, the complement-mediated disorder is neurotrauma.

In one example, the complement-mediated disorder is haemodialysis.

In one example, the complement-mediated disorder is post-infection HUS.

In one example, the complement-mediated disorder is macular degeneration.

In one example, the complement-mediated disorder is atherosclerosis.

In one example, the complement-mediated disorder is a mood disorder.

In one example, the complement-mediated disorder is asthma.

In one example, the complement-mediated disorder is chronic obstructive pulmonary disease (COPD).

In one example, the complement-mediated disorder is chronic inflammatory demyelinating polyneuropathy (CIDP).

In one example, the complement-mediated disorder is anaphylaxis.

In one example, the complement-mediated disorder is sepsis.

In one example, the complement-mediated disorder is cerebral malaria.

In one example, the complement-mediated disorder is psoriatic arthropathy.

In one example, the complement-mediated disorder is dermatomyositis.

In one example, the complement-mediated disorder is osteoarthritis.

In one example, the complement-mediated disorder is dementia.

In one example, the complement-mediated disorder is glaucoma.

In one example, the complement-mediated disorder is diabetic angiopathy.

In one example, the complement-mediated disorder is myocarditis.

In one example, the complement-mediated disorder is myocardial infarction.

In one example, the complement-mediated disorder is stroke. For example, the stroke is ischemic stroke (with or without reperfusion). In another example, the stroke is haemorrhagic stroke.

In one example, the complement-mediated disorder is post-bypass surgery.

In one example, the complement-mediated disorder is anti-glomerular basement membrane (GBM) nephritis (or Goodpasture's syndrome).

In one example, the complement-mediated disorder is autoimmune epilepsy.

In one example, the complement-mediated disorder is dermatitis herpetiformis.

In one example, the complement-mediated disorder is eosinophilic granulomatosis with polyangiitis (EGPA; or Churg-Strauss syndrome).

In one example, the complement-mediated disorder is traumatic brain injury.

In one example, the complement-mediated disorder is trauma. For example, the trauma is somatic trauma. In one example, the trauma is glycogen induced peritonitis. In another example, the trauma is thermal trauma. In a further example, the trauma is nerve crush and/or closed head injury.

In one example, the complement-mediated disorder is hidradenitis suppurativa.

In one example, the complement-mediated disorder is Sjögren's syndrome. For example, the Sjögren's syndrome is Sjögren's syndrome vasculitis.

In one example, the complement-mediated disorder is ischemia reperfusion injury (IRI). For example, the IRI is myocardial IRI, intestinal IRI, liver IRI and/or pancreatic IRI. In one example, the IRI is associated with a solid organ transplant.

In one example, the complement-mediated disorder is acute respiratory distress syndrome (or acute lung injury).

In one example, the complement-mediated disorder is a fibrotic disease. In one example, the complement-mediated disorder is an interstitial lung disease (ILD).

In one example, the protein or composition comprising the protein of the present disclosure is administered to the subject in an amount to reduce the severity of the complement-mediated disorder in the subject.

In one example of any method described herein, the subject is a mammal, for example a primate such as a human.

Methods of treatment described herein can additionally comprise administering a further compound to reduce, treat or prevent the effect of the complement-mediated disorder.

The present disclosure also provides a method for detecting C2 or a cell expressing same in a sample, the method comprising contacting the sample with a protein as described herein according to any example such that a complex forms and detecting the complex, wherein detection of the complex is indicative of C2 or a cell expressing C2 in the sample.

The present disclosure also provides a method for diagnosing or prognosing a complement-mediated disorder, the method comprising performing a method as described herein according to any example to detect C2 or a cell expressing same, wherein detection of the C2 or cell expressing same is diagnostic or prognostic of the disorder.

The present disclosure also provides a kit comprising a protein as described herein according to any example packaged with instructions for use in a method as described herein. Optionally, the kit additionally comprises a further therapeutically active compound or drug.

Any example provided herein shall be taken to apply mutatis mutandis to any other example unless specifically stated otherwise. For instance, as the skilled person would understand, examples of proteins of the disclosure equally apply to the methods, compositions and kits of the disclosure, and vice versa.

KEY TO SEQUENCE LISTING

SEQ ID NO: 1—Human C2 amino acid sequence
SEQ ID NO: 2—RF16-226 and RF16-226G VH amino acid sequence
SEQ ID NO: 3—RF16-214 and RF16-214G VH amino acid sequence
SEQ ID NO: 4—RF16-242G VH amino acid sequence
SEQ ID NO: 5—RF16-242 VH amino acid sequence
SEQ ID NO: 6—RF16-226G VL amino acid sequence
SEQ ID NO: 7—RF16-214G VL amino acid sequence
SEQ ID NO: 8—RF16-242G VL amino acid sequence
SEQ ID NO: 9—RF16-226 VL amino acid sequence
SEQ ID NO: 10—RF16-214 VL amino acid sequence
SEQ ID NO: 11—RF16-242 VL amino acid sequence
SEQ ID NO: 12—RF16-226 and RF16-226G HCDR1 amino acid sequence
SEQ ID NO: 13—RF16-214 and RF16-214G HCDR1 amino acid sequence
SEQ ID NO: 14—RF16-242 and RF16-242G HCDR1 amino acid sequence
SEQ ID NO: 15—RF16-226 and RF16-226G HCDR2 amino acid sequence
SEQ ID NO: 16—RF16-214 and RF16-214G HCDR2 amino acid sequence
SEQ ID NO: 17—RF16-242 and RF16-242G HCDR2 amino acid sequence
SEQ ID NO: 18—RF16-226 and RF16-226G HCDR3 amino acid sequence

SEQ ID NO: 19—RF16-214 and RF16-214G HCDR3 amino acid sequence
SEQ ID NO: 20—RF16-242 and RF16-242G HCDR3 amino acid sequence
SEQ ID NO: 21—RF16-226 and RF16-226G LCDR1 amino acid sequence
SEQ ID NO: 22—RF16-214 and RF16-214G LCDR1 amino acid sequence
SEQ ID NO: 23—RF16-242 and RF16-242G LCDR1 amino acid sequence
SEQ ID NO: 24—RF16-226 and RF16-226G LCDR2 amino acid sequence
SEQ ID NO: 25—RF16-214 and RF16-214G LCDR2 amino acid sequence
SEQ ID NO: 26—RF16-242 and RF16-242G LCDR2 amino acid sequence
SEQ ID NO: 27—RF16-226 and RF16-226G LCDR3 amino acid sequence
SEQ ID NO: 28—RF16-214 and RF16-214G LCDR3 amino acid sequence
SEQ ID NO: 29—RF16-242 and RF16-242G LCDR3 amino acid sequence
SEQ ID NO: 30—RF16-226 and RF16-226G heavy chain amino acid sequence
SEQ ID NO: 31—RF16-214 and RF16-214G heavy chain amino acid sequence
SEQ ID NO: 32—RF16-242G heavy chain amino acid sequence
SEQ ID NO: 33—RF16-242 heavy chain amino acid sequence
SEQ ID NO: 34—RF16-226G light chain amino acid sequence
SEQ ID NO: 35—RF16-214G light chain amino acid sequence
SEQ ID NO: 36—RF16-242G light chain amino acid sequence
SEQ ID NO: 37—RF16-226 light chain amino acid sequence
SEQ ID NO: 38—RF16-214 light chain amino acid sequence
SEQ ID NO: 39—RF16-242 light chain amino acid sequence
SEQ ID NO: 40—HCDR1 consensus amino acid sequence based on RF16-226, RF16-214, and RF16-242
SEQ ID NO: 41—HCDR2 consensus amino acid sequence based on RF16-226, RF16-214, and RF16-242
SEQ ID NO: 42—HCDR3 consensus amino acid sequence based on RF16-226, RF16-214, and RF16-242
SEQ ID NO: 43—LCDR1 consensus amino acid sequence based on RF16-226, RF16-214, and RF16-242
SEQ ID NO: 44—LCDR2 consensus amino acid sequence based on RF16-226, RF16-214, and RF16-242
SEQ ID NO: 45—LCDR3 consensus amino acid sequence based on RF16-226, RF16-214, and RF16-242
SEQ ID NO: 46—RF16-191 VH amino acid sequence
SEQ ID NO: 47—RF16-203 VH amino acid sequence
SEQ ID NO: 48—RF16-191G VH amino acid sequence
SEQ ID NO: 49—RF16-203G VH amino acid sequence
SEQ ID NO: 50—RF16-191 VL amino acid sequence
SEQ ID NO: 51—RF16-203 VL amino acid sequence
SEQ ID NO: 52—RF16-191G VL amino acid sequence
SEQ ID NO: 53—RF16-203G VL amino acid sequence
SEQ ID NO: 54—RF16-191 and RF16-191G HCDR1 amino acid sequence
SEQ ID NO: 55—RF16-191 and RF16-191G HCDR2 amino acid sequence SEQ ID NO: 56—RF16-191 and RF16-191G HCDR3 amino acid sequence SEQ ID NO: 57—RF16-191 and RF16-191G LCDR1 amino acid sequence SEQ ID NO: 58—RF16-191 and RF16-191G LCDR2 amino acid sequence SEQ ID NO: 59—RF16-191 and RF16-191G LCDR3 amino acid sequence SEQ ID NO: 60—RF16-203 and RF16-203G HCDR1 amino acid sequence SEQ ID NO: 61—RF16-203 and RF16-203G HCDR2 amino acid sequence SEQ ID NO: 62—RF16-203 and RF16-203G HCDR3 amino acid sequence SEQ ID NO: 63—RF16-203 and RF16-203G LCDR1 amino acid sequence SEQ ID NO: 64—RF16-203 and RF16-203G LCDR2 amino acid sequence SEQ ID NO: 65—RF16-203 and RF16-203G LCDR3 amino acid sequence SEQ ID NO: 66—HCDR1 consensus amino acid sequence based on RF16-226, RF16-214, RF16-242, RF16-191, and RF16-203

SEQ ID NO: 67—HCDR2 consensus amino acid sequence based on RF16-226, RF16-214, RF16-242, RF16-191, and RF16-203

SEQ ID NO: 68—HCDR3 consensus amino acid sequence based on RF16-226, RF16-214, RF16-242, RF16-191, and RF16-203

SEQ ID NO: 69—LCDR1 consensus amino acid sequence based on RF16-226, RF16-214, RF16-242, RF16-191, and RF16-203

SEQ ID NO: 70—LCDR2 consensus amino acid sequence based on RF16-226, RF16-214, RF16-242, RF16-191, and RF16-203

SEQ ID NO: 71—LCDR3 consensus amino acid sequence based on RF16-226, RF16-214, RF16-242, RF16-191, and RF16-203

DETAILED DESCRIPTION

General

Figure 1:
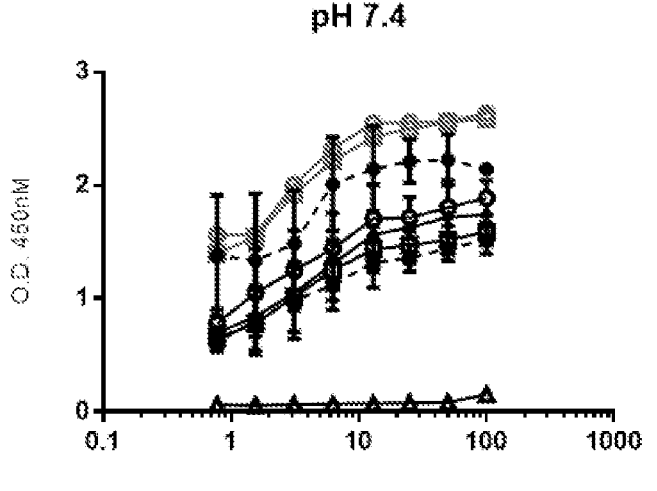
FIG. 1 is a graph illustrating binding properties of anti-C2 antibodies identified from a phage display library. The antibodies were tested at pH 5.5 and pH 7.4 for binding to human C2 in a titration ELISA. These titration experiments were done in duplicate. Human C2 protein was coated onto Maxisorp ELISA plates. Antibodies were serially diluted and added to the appropriate ELISA plate. Antibody binding was then detected with anti-Fab-HRP antibody and plates were developed using TMB/E substrate. The ELISA plates were read at absorbance 450 nm. The graph shows the absorbance at 450 nm plotted against anti-C2 antibody concentration.
Figure 1:
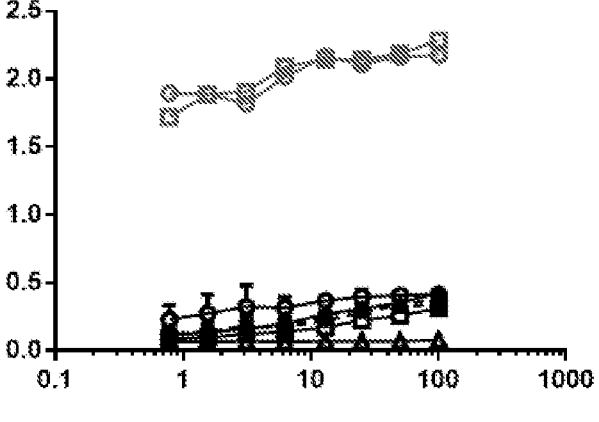

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T.A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat Sequences of Proteins of Immunological Interest, National Institutes of Health, Bethesda, Md., 1987 and 1991, Bork et al., *J Mol. Biol.* 242, 309-320, 1994, Chothia and Lesk *J. Mol Biol.* 196:901-917, 1987, Chothia et al. *Nature* 342, 877-883, 1989 and/or or Al-Lazikani et al., *J Mol Biol* 273, 927-948, 1997.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Selected Definitions

For the purposes of nomenclature only and not limitation an exemplary amino acid sequence of a human C2 is set out in NCBI Reference Sequence: NP_000054.2 (and set out in SEQ ID NO: 1). The sequence of cynomolgus monkey C2 can be determined using sequences provided herein and/or in publically available databases and/or determined using standard techniques (e.g., as described in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989))

Reference to "C2" herein is a reference to human C2. Reference herein to C2 includes native forms of C2, and mutant forms thereof.

The term "isolated protein" or "isolated polypeptide" is a protein or polypeptide that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, e.g., at least about 70% or 75% or 80% or 85% or 90% or 95% or 96% or 97% or 98% or 99% free of contaminating agents.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody antigen binding domain. Similarly, if nucleic acid encoding the protein is isolated and expressed using recombinant means, the resulting protein is a recombinant protein comprising an antibody antigen binding domain. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical linker or a disulphide bond, for example. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

As used herein, the term "antigen binding site" shall be taken to mean a structure formed by a protein that is capable of binding or specifically binding to an antigen. The antigen binding site need not be a series of contiguous amino acids, or even amino acids in a single polypeptide chain. For example, in a Fv produced from two different polypeptide chains the antigen binding site is made up of a series of amino acids of a $V_L$ and a $V_H$ that interact with the antigen and that are generally, however not always in the one or more of the CDRs in each variable region. In some examples, an antigen binding site comprises a $V_H$ or a $V_L$ or a Fv.

The skilled artisan will be aware that an "antibody" is generally considered to be a protein that comprises a variable region made up of a plurality of polypeptide chains, e.g., a polypeptide comprising a $V_L$ and a polypeptide comprising a $V_H$. An antibody also generally comprises constant domains, some of which can be arranged into a constant region, which includes a constant fragment or fragment crystallizable (Fc) region, in the case of a heavy chain. A $V_H$ and a $V_L$ interact to form a Fv comprising an antigen binding site that is capable of specifically binding to one or a few closely related antigens. Generally, a light chain from mammals is either a k light chain or a λ light chain and a heavy chain from mammals is α, δ, ε, γ, or μ. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. The term "antibody" also encompasses humanized antibodies, primatized antibodies, human antibodies and chimeric antibodies.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and includes amino acid sequences of complementarity determining regions (CDRs); i.e., CDR1, CDR2, and CDR3, and framework regions (FRs). Exemplary variable regions comprise three or four FRs (e.g., FR1, FR2, FR3 and optionally FR4) together with three CDRs. In the case of a protein derived from an IgNAR, the protein may lack a CDR2. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are necessary for antigen binding. Each variable region typically has three CDR regions identified as CDR1, CDR2 and CDR3. The amino acid positions assigned to CDRs and FRs can be defined according to Kabat *Sequences of Proteins of Immunological Interest*, National Institutes of Health, Bethesda, Md., 1987 and 1991 or other numbering systems in the performance of this disclosure, e.g., the canonical numbering system of Chothia and Lesk *J. Mol Biol.* 196:901-917, 1987; Chothia et al. *Nature* 342, 877-883, 1989; and/or Al-Lazikani et al., *J Mol Biol* 273: 927-948, 1997; the IMGT numbering system of Lefranc et al., *Devel. And Compar. Immunol.*, 27:55-77, 2003; or the AHO numbering system of Honnegher and Plükthun *J. Mol. Biol.*, 309:657-670, 2001. For example, according to the numbering system of Kabat, $V_H$ framework regions (FRs) and CDRs are positioned as follows: residues 1-30 (FR1), 31-35 (CDR1), 36:49 (FR2), 50-65 (CDR2), 66-94 (FR3), 95-102 (CDR3) and 103-113 (FR4). According to the numbering system of Kabat, $V_L$ FRs and CDRs are positioned as follows: residues 1-23 (FR1), 24-34 (CDR1), 35-49 (FR2), 50-56 (CDR2), 57-88 (FR3), 89-97 (CDR3) and 98-107 (FR4). The present disclosure is not limited to FRs and CDRs as defined by the Kabat numbering system, but includes all numbering systems, including those discussed above. In one example, reference herein to a CDR (or a FR) is in respect of those regions according to the Kabat numbering system.

"Framework regions" (FRs) are those variable region residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore, an Fv of the disclosure (as well as any protein of the disclosure) may have multiple antigen binding sites which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "$Fab_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of a protein or an antigen binding site thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that a protein of the disclosure reacts or associates more frequently, more rapidly, with greater duration and/or with greater affinity with a particular antigen or cell expressing same than it does with alternative antigens or cells. For example, a protein binds to C2 with materially greater affinity (e.g., 20 fold or 40 fold or 60 fold or 80 fold to 100 fold or 150 fold or 200 fold) than it does to other complement components or to antigens commonly recognized by polyreactive natural antibodies (i.e., by naturally occurring antibodies known to bind a variety of antigens naturally found in humans). Generally, but not necessarily, reference to binding means specific binding, and each term shall be understood to provide explicit support for the other term.

As used herein, the term "does not detectably bind" shall be understood to mean that a protein, e.g., an antibody, binds to a candidate antigen at a level less than 10%, or 8% or 6% or 5% above background. The background can be the level of binding signal detected in the absence of the protein and/or in the presence of a negative control protein (e.g., an isotype control antibody) and/or the level of binding detected in the presence of a negative control antigen. The level of binding is detected using biosensor analysis (e.g. Biacore) in which the protein is immobilized and contacted with an antigen, or vice versa.

As used herein, the term "does not significantly bind" shall be understood to mean that the level of binding of a protein of the disclosure to a polypeptide is not statistically significantly higher than background, e.g., the level of binding signal detected in the absence of the protein and/or in the presence of a negative control protein (e.g., an isotype control antibody) and/or the level of binding detected in the presence of a negative control polypeptide. The level of binding is detected using biosensor analysis (e.g. Biacore) in which the protein is immobilized and contacted with an antigen, or vice versa.

For the purposes of clarification and as will be apparent to the skilled artisan based on the exemplified subject matter herein, reference to "affinity" herein is a reference to a level of binding which can be quantified using, for example, a dissociation constant ($K_D$). Generally, reference to a level of affinity of a protein described herein is a reference to the protein's $K_D$ for a particular antigen. Thus, as referred to herein, a protein that has an affinity for C2 of at least 15 nM, has a $K_D$ of at least 15 nM (15 nM or stronger), i.e., the numerical value of the dissociation constant is either 15 nM or lower (for example, 10 nM or 100 pM). In this regard, reference to a higher affinity is reference to $K_D$ having a lower numerical value and vice versa.

As used herein, the phrase "neutral pH" refers to the approximate pH of blood in a healthy human individual (i.e., about pH 7.0 to about pH 7.5). Similarly, the phrase "acidic pH" refers to the approximate pH of an endosome (i.e., about pH 4.5 to about pH 6.5). In some examples, the acidic pH is the pH of an early endosome (i.e., about pH 5.5 to about pH 6.5). Also, any reference herein to an affinity at a particular pH, e.g., pH 6.0, encompasses an affinity at a pH within 0.2 units of the recited pH. For example, a skilled person would appreciate that a protein that binds C2 with a higher affinity at pH 7.3 than at 6.0 would also bind to C2 with a higher affinity at pH 7.5 than at 5.8.

As used herein, phrases referring to "reduced binding" or "binding being at a lower level" or "lower affinity" in relation to an antigen will be understood to mean that an antibody binds to an antigen (e.g., an alanine point mutant of SEQ ID NO:1 at any one of positions 443, 331, or 457) with an affinity at least about 1.1 fold, 1.5 fold, 2 fold, 3 fold, 4 fold, 5 fold, 10 fold, or 20 fold less than a control epitope or antigen (e.g. SEQ ID NO:1).

As used herein, the term "similar affinity" will be understood to mean that a protein of the present disclosure binds to two antigens (e.g., human C2 and cynomolgus monkey C2) with affinities that are within about 5 fold or less of one another, e.g., within about 4, 3, 2, or 1 fold of one another, such as, within about 1.5 fold of one another or the levels of binding are substantially identical, e.g., when the affinity is assessed by immobilizing the two antigens (e.g., human C2 and cynomolgus monkey C2) and contacting the immobilized proteins with a protein of the disclosure.

An "$IC_{50}$ of at least about" will be understood to mean that the $IC_{50}$ is equal to the recited value or greater (i.e., the numerical value recited as the $IC_{50}$ is lower), i.e., an $IC_{50}$ of 2 nM is greater than an $IC_{50}$ of 3 nM and vice versa.

As used herein, the term "epitope" (syn. "antigenic determinant") shall be understood to mean a region of C2 to which a protein of the disclosure binds. This term is not necessarily limited to the specific residues or structure to which the protein makes contact. For example, this term includes the region spanning amino acids contacted by the protein and/or 5-10 or 2-5 or 1-3 amino acids outside of this region. In some examples, the epitope comprises a series of discontinuous amino acids that are positioned close to one another when C2 is folded, i.e., a "conformational epitope". The skilled artisan will also be aware that the term "epitope" is not limited to peptides or polypeptides. For example, the term "epitope" includes chemically active surface groupings of molecules such as sugar side chains, phosphoryl side chains, or sulfonyl side chains, and, in certain examples, may have specific three dimensional structural characteristics, and/or specific charge characteristics.

The term "competitively inhibits" shall be understood to mean that a protein of the disclosure (or an antigen binding site thereof) reduces or prevents binding of a recited antibody or protein to C2. This may be due to the protein (or antigen binding site) and antibody binding to the same or an overlapping epitope. It will be apparent from the foregoing that the protein need not completely inhibit binding of the antibody, rather it need only reduce binding by a statistically significant amount, for example, by at least about 10% or 20% or 30% or 40% or 50% or 60% or 70% or 80% or 90% or 95%. Preferably, the protein reduces binding of the antibody by at least about 30%, more preferably by at least about 50%, more preferably, by at least about 70%, still more preferably by at least about 75%, even more preferably, by at least about 80% or 85% and even more preferably, by at least about 90%. Methods for determining competitive inhibition of binding are known in the art and/or described herein. For example, the antibody is exposed to C2 either in the presence or absence of the protein. If less antibody binds in the presence of the protein than in the absence of the protein, the protein is considered to competitively inhibit binding of the antibody. In one example, the competitive inhibition is not due to steric hindrance.

"Overlapping" in the context of two epitopes shall be taken to mean that two epitopes share a sufficient number of amino acid residues to permit a protein (or antigen binding site thereof) that binds to one epitope to competitively inhibit the binding of a protein (or antigen binding site) that binds to the other epitope. For example, the "overlapping" epitopes share at least 1 or 2 or 3 or 4 or 5 or 6 or 7 or 8 or 9 or 20 amino acids.

As used herein, the term "disorder" refers to a disruption of or interference with normal function, and is not to be limited to any specific disorder, and will include diseases or conditions.

As used herein, a "complement-mediated disorder" refers to any disorder that is caused by or associated with complement activity (e.g., excess complement activity), an excess of complement (e.g., C2) or cells expressing C2. The skilled artisan will be readily able to determine such conditions. In this regard, in some examples the condition is an inflammatory condition, an autoimmune condition or transplant rejection.

As used herein, the terms "preventing", "prevent" or "prevention" include administering a protein of the disclosure to thereby stop or hinder the development of at least one symptom of a disorder.

As used herein, the terms "treating", "treat" or "treatment" include administering a protein described herein to thereby reduce or eliminate at least one symptom of a specified disease or disorder.

As used herein, the term "subject" shall be taken to mean any animal including humans, for example a mammal.

Exemplary subjects include but are not limited to humans and non-human primates. For example, the subject is a human.

Antibodies

In one example, a protein as described herein according to any example is an antibody or a fragment thereof.

Methods for generating antibodies are known in the art and/or described in Harlow and Lane (editors) Antibodies: A Laboratory Manual, Cold Spring Harbor Laboratory, (1988). Generally, in such methods C2 or a region thereof (e.g., an extracellular domain) or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mabs).

Monoclonal antibodies are one exemplary form of antibody contemplated by the present disclosure. The term "monoclonal antibody" or "mAb" refers to a homogeneous antibody population capable of binding to the same antigen(s), for example, to the same epitope within the antigen. This term is not intended to be limited as regards to the source of the antibody or the manner in which it is made.

For the production of mAbs any one of a number of known techniques may be used, such as, for example, the procedure exemplified in U.S. Pat. No. 4,196,265 or Harlow and Lane (1988), supra.

For example, a suitable animal is immunized with an immunogen under conditions sufficient to stimulate antibody producing cells. Rodents such as rabbits, mice and rats are exemplary animals. Mice genetically-engineered to express human antibodies and, for example, do not express murine antibodies, can also be used to generate an antibody of the present disclosure (e.g., as described in WO2002/066630).

Following immunization, somatic cells with the potential for producing antibodies, specifically B lymphocytes (B cells), are selected for use in the mAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen.

Hybrids are amplified by culture in a selective medium comprising an agent that blocks the de novo synthesis of nucleotides in the tissue culture media. Exemplary agents are aminopterin, methotrexate and azaserine.

The amplified hybridomas are subjected to a functional selection for antibody specificity and/or titer, such as, for example, by flow cytometry and/or immunohistochemstry and/or immunoassay (e.g. radioimmunoassay, enzyme immunoassay, cytotoxicity assay, plaque assay, dot immunoassay, and the like).

Alternatively, ABL-MYC technology (NeoClone, Madison WI 53713, USA) is used to produce cell lines secreting MAbs (e.g., as described in Largaespada et al, *J. Immunol. Methods.* 197:85-95, 1996).

Antibodies can also be produced or isolated by screening a display library, e.g., a phage display library, e.g., as described in U.S. Pat. No. 6,300,064 and/or U.S. Pat. No. 5,885,793. For example, the present inventors have isolated fully human antibodies from a phage display library.

In another example, a phage display library is screened or an animal is immunized with C2, or a fragment thereof, and identified proteins and/or antibodies are screened to identify those that are cross-reactive with C2 and/or the fragment thereof.

In a further example, C2, or a fragment thereof, is contacted with RF16-226G, RF16-214G, or RF16-242G. A phage display library is then brought into contact with C2 or the fragment thereof and phage expressing proteins that can compete with RF16-226G, RF16-214G, or RF16-242G for binding are selected.

In a still further example, a chimeric protein comprising, e.g., a mouse C2 in which an epitope of interest from human C2 is substituted for the corresponding mouse sequence. This chimeric protein is then used to immunize mice (which are less likely to induce an immune response against the mouse protein) and/or to screen a phage display library. The resulting antibodies/proteins are then screened to identify those that bind to human C2 (particularly at the epitope of interest) and not mouse C2.

The antibody of the present disclosure may be a synthetic antibody. For example, the antibody is a chimeric antibody, a humanized antibody, a human antibody or a de-immunized antibody.

Chimeric Antibodies

In one example, an antibody described herein is a chimeric antibody. The term "chimeric antibody" refers to antibodies in which a portion of the heavy and/or light chain is identical with or homologous to corresponding sequences in antibodies derived from a particular species (e.g., murine, such as mouse) or belonging to a particular antibody class or subclass, while the remainder of the chain(s) is identical with or homologous to corresponding sequences in antibodies derived from another species (e.g., primate, such as human) or belonging to another antibody class or subclass. Chimeric antibodies utilize non-human, e.g. rodent or rabbit, variable regions and human constant regions, in order to produce an antibody with predominantly human domains. Methods for producing chimeric antibodies are described in, e.g., U.S. Pat. Nos. 4,816,567; and 5,807,715.

Humanized and Human Antibodies

The proteins or antibodies of the present disclosure may be humanized or human.

The term "humanized antibody" shall be understood to refer to a subclass of chimeric antibodies having an antigen binding site or variable region derived from an antibody from a non-human species and the remaining antibody structure based upon the structure and/or sequence of a human antibody. In a humanized antibody, the antigen-binding site generally comprises the complementarity determining regions (CDRs) from the non-human antibody grafted onto appropriate FRs in the variable regions of a human antibody and the remaining regions from a human antibody. Antigen binding sites may be wild-type (i.e., identical to those of the non-human antibody) or modified by one or more amino acid substitutions. In some instances, FR residues of the human antibody are replaced by corresponding non-human residues.

Methods for humanizing non-human antibodies or parts thereof (e.g., variable regions) are known in the art. Humanization can be performed following the method of U.S. Pat. No. 5,225,539, or 5,585,089. Other methods for humanizing an antibody are not excluded.

The term "human antibody" as used herein refers to antibodies having variable regions (e.g. $V_H$, $V_L$) and, optionally constant regions derived from or corresponding to sequences found in humans, e.g. in the human germline or somatic cells. The "human" antibodies can include amino acid residues not encoded by human sequences, e.g. mutations introduced by random or site directed mutations in vitro (in particular mutations which involve conservative substitutions or mutations in a small number of residues of the antibody, e.g. in 1, 2, 3, 4, 5 or 6 of the residues of the antibody, e.g. in 1, 2, 3, 4, 5 or 6 of the residues making up one or more of the CDRs of the antibody). These "human antibodies" do not actually need to be produced by a human, rather, they can be produced using recombinant means and/or isolated from a transgenic animal (e.g., mouse) comprising nucleic acid encoding human antibody constant and/or variable regions (e.g., as described above). Human antibodies can be produced using various techniques known in the art, including phage display libraries (e.g., as described in U.S. Pat. No. 5,885,793).

Human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope (e.g., as described in U.S. Pat. No. 5,565,332).

Exemplary human antibodies are described herein and include RF16-226G, RF16-214G, and RF16-242G and/or variable regions thereof. These human antibodies provide an advantage of reduced immunogenicity in a human compared to non-human antibodies.

Antibody Binding Domain Containing Proteins

Single-Domain Antibodies

In some examples, a protein of the disclosure is or comprises a single-domain antibody (which is used interchangeably with the term "domain antibody" or "dAb"). A single-domain antibody is a single polypeptide chain comprising all or a portion of the heavy chain variable region of an antibody. In certain examples, a single-domain antibody is a human single-domain antibody (Domantis, Inc., Waltham, MA; see, e.g., U.S. Pat. No. 6,248,516).

Diabodies, Triabodies, Tetrabodies

In some examples, a protein of the disclosure is or comprises a diabody, triabody, tetrabody or higher order protein complex such as those described in WO98/044001 and/or WO94/007921.

For example, a diabody is a protein comprising two associated polypeptide chains, each polypeptide chain comprising the structure $V_L$-X-$V_H$ Or $V_H$-X-$V_L$, wherein $V_L$ is an antibody light chain variable region, $V_H$ is an antibody heavy chain variable region, X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding site, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

Single Chain Fv (scFv)

The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favored linkers for a scFv.

The present disclosure also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv.

Alternatively, or in addition, the present disclosure encompasses a dimeric scFv, i.e., a protein comprising two scFv molecules linked by a non-covalent or covalent linkage, e.g., by a leucine zipper domain (e.g., derived from Fos or Jun). Alternatively, two scFvs are linked by a peptide linker of sufficient length to permit both scFvs to form and to bind to an antigen, e.g., as described in US20060263367.

Heavy Chain Antibodies

Heavy chain antibodies differ structurally from many other forms of antibodies, in so far as they comprise a heavy chain, but do not comprise a light chain. Accordingly, these antibodies are also referred to as "heavy chain only antibodies". Heavy chain antibodies are found in, for example, camelids and cartilaginous fish (also called IgNAR).

The variable regions present in naturally occurring heavy chain antibodies are generally referred to as "$V_{HH}$ domains" in camelid antibodies and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

A general description of heavy chain antibodies from camelids and the variable regions thereof and methods for their production and/or isolation and/or use is found inter alia in the following references WO94/04678, WO97/49805 and WO 97/49805.

A general description of heavy chain antibodies from cartilaginous fish and the variable regions thereof and methods for their production and/or isolation and/or use is found inter alia in WO2005/118629.

Other Antibodies and Antibody Fragments

The present disclosure also contemplates other antibodies and antibody fragments, such as:

(i) "key and hole" bispecific proteins as described in U.S. Pat. No. 5,731,168;

(ii) heteroconjugate proteins, e.g., as described in U.S. Pat. No. 4,676,980;

(iii) heteroconjugate proteins produced using a chemical cross-linker, e.g., as described in U.S. Pat. No. 4,676,980; and (iv) $Fab_3$ (e.g., as described in EP19930302894).

De-Immunized Antibodies and Proteins

The present disclosure also contemplates a de-immunized antibody or protein. De-immunized antibodies and proteins have one or more epitopes, e.g., B cell epitopes or T cell epitopes removed (i.e., mutated) to thereby reduce the likelihood that a mammal will raise an immune response against the antibody or protein. Methods for producing de-immunized antibodies and proteins are known in the art and described, for example, in WO00/34317, WO2004/108158 and WO2004/064724.

Methods for introducing suitable mutations and expressing and assaying the resulting protein will be apparent to the skilled artisan based on the description herein.

Mutations to Proteins

The present disclosure also contemplates mutant forms of a protein of the disclosure. In this regard, data presented herein indicate sites within a CDR of a protein of the disclosure that can be changed in addition to exemplary changes that can be made. The skilled person will understand that changes can additionally or alternatively be made within a FR of a variable region containing protein without inhibiting or significantly reducing its function in the context of the present disclosure. In this regard, amino acid substitutions may be introduced into a protein of the disclosure and the products screened for a desired activity, e.g., retained/improved antigen binding, decreased immunogenicity, or improved ADCC or CDC.

For example, such a mutant protein comprises one or more conservative amino acid substitutions compared to a sequence set forth herein. In some examples, the protein comprises 30 or fewer or 20 or fewer or 10 or fewer, e.g., 9 or 8 or 7 or 6 or 5 or 4 or 3 or 2 conservative amino acid substitutions. A "conservative amino acid substitution" is one in which the amino acid residue is replaced with an amino acid residue having a similar side chain and/or hydropathicity and/or hydrophilicity.

In one example, a mutant protein has only, or not more than, one or two or three or four or five or six conservative amino acid changes when compared to a naturally occurring protein. Details of conservative amino acid changes are provided below. As the skilled person would be aware, e.g., from the disclosure herein, such minor changes can reasonably be predicted not to alter the activity of the protein.

In some examples, the protein has no more than 3, no more than 2, or no more than 1 amino acid substitution in the CDR-L1, no more than 2 or no more than 1 amino acid substitutions in the CDR-L2, no more than 3, no more than 2, or no more than 1 amino acid substitution in the CDR-L3, no more than 2 or no more than 1 amino acid substitution in the CDR-H1, no more than 4, no more than 3, no more than 2, or no more than 1 amino acid substitution in the CDR-H2, and/or no more than 3, no more than 2, or no more than 1 amino acid substitution in the CDR-H3, relative to any one or more of the CDR amino acid sequences provided herein. In some examples, each CDR contains no more than one, two, three, or four amino acid substitutions. In some examples, the amino acid substitutions are conservative substitutions. In some examples, the binding agent comprises an amino acid substitution in a framework region. As a person skilled in the art would appreciate, routine site-directed or random mutagenesis techniques can be performed to alter the amino acid sequence of any one of the CDR or framework sequences provided herein in order to, for example, alter binding affinity (e.g., affinity maturation), reduce susceptibility to proteolysis or oxidation, or confer or modify other physicochemical or functional properties of the proteins.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Examples of conservative amino acid substitutions are provided below in Table 1.

TABLE 1

| Exemplary conservative amino acid changes | | |
|---|---|---|
| Original amino acid | Exemplary substitutions | Preferred substitutions |
| Ala | Val; Leu; Ile | Val |
| Arg | Lys; Gln; Asn | Lys |
| Asn | Gln; His; Asp, Lys; Arg | Gln |
| Asp | Glu; Asn | Glu |
| Cys | Ser; Ala | Ser |
| Gln | Asn; Glu | Asn |
| Glu | Asp;Gln | Asp |
| Gly | Ala | Ala |
| His | Asn; Gln; Lys; Arg | Arg |
| Ile | Leu; Val; Met; Ala; Phe; Norleucine | Leu |
| Leu | Norleucine; Ile; Val; Met; Ala; Phe | Ile |
| Lys | Arg; Gln; Asn | Arg |
| Met | Leu; Phe; Ile | Leu |
| Phe | Trp; Leu; Val; Ile; Ala; Tyr | Tyr |
| Pro | Ala | Ala |
| Ser | Thr | Thr |
| Thr | Val; Ser | Ser |
| Trp | Tyr; Phe | Tyr |
| Tyr | Trp; Phe; Thr; Ser | Phe |
| Val | Ile; Leu; Met; Phe; Ala; Norleucine | Leu |

The present disclosure also contemplates non-conservative amino acid changes (e.g., substitutions) in a protein of the present disclosure, e.g., in a CDR, such as CDR3. In one example, the protein comprises fewer than 6 or 5 or 4 or 3 or 2 or 1 non-conservative amino acid substitutions, e.g., in a CDR3, such as in a CDR3.

Routine techniques can be used to introduce amino acid substitutions in CDRs to, for example, improve binding affinity. Such substitutions may be made in CDR "hotspots," i.e., residues encoded by codons that undergo mutation at high frequency during the somatic maturation process (see, e.g., Chowdhury, Methods Mol. Biol. 207:179-196 (2008)), and/or residues that contact C2, with the resulting variant $V_H$ and/or $V_L$ being tested for binding affinity. Alternatively or additionally, affinity maturation may be performed. Affinity maturation by constructing and reselecting from secondary libraries has been described, e.g., in Hoogenboom et al., in Methods in Molecular Biology 178:1-37 (O'Brien et al., ed., Human Press, Totowa, NJ, (2001)). In some examples of affinity maturation, diversity is introduced into the variable region coding sequences chosen for maturation by any of a variety of methods (e.g., error-prone PCR, chain shuffling, or oligonucleotide-directed mutagenesis). A secondary library is then created. The library is then screened to identify any variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis, described below, or modeling. CDR-H3 and CDR-L3 in particular can be used for random mutagenesis and affinity maturation.

In certain examples, substitutions, insertions, or deletions may occur within one or more CDRs so long as such alterations do not substantially reduce the ability of the protein to bind to C2 in a pH-dependent manner. For example, conservative substitutions may be made in CDRs so long as the protein still binds to C2 with greater affinity at pH 7.3 than at pH 6.0. In some examples, the protein comprising the amino acid substitutions binds to C2 with a similar affinity to the protein without the substitutions. Such substitutions may, for example, be outside of antigen contacting residues in the CDRs. In some examples, the protein comprising the amino acid substitutions binds to C2 with a higher affinity than the protein without the substitutions. In some examples, the protein comprising the amino acid substitutions binds to C2 with a lower affinity than the protein without the substitutions. In certain examples, each CDR either is unaltered, or contains no more than one, two, three, or four amino acid substitutions. In some examples, the substitutions are conservative substitutions.

A useful method for identification of residues or regions of an antibody that may be targeted for mutagenesis is called "alanine scanning mutagenesis" as described by Cunningham, Science 244:1081-1085 (1989). In this method, a residue or group of target residues (e.g., charged residues such as Arg, Asp, His, Lys, and Glu) are identified and replaced by a neutral amino acid such as alanine to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex can be used to identify contact points between the antibody and antigen. Such contact residues and neighboring residues may be targeted or eliminated as candidates for substitution. Variants may be screened to determine whether they contain the desired properties.

Alternatively or additionally, amino acid substitutions may be introduced in order to alter the protein's pH-dependent binding capabilities. For example, amino acid substitutions can be introduced to increase the protein's affinity for C2 at pH 7.3 and/or to decrease its affinity for C2 at pH 6.0. As will be appreciated by a person skilled in the art, the ability of an amino acid substitution to affect pH sensitive binding requires the inserted residue to experience a change in pKa upon binding to C2. Thus, inclusion of ionizable residues (e.g., His, Arg, Lys) in the CDRs of proteins described herein may alter their pH-dependent binding capabilities. In this regard, such ionizable residues can alter the three dimensional structure of a protein upon protonation or deprotonation, leading to the shift in pKa. Techniques which are known in the art for altering pH-dependent binding include those described in US20110111406A1, WO2012044831, WO2017132259, and Murtaugh et al., Protein Science, 20:1619-1631 (2011). Therefore, in some examples, an amino acid in a CDR sequence provided herein is substituted with an ionizable residue. In some examples, the ionizable residue is histidine, arginine, lysine, aspartate, or glutamate. In some examples, the ionizable residue is histidine.

The present disclosure also contemplates one or more insertions or deletions compared to a sequence set forth herein. In some examples, the protein comprises 10 or fewer, e.g., 9 or 8 or 7 or 6 or 5 or 4 or 3 or 2 insertions and/or deletions.

Constant Regions

The present disclosure encompasses proteins described herein comprising a constant region of an antibody. This includes antigen binding fragments of an antibody fused to a Fc.

Sequences of constant regions useful for producing the proteins of the present disclosure may be obtained from a number of different sources. In some examples, the constant region or portion thereof of the protein is derived from a human antibody. The constant region or portion thereof may be derived from any antibody class, including IgM, IgG, IgD, IgA and IgE, and any antibody isotype, including IgG1, IgG2, IgG3 and IgG4. In one example, the constant region is human isotype IgG4 or a stabilized IgG4 constant region.

In one example, the Fc region of the constant region has a reduced ability to induce effector function, e.g., compared to a native or wild-type human IgG1 or IgG3 Fc region. In one example, the effector function is antibody-dependent cell-mediated cytotoxicity (ADCC) and/or antibody-dependent cell-mediated phagocytosis (ADCP) and/or complement-dependent cytotoxicity (CDC). Methods for assessing the level of effector function of an Fc region containing protein are known in the art and/or described herein.

In one example, the Fc region is an IgG4 Fc region (i.e., from an IgG4 constant region), e.g., a human IgG4 Fc region. Sequences of suitable IgG4 Fc regions will be apparent to the skilled person and/or available in publically available databases (e.g., available from National Center for Biotechnology Information).

In one example, the constant region is a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington DC United States Department of Health and Human Services, 1987 and/or 1991). This position corresponds to position 228 of the hinge region according to the EU numbering system (Kabat et al., Sequences of Proteins of Immunological Interest Washington DC United States Department of Health and Human Services, 2001 and Edelman et al., *Proc. Natl. Acad. USA,* 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Additional examples of stabilized IgG4 antibodies are antibodies in which arginine at position 409 in a heavy chain constant region of human IgG4 (according to the EU numbering system) is substituted with lysine, threonine, methionine, or leucine (e.g., as described in WO2006/033386). The Fc region of the constant region may additionally or alternatively comprise a residue selected from the group consisting of: alanine, valine, glycine, isoleucine and leucine at the position corresponding to 405 (according to the EU numbering system). Optionally, the hinge region comprises a proline at position 241 (i.e., a CPPC sequence) (as described above).

In another example, the Fc region is a region modified to have reduced effector function, i.e., a "non-immunostimulatory Fc region". For example, the Fc region is an IgG1 Fc region comprising a substitution at one or more positions selected from the group consisting of 268, 309, 330 and 331. In another example, the Fc region is an IgG1 Fc region comprising one or more of the following changes E233P, L234V, L235A and deletion of G236 and/or one or more of the following changes A327G, A330S and P331S (Armour et al., *Eur J Immunol.* 29:2613-2624, 1999; Shields et al., *J Biol Chem.* 276 (9): 6591-604, 2001). Additional examples of non-immunostimulatory Fc regions are described, for example, in Dall'Acqua et al., *J Immunol.* 177:1129-1138 2006; and/or Hezareh *J Virol;* 75:12161-12168, 2001).

In another example, the Fc region is a chimeric Fc region, e.g., comprising at least one $C_H2$ domain from an IgG4 antibody and at least one $C_H3$ domain from an IgG1 antibody, wherein the Fc region comprises a substitution at one or more amino acid positions selected from the group consisting of 240, 262, 264, 266, 297, 299, 307, 309, 323, 399, 409 and 427 (EU numbering) (e.g., as described in WO2010/085682). Exemplary substitutions include 240F, 262L, 264T, 266F, 297Q, 299A, 299K, 307P, 309K, 309M, 309P, 323F, 399S, and 427F.

Additional Modifications

The present disclosure also contemplates additional modifications to the protein that binds to C2.

For example, the protein of the disclosure may comprise one or more amino acid substitutions that increase the half-life of the protein. For example, the protein comprises a Fc region comprising one or more amino acid substitutions that increase the affinity of the Fc region for the neonatal Fc receptor (FcRn). For example, the Fc region has increased affinity for FcRn at lower pH, e.g., about pH 6.0, to facilitate Fc/FcRn binding in an endosome. In one example, the Fc region has increased affinity for FcRn at about pH 6 compared to its affinity at about pH 7.3, which facilitates the re-release of Fc into blood following cellular recycling. These amino acid substitutions are useful for extending the half life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

In some examples, the one or more amino acid substitutions are selected from M252Y, S254T, T256E, V308P, N286E, M428L, N434A, and N434Y according to the EU numbering system. In some examples, the protein comprises the following amino acid substitutions in its Fc region:
    (i) M252Y,
    (ii) N286E or V308P, and
    (iii) N434Y (according to the EU numbering system).

Protein Production

In one example, a protein described herein according to any example is produced using methods that are known in the art, e.g., by culturing a hybridoma under conditions sufficient to produce the protein.

Recombinant Expression

In another example, a protein described herein according to any example is recombinant.

In the case of a recombinant protein, nucleic acid encoding same can be cloned into expression constructs or vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary cells used for expressing a protein are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. No. 4,816,567 or 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding a protein (e.g., derived from the information provided herein), an enhancer element, a promoter, and a transcription termination sequence. The skilled artisan will be aware of suitable sequences for expression of a protein. Exemplary signal sequences include prokaryotic secretion signals (e.g., pelB, alkaline phosphatase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADHI promoter, the GALI promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the protein may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Isolation of Proteins

Methods for isolating a protein are known in the art and/or described herein.

Where a protein is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the protein, e.g., using continuous centrifugation.

The protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbor Laboratory, (1988).

The skilled artisan will also be aware that a protein can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Assaying Activity of a Protein

Binding to C2 and Mutants Thereof

Methods for assessing binding to a protein are known in the art, e.g., as described in Scopes (In: Protein purification: principles and practice, Third Edition, Springer Verlag, 1994). Such a method generally involves labeling the protein and contacting it with immobilized antigen or vice versa. Following washing to remove non-specific bound protein, the amount of label and, as a consequence, bound protein is detected. Of course, the protein can be immobilized and the antigen labeled. Panning-type assays can also be used. Alternatively, or additionally, surface plasmon resonance assays can be used. Thus, in one example, the affinity of a protein described herein is determined using a biosensor.

Optionally, the dissociation constant (Kd) of a protein for C2 is determined. The "Kd" or "$K_D$" or "Kd value" for a C2 binding protein is in one example measured by a radiolabeled or fluorescently-labeled C2 binding assay. This assay equilibrates the protein with a minimal concentration of labeled C2 in the presence of a titration series of unlabeled C2. Following washing to remove unbound C2, the amount of label is determined, which is indicative of the Kd of the protein.

According to another example the Kd is measured by using surface plasmon resonance assays, e.g., using BIAcore surface plasmon resonance (BIAcore, Inc., Piscataway, NJ) with immobilized C2 or vice versa. Thus, in one example, the affinity of a protein is determined using a biosensor (e.g., by surface plasmon resonance) in an assay in which the protein is immobilized and C2 is contacted with the immobilized protein.

Epitope Mapping

In another example, the epitope bound by a protein described herein is mapped. Epitope mapping methods will be apparent to the skilled artisan. For example, a series of overlapping peptides spanning the C2 sequence or a region thereof comprising an epitope of interest, e.g., peptides comprising 10-15 amino acids are produced. The protein is then contacted to each peptide and the peptide(s) to which it binds determined. This permits determination of peptide(s) comprising the epitope to which the protein binds. If multiple non-contiguous peptides are bound by the protein, the protein may bind a conformational epitope.

Alternatively, or in addition, as exemplified herein, amino acid residues within C2 are mutated, e.g., by alanine scanning mutagenesis, and mutations that reduce or prevent protein binding are determined. Any mutation that reduces or prevents binding of the protein is likely to be within the epitope bound by the protein.

A further method involves binding C2 or a region thereof to an immobilized protein of the present disclosure and digesting the resulting complex with proteases. Peptide that remains bound to the immobilized protein are then isolated and analyzed, e.g., using mass spectrometry, to determine their sequence.

A further method involves converting hydrogens in C2 or a region thereof to deutrons and binding the resulting protein to an immobilized protein of the present disclosure. The deutrons are then converted back to hydrogen, the C2 or region thereof isolated, digested with enzymes and analyzed, e.g., using mass spectrometry to identify those regions comprising deutrons, which would have been protected from conversion to hydrogen by the binding of a protein described herein.

Determining Competitive Binding

Assays for determining whether a protein competitively inhibits binding of an antibody described herein, such as RF16-226G, RF16-214G, RF16-242G, RF16-226, RF16-214, RF16-242, RF16-191, or RF16-203, will be apparent to the skilled artisan. For example, the antibody is conjugated to a detectable label, e.g., a fluorescent label or a radioactive label. The labeled antibody and the test protein are then mixed and contacted with C2 or a region thereof (e.g., a polypeptide comprising SEQ ID NO: 1) or a cell expressing same. The level of labeled antibody is then determined and compared to the level determined when the labeled antibody is contacted with C2, region or cells in the absence of the protein. If the level of labeled antibody is reduced in the presence of the test protein compared to the absence of the protein, the protein is considered to competitively inhibit binding of the antibody.

Optionally, the test protein is conjugated to a different label to the antibody. This alternate labeling permits detection of the level of binding of the test protein to C2 or the region thereof or the cell.

In another example, the protein is permitted to bind to C2 or a region thereof (e.g., a polypeptide comprising SEQ ID NO: 1) or a cell expressing same prior to contacting the C2, region or cell with the antibody. A reduction in the amount of bound antibody in the presence of the protein compared to in the absence of the protein indicates that the protein competitively inhibits the antibody binding to C2. A reciprocal assay can also be performed using labeled protein and first allowing the antibody to bind to C2. In this case, a reduced amount of labeled protein bound to C2 in the presence of the antibody compared to in the absence of the antibody indicates that the protein competitively inhibits binding of the antibody to C2.

Any of the foregoing assays can be performed with a mutant form of C2 and/or SEQ ID NO: 1 and/or a region of C2 to which an antibody described herein binds, e.g., as described above.

Measuring Inhibition of Complement Activity

In one example, complement activity is measured using an enzyme immunoassay (e.g., a Wieslab® complement assay kit). For example, complement inhibitory activity is determined using labelled antibodies specific for an antigen or an epitope produced during complement activation (e.g., C5b-9 or an epitope present in C5b-9). In one example, the wells of a microtitre plate are coated with specific activators of the classical, lectin or alternative pathway. In another example, a protein of the disclosure is incubated with normal human serum and appropriate assay diluent (i.e., a diluent comprising appropriate blocking components to ensure specific activation of the classical, lectin or alternative pathway) and added to microtitre plate wells coated with specific activators of the classical, lectin or alternative pathway and the amount of C5b-9 complex formed is detected using a specific alkaline phosphatase labelled antibody to the C5b-9. In one example, the amount of complement activation product (i.e., C5b-9) produced is proportional to the functional activity of the complement pathway. In one example, the half maximal inhibitor concentration (i.e., $IC_{50}$) is determined.

In another example, complement inhibitory activity is determined using a hemolysis assay (e.g., classical pathway (i.e., CH50) and alternative pathway (ApH50) inhibition assays). The CH50 assay is a method for measuring the total classical complement activity in serum. This test is a lytic assay, which uses antibody-sensitized erythrocytes as the activator of the classical complement pathway and human serum as complement source. The percent hemolysis can be determined, for example, using a spectrophotometer. The CH50 assay provides an indirect measure of terminal complement complex (TCC) formation, since the TCC themselves are directly responsible for the hemolysis that is measured. The assay is well known in the art. Briefly, to assess the inhibition of the classical complement pathway, pre-diluted human serum is pre-incubated in microassay wells, together with serially diluted protein of the disclosure. Next, antibody-sensitized erythrocytes (e.g., sheep erythrocytes sensitized with rabbit anti-sheep antibodies) are added. After centrifugation, free haemoglobin is measured in the supernatants, using a spectrophotometer. The decrease in free haemoglobin reflects the inhibition of TCC-mediated erythrocyte lysis. Inhibition of complement activity is then calculated relative to erythrocytes which were incubated with human serum only (100% lysis sample).

Complement inhibition can also be evaluated based on any methods known in the art, including for example, in vitro zymosan assays, assays for lysis of erythrocytes, antibody or immune complex activation assays, alternative pathway activation assays, and lectin pathway activation assays.

Determining Half Life

Some proteins encompassed by the present disclosure have an improved half-life, e.g., are modified to extend their half-life or are conjugated to a compound that extends their half-life. Methods for determining a protein with an improved half-life will be apparent to the skilled person. For example, the ability of a protein to bind to a neonatal Fc receptor (FcRn) is assessed. In this regard, increased binding affinity for FcRn increases the serum half-life of the protein (see for example, Kim et al., *Eur J Immunol.*, 24:2429, 1994).

The half-life of a protein of the disclosure can also be measured by pharmacokinetic studies, e.g., according to the method described by Kim et al, *Eur J of Immunol* 24:542, 1994. According to this method radiolabeled protein is injected intravenously into mice and its plasma concentration is periodically measured as a function of time, for example at 3 minutes to 72 hours after the injection. Alternatively, unlabelled protein of the disclosure can be injected and its plasma concentration periodically measured using an ELISA. The clearance curve thus obtained should be biphasic, that is, an alpha phase and beta phase. For the determination of the in vivo half-life of the protein, the clearance rate in beta-phase is calculated and compared with that of the wild type or unmodified protein.

Conditions to be Treated

The present disclosure provides, for example, a method of inhibiting complement activity in a subject comprising administering to the subject a protein of the present disclosure.

The present disclosure also provides a method of treating or preventing a complement-mediated disorder in a subject, the method comprising administering the protein or composition comprising the protein of the present disclosure to the subject.

In one example, the method comprises inhibiting complement activity in the classical pathway or the lectin pathway. For example, the method comprises administering a protein of the present disclosure to inhibit activation of the classical complement pathway. In another example, the method comprises administering a protein of the present disclosure to inhibit activation of the lectin complement pathway.

The complement-mediated disorder can be inherited or acquired.

In one example, the complement-mediated disorder is selected from the group consisting of transplant rejection (including delayed graft function, graft salvage and antibody mediated rejection), a nephropathy, ischemia-reperfusion injury, neuromyelitis optica, myasthenia gravis, a glomerular pathology, lupus nephritis (acute and chronic), IgA nephropathy, bullous pemphigoid, anti-phospholipid syndrome, uveitis, a neurological disorder, Parkinson's disease, Huntington's disease, cerebral infarction, motor neuron disease, autoimmune haemolytic anemia, ANCA-associated vasculitis, chronic inflammatory demyelinating polyneuropathy, ischemic stroke (with and without reperfusion), traumatic brain injury, somatic trauma and anti-glomerular basement membrane (GBM) nephritis.

In one example, the complement-mediated disorder is a primary dysregulation, such as a hereditary angioedema, paroxysmal nocturnal hemoglobinuria, atypical hemolytic uremic syndrome (aHUS), thrombotic thrombocytopenia purpura (TTP), thrombotic microangiopathy, C3 glomerulopathy, membranoproliferative glomerulonephritis or transplant rejection (including delayed graft function, graft salvage and antibody mediated rejection).

In one example, the complement-mediated disorder is an autoimmune condition, such as neuromyelitis optica, multiple sclerosis, myasthenia gravis, Guillain-Barre syndrome, myasthenia gravis, lupus nephritis (acute and chronic), IgA nephropathy, rheumatoid arthritis, Crohn's disease, ulcerative colitis, autoimmune hemolytic anemia, *pemphigus*, pemphigoid (including bullous, pemphigoid) chronic inflammatory demyelinating polyneuropathy (CIDP), anti-glomerular basement membrane (GBM) nephritis or anti-phospholipid syndrome.

In one example, the complement-mediated disorder is cold autoimmune hemolytic anemia (CAIHA), also known as cold agglutinin disease (CAD). In one example, complement-mediated disorder is warm antibody autoimmune hemolytic anemia (WAIHA).

In one example, the complement-mediated disorder is an acute injury, such as polytrauma, neurotrauma, hemodialysis, traumatic brain injury, somatic trauma or post infection HUS.

In one example, the complement-mediated disorder is an inflammatory condition such as macular degeneration, uveitis, ANCA-associated vasculitis, atherosclerosis, asthma, COPD, sepsis, acute respiratory distress syndrome, cerebral malaria, psoriatic arthropathy or dermatomyositis.

In one example, the complement-mediated disorder is a degenerative condition such as osteoarthritis, dementia, glaucoma, a neurological disorder, Parkinson's disease, Huntington's disease, motor neuron disease or diabetic angiopathy.

In one example, the complement-mediated disorder is an ischemia-reperfusion condition/injury, e.g., as occurs in organ transplantation, or post-surgery or following stroke or myocardial infarction.

In one example, the complement-mediated disorder is myocarditis.

In one example, the complement-mediated disorder is a fibrotic disease. In one example, the complement-mediated disorder is an interstitial lung disease (ILD). In one example, the ILD is idiopathic pulmonary fibrosis (IPF). In one example, the ILD is a non-IPF ILD. In one example, the ILD is a progressive fibrosing ILD. In one example, the ILD is a progressive fibrosing phenotype of non-IPF. Methods for diagnosis of a complement-mediated disorder will be readily apparent to the skilled person and include, for example, total serum class haemolytic complement (CH-50) test, alternative haemolytic complement (AP-50) test, screening for immune complex diseases, antinuclear serology to test for lupus, urinalysis and complete blood count (CBC).

In one example, the subject is at risk of developing a complement-mediated disorder. A subject is at risk if he or she has a higher risk of developing a complement-mediated disorder than a control population. The control population may include one or more subjects selected at random from the general population (e.g., matched by age, gender, race and/or ethnicity) who have not suffered from or have a family history of a complement-mediated disorder. A subject can be considered at risk for a complement-mediated disorder if a "risk factor" associated with a complement-mediated disorder is found to be associated with that subject. A risk factor can include any activity, trait, event or property associated with a given disorder, for example, through statistical or epidemiological studies on a population of subjects. A subject can thus be classified as being at risk for a complement-mediated disorder even if studies identifying the underlying risk factors did not include the subject specifically.

In one example, the subject is at risk of developing a complement-mediated disorder and the protein is administered before or after the onset of symptoms of a complement-mediated disorder. In one example, the protein is administered before the onset of symptoms of a complement-mediated disorder. In one example, the protein is administered after the onset of symptoms of a complement-mediated disorder. In one example, the protein of the present disclosure is administered at a dose that alleviates or reduces one or more of the symptoms of a complement-mediated disorder in a subject at risk.

Symptoms of a complement-mediated disorder will be apparent to the skilled person and will be dependent on the specific disorder. Exemplary symptoms of a complement-mediated disorder include, for example:

Recurring infection;

Joint inflammation;

Muscle weakness;

Rash or discolouration of the skin;

Edema, especially in the extremities (e.g., feet, hands, legs or arms) or eyes;

Abdominal pain;

Breathing difficulties;

Nausea;

Fatigue;

Hematuria;

Partial or complete paralysis; and

Poor cognitive ability.

The methods of the present disclosure can be readily applied to any form of complement-mediated disorder in a subject.

In one example, a method of the disclosure reduces any symptom of a complement-mediated disorder known in the art and/or described herein.

As will be apparent to the skilled person a "reduction" in a symptom of a complement-mediated disorder in a subject will be comparative to another subject who also suffers from a complement-mediated disorder but who has not received treatment with a method described herein. This does not necessarily require a side-by-side comparison of two subjects. Rather population data can be relied upon. For example, a population of subjects suffering from a complement-mediated disorder who have not received treatment with a method described herein (optionally, a population of similar subjects to the treated subject, e.g., age, weight, race) are assessed and the mean values are compared to results of a subject or population of subjects treated with a method described herein.

In the case of a complement-mediated condition that is an ischemia-reperfusion injury due to or associated with organ transplantation, the protein of the disclosure or composition comprising the protein can be administered before, during or after transplantation. In some examples, the protein or composition is administered to an organ transplantation donor. In other examples, the protein or composition is administered to the subject, wherein the subject is an organ transplantation recipient. In one example, the protein or composition is administered to a harvested organ ex vivo, prior to organ transplantation. For example, the harvested organ can be perfused or infused with a solution comprising the protein or composition prior to transplantation. In some examples, the organ transplant is a solid organ transplant.

It will be apparent to the skilled person from the foregoing, that the present disclosure provides a method of organ transplantation or for improving outcome of an organ transplantation or improving function of a transplanted organ or for preventing delayed graft function, the method comprising administering a protein or composition comprising the protein to an organ transplant donor prior to collection of the organ; collecting the organ and transplanting the organ into an organ transplant recipient.

The present disclosure also provides a method for preparing a transplant organ from an organ donor to improve organ function in an organ transplant recipient, the method comprising administering to the organ donor a protein or composition prior to collection of the organ.

The present disclosure additionally provides a method for preventing organ transplant rejection, the method comprising administering to an organ donor a protein or composition prior to collection of the organ, collecting the organ and transplanting the organ into an organ transplant recipient.

In some examples, the organ is a solid organ. In some examples the organ is a lung, liver, pancreas, heart, or kidney.

In some examples, the method additionally comprises administering the protein or composition to the organ transplant recipient. For example, the protein or composition is administered to the organ transplant recipient before the transplant or at the time of transplanting the organ (i.e., during transplantation).

The present disclosure also provides a method of organ transplantation or for improving outcome of an organ transplantation or improving function of a transplanted organ or for preventing delayed graft function, the method comprising administering a protein or composition to an organ transplant recipient prior to transplanting the organ and then transplanting the organ into the organ transplant recipient.

In one example, the organ transplant donor is brain dead. For example, the organ donor is alive by virtue of life support but is brain dead.

In one example of the disclosure, the protein or composition is administered before reperfusion, for example, in the case of an organ transplant, the protein or composition is administered to an organ transplant recipient prior to reperfusion of the transplanted organ (e.g., the protein or composition is administered prior to the transplantation or during the transplantation but before reperfusion).

In the case of administration to a brain dead donor, the protein or composition can be administered at any time between brain death and organ collection. In some examples, the protein or composition is administered to a harvested organ ex vivo, prior to organ transplantation. For example, the harvested organ can be perfused or infused with a solution comprising the protein or composition prior to transplantation.

Compositions

In some examples, a protein as described herein can be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term "parenteral" as used herein includes subcutaneous, intravenous, intramuscular, intraperitoneal, intrathecal, intraventricular, intrasternal, and intracranial injection or infusion techniques.

Methods for preparing a protein into a suitable form for administration to a subject (e.g. a pharmaceutical composition) are known in the art and include, for example, methods as described in Remington's Pharmaceutical Sciences (18th ed., Mack Publishing Co., Easton, Pa., 1990) and U.S. Pharmacopeia: National Formulary (Mack Publishing Company, Easton, Pa., 1984).

The pharmaceutical compositions of this disclosure are particularly useful for parenteral administration, such as intravenous administration or administration into a body cavity or lumen of an organ or joint. The compositions for administration will commonly comprise a solution of protein dissolved in a pharmaceutically acceptable carrier, for example an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of proteins of the present disclosure in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

Upon formulation, proteins of the present disclosure will be administered in a manner compatible with the dosage formulation and in such amount as is therapeutically/prophylactically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver compounds of the present disclosure.

WO2002/080967 describes compositions and methods for administering aerosolized compositions comprising antibodies for the treatment of, e.g., asthma, which are also suitable for administration of a protein of the present disclosure.

Conjugates

In some examples, the protein of the disclosure is conjugated to another compound. Methods for conjugation of the protein will be apparent to the skilled person and/or described herein. All forms and methods of conjugation (i.e., binding) are contemplated by the present disclosure, including, for example, direct conjugation between the protein and another compound/moiety as described herein or indirect binding (e.g., by virtue of a linker between the protein and the other compound/moiety). In one example, the conjugate is formed by a chemical conjugation (e.g., by an amine bond or disulphide bond) or by genetic fusion.

In one example, the disclosure provides a fusion protein comprising the protein of the disclosure and the other compound. For example, the other compound can be positioned at the N-terminus of the protein, C-terminus of the protein or any combination thereof.

In one example, the protein is conjugated to the other compound via a linker. For example, the linker can be a peptide linker.

In one example, the linker is a flexible linker. A "flexible" linker is an amino acid sequence which does not have a fixed structure (secondary or tertiary structure) in solution. Such a flexible linker is therefore free to adopt a variety of conformations. Flexible linkers suitable for use in the present disclosure are known in the art. An example of a flexible linker for use in the present invention is the linker sequence SGGGGS/GGGGS/GGGGS or (Gly4Ser)3. Flexible linkers are also disclosed in WO1999045132.

The linker may comprise any amino acid sequence that does not substantially hinder interaction of the binding region with its target. Preferred amino acid residues for flexible linker sequences include, but are not limited to, glycine, alanine, serine, threonine proline, lysine, arginine, glutamine and glutamic acid.

The linker sequences between the binding regions preferably comprise five or more amino acid residues. The flexible linker sequences according to the present disclosure consist of 5 or more residues, preferably, 5, 6, 7, 8, 9, 10, 11, 12, 13, 14, 15, 16, 17, 18, 19 or 20 or 25 or 30 or more residues. In a highly preferred embodiment of the invention, the flexible linker sequences consist of 5, 7, 10, 13 or 16 or 30 residues.

In one example, the flexible linker has an amino acid sequence according to SEQ ID NO: 31, i.e., GSGGSGGSGGSGS (GS13).

In one example, the flexible linker has an amino acid sequence according to SEQ ID NO: 35, i.e., SGGSGGSGGSGGSGGSGGSGGSGGSGGSGS (GS30).

Exemplary compounds that can be conjugated to a protein of the disclosure and methods for such conjugation are known in the art and described herein.

Half-Life Extending Moieties

In one example, the protein is conjugated to a half-life extending moiety. Half-life extending moieties suitable for use in the present disclosure will be apparent to the skilled person, and include, but are not limited to, those described herein. For example, the half-life extending moiety is selected from the group consisting of a human serum albumin or functional fragment thereof, an immunoglobulin Fc region or functional fragment thereof, afamin, alpha-fetoprotein, vitamin D binding protein, antibody fragments that bind to albumin and polymers.

In one example, the half-life extending moiety is a human serum albumin or functional fragment thereof.

In one example, the half-life extending moiety is an immunoglobulin Fc region or functional fragment thereof.

In one example, the half-life extending moiety is an afamin.

In one example, the half-life extending moiety is an alpha-fetoprotein.

In one example, the half-life extending moiety is a vitamin D binding protein.

In one example, the half-life extending moiety is an antibody fragment that binds to albumin.

In one example, the half-life extending moiety is a polymer.

In one example, the half-life extending moiety is polysialic acid. Thus, in some examples, the protein disclosed herein is polysialylated.

Albumin Proteins and Variants Thereof

In one example, the half-life extending moiety is albumin, or a functional fragment or variant thereof.

Serum albumin, or blood albumin, is the most abundant blood protein and functions as a carrier protein for steroids, fatty acids and thyroid hormones in the blood, as well as playing a major role in stabilising extracellular fluid volume.

In one example, the albumin, functional fragment or variant thereof is serum albumin, such as human serum albumin. For the purposes of nomenclature only and not limitation an exemplary sequence of a mature human serum albumin is set out in NCBI GenBank Accession ID: AEE60908 and SEQ ID NO: 32.

In one example, the albumin, functional fragment or variant thereof, comprises one or more amino acid substitutions, deletions or insertions. Amino acid substitutions suitable for use in the present disclosure will be apparent to the skilled person and include naturally-occurring substitutions and engineered substitutions such as those described, for example, in WO2011051489, WO2014072481, WO2011103076, WO2012112188, WO2013075066, WO2015063611, and WO2014179657.

In one example, the present disclosure provides a protein conjugated to an albumin family protein, e.g., a protein that is structurally or evolutionarily related to albumin. For example, the protein is conjugated to afamin, alpha-fetoprotein or a vitamin D binding protein.

In another example, the protein is fused, e.g., expressed as a fusion protein, to an albumin family protein, e.g., a protein that is structurally or evolutionarily related to albumin. For example, the protein is fused, e.g., as a fusion protein, to afamin, alpha-fetoprotein or a vitamin D binding protein.

Polymers

In one example, the present disclosure provides a protein conjugated to a polymer. Suitable polymers for use in the present disclosure will be apparent to the skilled person and/or are described herein.

In one example, the protein is conjugated to a polyethylene glycol (PEG). For example, the polymer comprises mono- or poly- (e.g., 2-4) polyethylene glycol (PEG) moieties. For example, the mono-poly- (e.g., 2-4) polyethylene glycol (PEG) moieties extend in vivo half-lives of the protein.

Pegylation may be carried out by any of the pegylation reactions available. Exemplary methods for preparing pegylated protein products can generally include (a) reacting a polypeptide with polyethylene glycol (such as a reactive ester or aldehyde derivative of PEG) under conditions whereby the protein becomes attached to one or more PEG groups; and (b) obtaining the reaction product(s).

The skilled person will be aware of different PEG attachment methods which include, but are not limited to those described in e.g., EP 0 401 384; Malik et al., Exp. Hematol., 20:1028-1035 (1992); Francis, Focus on Growth Factors, 3 (2): 4-10 (1992); EP 0 154 316; EP 0 401 384; WO 92/16221; WO 95/34326; U.S. Pat. No. 5,252,714.

Immune Modulators

In one example, the other compound is an immune modulator. In one example, the other compound is a cytokine, lymphokine, chemokine, or other immune modulator. Such agents can be delivered to target cells to modulate an immune response. The term "immune modulator", as used herein, means a substance which modulates the immune system. The immune modulator may adjust the immune response to a desired level, as in immunopotentiation, immunosuppression, or induction of immunologic tolerance. Immune modulators for use as conjugates with the protein of the disclosure include, but are not limited to, proteins, peptides, antibodies, antibody fragments, small molecules, cytokines, hormones, enzymes, nucleic acids, toxins, anti-angiogenic agents, cytotoxic agents, pro-apoptotic agents and other known therapeutic agents. Preferred immune modulators include small molecules (for example, R848, Loxoribine, Stat-3 inhibitors, TGFβ inhibitors, Rapamycin/FK506), cytokines (for example, IL-2, TGFβ), antibody fragments (for example, CTLA-4 agonist scFv), nucleic acids (for example, CpG, siRNA).

In one example, the other compound is an immunosuppressant. Immunosuppressants can be used, for example, to help prevent organ rejection or to treat an autoimmune disease. Suitable immunosuppressants include, but are not limited to glucocorticoids (e.g., prednisone, dexamethasone, and hydrocortisone), cytostatics (e.g., purine analogs, alkylating agents, and methotrexate), drugs acting on immunophilins (e.g., ciclosporin, tacrolimus, and sirolimus), and other drugs such as interferons, opiods, and TNF-binding proteins.

Combination Therapies

In one example, a protein of the present disclosure is administered in combination with another compound useful for treating a disease or condition described herein, either as combined or additional treatment steps or as additional components of a therapeutic formulation.

In one example, the protein of the disclosure is used in combination with at least one additional known compound or therapeutic protein that is currently being used or is in development for inhibiting complement activity or preventing or treating complement-mediated disorders. Compounds currently used in the treatment of complement-mediated disorders are known in the art, and include antibodies against C5 and activated forms thereof (C5a), e.g., eculizumab, Berinert Human C1 esterase inhibitor, Human C1 esterase inhibitor, Ruconest Recombinant C1 esterase inhibitor, Cinryze Human C1 esterase inhibitor, Anti human MASP-2 monoclonal antibody, APL-2 C3-inhibiting peptide, Lampalizumab, TNT009 Anti-C1s Antibody. Additional compounds are described in Reis et al., *Clin Immunol.* December; 161 (2): 225-240, 2015.

In some examples, the other compound is an anti-inflammatory compound. Alternatively, or additionally, the other compound is an immunosuppressant. Alternatively, or additionally, the other compound is a corticosteroid, such as prednisone and/or prednisolone. Alternatively, or additionally, the other compound is methotrexate. Alternatively, or additionally, the other compound is mycophenolate mofetil. Alternatively, or additionally, the other compound is an anti-CD20 antibody (e.g., rituximab or ofatumumab). Alternatively, or additionally, the other compound is an anti-CD22 antibody (e.g., epratuzumab). Alternatively, or additionally, the other compound is an anti-TNF antibody (e.g., infliximab or adalimumab or golimumab) or soluble TNF receptor (e.g., etanercept). Alternatively, or additionally, the other compound is a CTLA-4 antagonist (e.g., abatacept, CTLA4-Ig). Alternatively, or additionally, the other compound is an anti-IL-6 antibody. Alternatively, or additionally, the other compound is a BLys antagonist, such as an anti-BLys antibody (e.g., belimumab). Alternately or additionally the other compound is tissue plasminogen activator (t-PA).

In some examples, the other compound inhibits or reduces the expression or activity of one or more of:

(i) kidney injury molecule 1 (KIM-1);
(ii) neutrophil gelatinase-associated lipocalin (NGAL);
(iii) interleukin 1 beta (IL-1B);
(iv) interleukin 6 (IL-6);
(v) tumor necrosis factor alpha (TNFα);
(vi) complement component 5a receptor 1 (C5AR1);
(vii) macrophage inflammatory protein 2-alpha (MIP2-alpha);
(viii) intercellular Adhesion Molecule 1 (ICAM-1);
(ix) E-selectin;
(x) C-X-C motif chemokine ligand 1 (CXCL1);
(xi) interleukin 8 receptor beta (IL-8Rβ); and
(xii) monocyte chemoattractant protein 1 (MCP-1).

In some examples, the other compound is hydrogen sulfide. In some examples, the other compound is cyclosporine. In some examples, the other compound is TRO40303, as described in Le Lamer et al., *J Transl Med* (2014). In some examples, the other compound is superoxide dismutase. In some examples, the other compound is a cannabinoid or a synthetic analog thereof.

In some examples, the other compound is one that is commonly used in transplantation surgery.

It will be apparent to a person skilled in the art that the examples of other compounds that are suitable for combination therapy with the proteins of the disclosure will also be suitable examples of compounds for conjugation with the proteins of the disclosure, and vice versa.

As will be apparent from the foregoing, the present disclosure provides methods of concomitant therapeutic treatment of a subject, comprising administering to a subject in need thereof an effective amount of a first agent and a second agent, wherein the first agent is a protein of the present disclosure, and the second agent is the other compound.

As used herein, the term "concomitant" as in the phrase "concomitant therapeutic treatment" includes administering a first agent in the presence of a second agent. A concomitant therapeutic treatment method includes methods in which the first, second, third or additional agents are co-administered. A concomitant therapeutic treatment method also includes methods in which the first or additional agents are administered in the presence of a second or additional agent, wherein the second or additional agent, for example, may have been previously administered. A concomitant therapeutic treatment may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g. a human).

In one example, the protein of the disclosure is administered simultaneously with the other compound. In one example, the protein is administered before the other compound. In one example, the protein is administered after the other compound. In one example, the protein of the disclosure comprises another one or more antigen-binding sites which bind to a different antigen to C2. Thus, the protein of the disclosure may, in some examples, comprise two or more different antigen-binding sites.

In some examples, the protein is a bispecific protein, such as a bispecific antibody. In some examples, the other one or more antigen-binding sites bind to their antigen with greater affinity at pH 7.3 than at pH 6.0.

In some examples, the other one or more antigen-binding sites include any one or more of the antigen-binding sites of the antibodies listed above as suitable for administration in combination with the protein of the disclosure. For example, the other one or more antigen-binding sites may bind to another component of complement system, such as a subunit of the C1 complex (e.g., C1s), C3, C3a, C3b, C4, C4a, C4b, C5, C5a, C5b, C6, C7, C8, or C9. Alternatively, or additionally the other one or more antigen-binding sites may bind to MASP-2, CD20, CD22, TNF, CTLA-4, IL-6, IL-6R, or BLys. In some examples, the other one or more antigen-binding sites include an antigen-binding site which binds to C5. In some examples, the other one or more antigen-binding sites include an antigen-binding site which binds to IL-6R.

Dosages and Timing of Administration

Suitable dosages of proteins of the present disclosure will vary depending on the specific protein, the condition to be treated and/or the subject being treated. It is within the ability of a skilled physician to determine a suitable dosage, e.g., by commencing with a sub-optimal dosage and incrementally modifying the dosage to determine an optimal or useful dosage. Alternatively, to determine an appropriate dosage for treatment/prophylaxis, data from the cell culture assays or animal studies are used, wherein a suitable dose is within a range of circulating concentrations that include the $ED_{50}$ of the active compound with little or no toxicity. The dosage may vary within this range depending upon the dosage form employed and the route of administration utilized. A therapeutically/prophylactically effective dose can be estimated initially from cell culture assays. A dose may be formulated in animal models to achieve a circulating plasma concentration range that includes the $IC_{50}$ (i.e., the concentration of the compound which achieves a half-maximal inhibition of symptoms) as determined in cell culture. Such information can be used to more accurately determine useful doses in humans. Levels in plasma maybe measured, for example, by high performance liquid chromatography.

In some examples, a method of the present disclosure comprises administering a prophylactically or therapeutically effective amount of a protein described herein.

The term "therapeutically effective amount" is the quantity which, when administered to a subject in need of treatment, improves the prognosis and/or state of the subject and/or that reduces or inhibits one or more symptoms of a clinical condition described herein to a level that is below that observed and accepted as clinically diagnostic or clinically characteristic of that condition. The amount to be administered to a subject will depend on the particular characteristics of the condition to be treated, the type and stage of condition being treated, the mode of administration, and the characteristics of the subject, such as general health, other diseases, age, sex, genotype, and body weight. A person skilled in the art will be able to determine appropriate dosages depending on these and other factors. Accordingly, this term is not to be construed to limit the present disclosure to a specific quantity, e.g., weight or amount of protein(s), rather the present disclosure encompasses any amount of the protein(s) sufficient to achieve the stated result in a subject.

As used herein, the term "prophylactically effective amount" shall be taken to mean a sufficient quantity of a protein to prevent or inhibit or delay the onset of one or more detectable symptoms of a clinical condition. The skilled artisan will be aware that such an amount will vary depending on, for example, the specific protein(s) administered and/or the particular subject and/or the type or severity or level of condition and/or predisposition (genetic or otherwise) to the condition. Accordingly, this term is not to be construed to limit the present disclosure to a specific quantity, e.g., weight or amount of protein(s), rather the present disclosure encompasses any amount of the protein(s) sufficient to achieve the stated result in a subject.

For in vivo administration of the proteins described herein, normal dosage amounts may vary from about 10 ng/kg up to about 300 mg/kg of an individual's body weight or more per day. For repeated administrations over several days or longer, depending on the severity of the disease or disorder to be treated, the treatment can be sustained until a desired suppression of symptoms is achieved.

Dosages can vary from about 0.1 mg/kg to about 300 mg/kg, e.g., from about 0.2 mg/kg to about 200 mg/kg, such as, from about 0.5 mg/kg to about 20 mg/kg, in one or more dose administrations daily, for one or several days.

In some examples, at the time of commencing therapy, the subject is administered the protein on no more than 7 consecutive days or 6 consecutive days or 5 consecutive days or 4 consecutive days.

In some examples, the protein is administered at an initial (or loading) dose which is higher than subsequent (maintenance doses). For example, the protein can be administered at an initial dose of between about 10 mg/kg to about 30 mg/kg. The protein is then administered at a maintenance dose of between about 0.0001 mg/kg to about 30 mg/kg. The maintenance doses may be administered every 2-30 days, such as, every 2 or 3 or 6 or 9 or 12 or 15 or 18 or 21 or 24 or 27 or 30 days.

In some examples, a dose escalation regime is used, in which the protein is initially administered at a lower dose than used in subsequent doses. This dosage regime is useful in the case of subject's initially suffering adverse events In the case of a subject that is not adequately responding to treatment, multiple doses in a week may be administered. Alternatively, or in addition, increasing doses may be administered.

A subject may be retreated with the protein, by being given more than one exposure or set of doses, such as at least about two exposures, for example, from about 2 to 60 exposures, and more particularly about 2 to 40 exposures, most particularly, about 2 to 20 exposures.

In one example, any retreatment may be given when signs or symptoms of disease return.

In another example, any retreatment may be given at defined intervals. For example, subsequent exposures may be administered at various intervals, such as, for example, about 24-28 weeks or 48-56 weeks or longer. For example, such exposures are administered at intervals each of about 24-26 weeks or about 38-42 weeks, or about 50-54 weeks.

In another example, for subjects experiencing an adverse reaction, the initial (or loading) dose may be split over numerous days in one week or over numerous consecutive days.

Administration of a protein according to the methods of the present disclosure can be continuous or intermittent, depending, for example, on the recipient's physiological condition, whether the purpose of the administration is therapeutic or prophylactic, and other factors known to skilled practitioners. The administration of a protein may be essentially continuous over a preselected period of time or may be in a series of spaced doses, e.g., either during or after development of a condition.

Kits and Other Compositions of Matter

Another example of the disclosure provides kits containing a protein of the disclosure useful for inhibiting complement activity or for the treatment or prevention of a complement-mediated disorder as described above.

In one example, the kit comprises (a) a container comprising the protein optionally in a pharmaceutically acceptable carrier or diluent; and (b) a package insert with instructions for inhibiting complement activity or for treating or preventing a complement-mediated disorder in a subject.

In one example, the kit comprises (a) at least one protein of the disclosure optionally in a pharmaceutically acceptable carrier or diluent; (b) instructions for using the kit in inhibiting complement activity or for treating or preventing a complement-mediated disorder in the subject; and (c) optionally, at least one further therapeutically active compound or drug.

In accordance with this example of the disclosure, the package insert is on or associated with the container. Suitable containers include, for example, bottles, vials, syringes, etc. The containers may be formed from a variety of materials such as glass or plastic. The container holds or contains a composition that is effective for inhibiting complement activity or for treating or preventing a complement-mediated disorder and may have a sterile access port (for example, the container may be an intravenous solution bag or a vial having a stopper pierceable by a hypodermic injection needle). At least one active agent in the composition is the protein. The label or package insert indicates that the composition is used for treating a subject eligible for treatment, e.g., one having or predisposed to developing a complement-mediated disorder, with specific guidance regarding dosing amounts and intervals of the protein and any other medicament being provided. The kit may further comprise an additional container comprising a pharmaceutically acceptable diluent buffer, such as bacteriostatic water for injection (BWFI), phosphate-buffered saline, Ringer's solution, and/or dextrose solution. The kit may further include other materials desirable from a commercial and user standpoint, including other buffers, diluents, filters, needles, and syringes.

The kit optionally further comprises a container comprising a second medicament, wherein the protein of the disclosure is a first medicament, and which kit further comprises instructions on the package insert for treating the subject with the second medicament, in an effective amount. The second medicament may be another compound or therapeutic protein that is currently being used or is in development for inhibiting complement activity or preventing or treating complement-mediated disorder, as described herein above.

The present disclosure includes the following non-limiting Examples

NON-LIMITING EXAMPLES

Materials and Methods

Generation of cDNA C2 Expression Plasmids

Human Complement component C2 cDNA (GenBank Accession no. NP_000054) and Human IgG4Fc (aa99-327; GenBank Accession no. P01861) were codon-optimized for human expression and synthesized by Geneart® (Invitrogen™, Thermo Fisher Scientific). Full-length human C2 with a C-terminal 8× Histidine-tag fused in-frame was generated using standard PCR-based techniques, as were fusions HuIgG4Fc to the C-terminus of C2. Each cDNA was generated with a Kozak consensus sequence (GCCACC) immediately upstream of the initiating methionine (+1). Once each cDNA was completed, it was digested with NheI and XhoI and ligated into pcDNA3.1 (Invitrogen™, Thermo Fisher Scientific). Mutagenesis of selected surface amino acids within the human C2 sequence-based on the crystal structure of C2a (PDB 216Q; Milder et al., Structure 14 1587-97 (2006))—were performed using standard PCR and cloning techniques as above.

Large-scale preparations of plasmid DNA were carried out using QIAGEN Plasmid Giga Kits according to the manufacturer's instructions. The nucleotide sequences of all plasmid constructs were verified by sequencing both strands using BigDye™ Terminator Version 3.1 Ready Reaction Cycle Sequencing (Invitrogen™, Thermo Fisher Scientific) and an Applied Biosystems 3130xl Genetic Analyzer.

Cell Culture and Transient Transfections

Expi293F™ cells and the mammalian expression vector pcDNA3.1 were obtained from Invitrogen™, Thermo Fisher Scientific. Cells were cultured in Expi293TM Expression Medium (Invitrogen™, Thermo Fisher Scientific.). All tissue culture media were supplemented with Antibiotic-Antimycotic (GIBCO®, Thermo Fisher Scientific) and cells were maintained at 37° C. in incubators with an atmosphere of 8% $CO2$. Transient transfections of expression plasmids using Expi293FTM cells were performed using Expi293TM Expression system according to the manufacturer's recommendations (Invitrogen™, Thermo Fisher Scientific).

Purification of C2

Histidine-tagged human C2 proteins were purified via immobilised metal-affinity chromatography using an AKTA Xpress system and a two-step automated method. 30 ml Expi293F cell culture supernatant was directly loaded onto a 1 ml HiTrap Excel nickel-Sepharose column (GE Healthcare) pre-equilibrated with 20 mM $NaH2PO4$, 500 mM NaCl, 10 mM Imidazole (pH 7.4). The column was then washed with 20 mM $NaH2PO4$, 500 mM NaCl, 25 mM Imidazole (pH 7.4) to remove non-specifically bound proteins prior to elution of C2 using 20 mM $NaH2PO4$, 500 mM NaCl, 500 mM Imidazole (pH 7.4). For buffer exchange, the entire eluate was automatically loaded onto a 26/10 HiPrep desalting column (GE Healthcare) equilibrated in mt-PBS (137 mM NaCl, 27 mM KCl, 8.1 mM $Na2HPO4$, 1.15 mM $KH2PO4$, pH 7.4). Following elution in mt-PBS, fractions containing the purified protein were pooled and concentrated above 5 mg/L using Amicon ultra-centrifugal filters (50 kDa MWCO). The concentrated proteins were then sterile filtered and stored at −80° C.

Panning of Phagemid Libraries for Human C2 Binders

Phage were selected from a phagemid library against human C2 using human C2 fused to the Fc region of human IgG1 (referred to as "Fc-huC2"). Three rounds of panning were done using 10 μg of Fc-huC2 immobilised on Dyna-beads M-280 Streptavidin via biotin anti-human Fc capture. Prior to each round of panning, the phagemid library was depleted of non-specific binders to either streptavidin or Fc by incubation with Dynabeads M-280 Streptavidin and beads coated via biotin anti-human Fc antibody capture with an irrelevant human IgG1 antibody. For depletions, the same concentration (10 μg) of irrelevant antibody was used per round as target protein.

Isolation of Human C2 Binder Clones

Ninety-five colonies from the round three outputs from the panning campaign were picked for screening by Fab-phage ELISA. Rescued phagemid supernatants of these clones were tested for binding to soluble human C2 or activated C2 (C2a) proteins with either an Fc or His tag (in-house generated proteins) by ELISA. To determine the diversity of these human C2 phagemid binders, the Fab cassette from these clones was PCR amplified and then sequenced.

Antibody Sequence Germlining

Germlining of the antibody sequences was performed firstly by aligning the antibody sequences to human germ-line sequences using IgBlast (https://www.ncbi.nlm.nih.gov/igblast/) to identify the framework regions based on KABAT V domain delineation system. The amino acid residues different to the corresponding germline framework sequences were then back-mutated to germline sequences. DNA fragment encoding the mutated V sequences were finally synthesised by Thermo Fisher Scientific (Massachusetts, USA) and cloned into a mammalian expression vector for expression and analysis.

Purification of Antibodies

C2 binding proteins were purified by Protein A affinity using the AKTA Xpress system and a two-step automated method. 500 ml Expi293F cell culture supernatant was loaded directly onto a 5 ml HiTrap MabSelect SuRe column (GE Healthcare) pre-equilibrated with mt-PBS (137 mM NaCl, 27 mM KCl, 8.1 mM Na2HPO4, 1.15 mM KH2PO4, pH7.4). The column was then washed with 500 mM L-Arg; 10 mM TRIS; 150 mM NaCl (pH 7.5) to remove endotoxin and non-specifically bound proteins prior to elution of the mAbs with 0.1 M sodium acetate (pH 3.0). To separate aggregated material from the monomeric mAbs, the entire eluate was automatically loaded onto a HiLoad 26/60 Super-dex 200 (prep grade) size exclusion column (GE Healthcare) equilibrated in mt-PBS (137 mM NaCl, 27 mM KCl, 8.1 mM Na2HPO4, 1.15 mM KH2PO4, pH 7.4). Fractions not containing aggregate were pooled and concentrated above 10 mg/ml using Amicon ultra-centrifugal filters (50 kDa MWCO). The concentrated proteins were then sterile fil-tered and stored at 4° C.

ELISAs for Binding of Antibodies to C2 at pH 5.5 vs 7.4

Unique anti-human C2 antibodies were initially tested at different pH (pH 5.5 and 7.4) in a titration ELISA. These titration experiments were done in duplicate. Human C2 proteins were coated at 2 μg/ml in mouse-tonicity phos-phate-buffered saline (MTPBS; pH 7.4 or pH 5.5) onto Maxisorp ELISA plates (100 μL/well) overnight at 4° C. After removing the coating solution, the plates were blocked for 2 hours at 37° C. with 200 μl/well of 5% skim milk/ TBS/T (TPBS, 0.05% Tween-20; not pH specific). The antibodies were serially diluted 5-fold from a starting con-centration of 100 μg/ml down to 1.28 ng/ml in 2% skim milk/MTPBS/T (pH 7.4 or pH 5.5). Added 100 μL/well of diluted antibody to the appropriate ELISA plate. As a control for non-specific binders to human C2 proteins, ELISA plates were incubated with an irrelevant human IgG antibody (the same antibody as used for, depletions when panning the phagemid libraries). After 90 minutes incubation at room temperature, the plates were washed×5 with TBS/T (not pH specific). Antibody binding was then detected with 100 μl/well of anti-Fab-HRP antibody diluted 1:2,500 in 2% skim milk/MTPBS/T (pH 7.4 or pH 5.5) for 1 hour at room temperature. After washing the plates×5 with TBS/T (not pH specific), they were developed for 10 minutes using 100 μL/well of TMB/E substrate (ES001-500ML; Chemicon) and the reaction was stopped upon addition of 2M phos-phoric acid (50 μL/well). The ELISA plates were read at absorbance 450 nm.

Purification of Fc Fusions

For the purification of Fc fused C2 proteins, culture supernatant was loaded directly onto MabSelect SuRe affin-ity resin (GE Healthcare) pre-equilibrated with mt-PBS (137 mM NaCl, 27 mM KCl, 8.1 mM Na2HPO4, 1.15 mM KH2PO4, pH7.4). After all supernatant was loaded, the resin was washed with mt-PBS, pH7.4. Weakly bound non-target proteins were block eluted with 0.1M Sodium Citrate, pH 5.0. Resin-bounded huC2 was block eluted with 0.1M Sodium Citrate, pH 3.0, collecting eluted protein based on absorbance at 280 nm. Protein collected during the elution was loaded onto a HiLoad 26/60 superdex 200 prep grade column (GE Healthcare) pre-equilibrated in mt-PBS to remove any contaminating proteins and buffer exchange into desired buffer. Purified protein was concentrated using ami-con ultra centrifugal filters with 50 kDa MWCO to desired concentration, sterile filtered and stored at −80° C.

Surface Plasmon Resonance—General Assay Design

Surface plasmon resonance (SPR, Biacore) was used for all binding affinity analyses. In brief, goat anti-human IgG was directly immobilised onto the carboxymethyl dextran surface of CM5 sensorchips to approximately 12,000 RU using standard NHS/EDC chemistry at pH 5. The immobi-lised antibody surface was pre-conditioned with ten injec-tions of polyclonal human IgG (Privigen 60s) prepared at 1 μg/mL. Ligands (anti-C2 mAbs) were captured at the begin-ning of each cycle as described below. An adjacent spot or flow cell in which only Polyclonal IgG was capture was used as a reference surface. The goat anti-human IgG Fc antibody surface was regenerate in 100 mM H3PO4, injected for 45 seconds at the end of each cycle. Experiments were per-formed at 37° C. and the flow rate of each experiment was kept constant at 30 μL/min.

Sensogram data was double-referenced against a refer-ence anti-IgG surface (i.e. minus anti-C2 mAb) and blank buffer injections obtained within each experiment. The bind-ing data was fit to 1:1 (kinetic or steady-state) model using local Rmax and null refraction index (RI=0) when appro-priate. Buffers and solutions were filtered (0.22 μm) prior to use.

Competitive Binding Experiments

Binning experiments were designed to test the competi-tive binding of antibody pairs (ligand mAb1 vs analyte mAb2) to human C2 (ligand antigen). Each antibody was tested as either a ligand or analyte in a qualitative manner. First, antibody ligands (mAb1, 2 μg/mL) were captured at the anti-IgG surface to approximately 350 RU followed by blocking with polyclonal human IgG (1 μg/mL) for 60s. The anti-C2 surface was saturated with human C2 ligand (100 nM, 8.2 μg/mL). The antibody analyte (mAb2) was finally injected for 120s (1 μg/mL). Non-competitive binder pairs were identified as those that had positive binding responses at the end of analyte injection. Neutral or negative binding responses indicate competitive pairs, or a ligand antibody (mAb1) with a fast off-rate, thus, not capable of capturing human C2 long enough for the analyte antibody (mAb2) to bind. Such antibodies could only be tested as analytes (mAb2). Binning experiments were performed at 37° C. in HBS-EP (10 mM Hepes, 150 mM NaCl, 3 mM EDTA, 0.05% Tween 20, 0.1% BSA) at pH 7.3.

Binding Kinetics Experiments of Human and Cyno C2 at Neutral and Acidic pH

Purified recombinant C2 (WT or alanine mutants) was prepared in running buffer containing 10 mM HEPES, 150 mM NaCl, 3 mM EDTA, 0.05% Tween, 0.1% BSA, pH7.3 (referred to as HBS-EP) prior the beginning of each experiment and tested against anti-C2 mAb (1 μg/mL, 250 RU) captured for 60 seconds. Human C2 concentrations ranged from 7.8 to 500 nM. Each analyte concentration was injected in random order and in duplicate. Analyte association and dissociation was monitored for 200 and 600 seconds, respectively. Buffer blank cycles were included for reference subtraction. Double referenced sensorgrams were fitted to either a 1:1 kinetic model, including a term for mass transport limitation or to a 1:1 steady state model where responses at the end of the association phase were plotted against respective concentrations. Kinetic experiments were performed at 37° C. and used HBS-EP at pH 7.3 and pH 6.0. The anti-human IgG Fc antibody surface was regenerated with 45 seconds injection of 100 mM H3P04.

As a comparison, the same binding kinetics experiments were performed in a buffer containing ammonium sulfate rather than sodium chloride. In these experiments, the running buffer consisted of 10 mM HEPES, 10 mM MES, 150 mM $(NH_4)_2SO_4$, 3 mM EDTA, 0.05% Tween, 0.1% BSA (referred to as "MHAs").

C2-Binding Kinetics in the Presence of Calcium

The effect of calcium on antibody binding was determined with the addition of calcium chloride to the SPR running buffer. Calcium concentrations ranged from zero (i.e. no added calcium, control) to near physiological levels (0.02, 0.2 and 2 mM $CaCl_2 \cdot 2H_2O$, MW 147.02 Da). Control buffer was prepared with 3 mM EDTA. In this experiment, all 4 buffer lines were used for specific buffer compositions as line 1 (control, 0 mM $CaCl_2$), line 2 (0.02 mM $CaCl_2$), line 3 (0.2 mM $CaCl_2$) and line 4 (2 mM $CaCl_2$).

Purified human C2 zymogen was tested in physiological conditions (pH 7.3) at concentrations ranging from 1.9 to 500 nM and in acidic conditions (pH 6) at concentrations ranging from 3.9 to 2000 nM. Analyte samples were prepared in 2-fold serial dilutions from a 2 mM stock prepared in running buffer. Each analyte concentration was tested in duplicate. Privigen (polyclonal human IgG; 2 μg/mL) was used for surface conditioning. Analyte association and dissociation were monitored for 180 and 600 seconds, respectively. Each antibody was tested in triplicate. The flow rate was set to 30 μL/min. The experiment was performed at 37° C. Buffers were filtered (0.22 μm) prior to use. Activated human C2 (huC2a) did not bind RF16-226 at neutral or acidic pH despite the calcium concentration.

Sensorgrams were double-referenced using reference surface and blank buffer injection data obtained within each experiment. Rate constants and binding affinities were calculated at neutral pH using a 1:1 kinetic model with local Rmax and null refraction index (RI-0). However, binding at acidic (pH 6) had to be fit to 1:1 steady-state model due to the fast off-rate ($k_d$) constants of huC2.

Complement Inhibition Assay—Wieslab Assay

To assess complement inhibitory activity, anti-C2 antibodies were tested in an Wieslab® complement assay (Euro Diagnostica) according to the manufacturer's instructions. Briefly, the antibodies were serially diluted in PBS in a 96-well plate. 50 μl of each diluted antibody sample or PBS alone was added to 202.5 μl of pre-diluted human or cynomolgus monkey serum (1:101 for classical/lectin) in the appropriate assay diluent for each complement pathway (as per manufacturer's instructions) and incubated for 30 min at room temperature (RT). Once added to the pre-diluted serum, the final starting concentration of each antibody was either 250 or 1000 nM. 100 μl of each sample was transferred to the assay plate in duplicate and incubated for 1 hr at 37° C. (with no CO2). Wells were emptied and washed three times with 300 μl/well of 1× wash buffer (as per manufacturer's instructions). The terminal complex of C5b-9 was detected using 100 μl/well alkaline-phosphatase conjugated anti-C5b-9 specific monoclonal antibody, which was incubated for 30 min at RT. Unbound antibody was discarded and wells were washed three times with 300 μl/well of 1× wash buffer. Bound antibodies were detected using 100 μl/well alkaline phosphatase substrate solution and incubated for 30 min at RT. Absorbance at 405 nm was read using the Envision plate reader.

Raw values were expressed as a percentage of C5b-9 formation by the serum and PBS only control (i.e. 100% C5b-9 formation). Results were analysed in Graph Pad Prism for IC50 values using a log (inhibitor) vs. response— Variable slope (four parameters) fit. Bottom and top constrained to values 0 and 100, respectively.

Complement Inhibition Assay—Hemolysis Assay

To further assess the inhibition of the classical pathway of the complement system (i.e., CH50) by the anti-C2 antibodies, sheep erythrocytes (Siemens) were sensitized with rabbit anti-sheep antibodies (Ambozeptor 6000; Siemens) and diluted to 4×108 cells/mL GVB++ (gelatin veronal buffer-GVB, 0.15 mM CaCl2, 0.5 mM MgCl2). Antibodies were pre-incubated in 1/40 diluted normal human serum (NHS) or cynomolgus serum (30 min at RT) and subsequently added to the erythrocytes at a 1/1 (v/v) ratio and incubated during 1 h at 37° C. in a microtiter-plate shaking device. After adding ice-cold GVBE (GVB, 10 mM EDTA) and centrifugation (5 min at 1250×g, 4° C.), hemolysis was determined in the supernatant by measuring the absorbance of released hemoglobin at 412 nm. Cells incubated with serum and buffer only served as 100% lysis controls. The inhibition of lysis by the anti-C2 antibodies was calculated relative to control.

Inhibition of Proteolytic Processing of C2

C2 and RF16-226 at a concentration of 0.5 μM and 0.2 μM respectively were mixed together and incubated at room temperature for 30 min to allow complex formation. Active C1s at various concentrations ranging between 0 μM to 1 μM was added to C2 alone, and to the C2-RF16-226 complex. The mixture was incubated at 37° C. for 1 h. The reaction was carried out in 1×MT-PBS supplemented with 0.15 mM $CaCl_2$) and 0.5 mM $MgCl_2$ (pH 7.4). The proteins were then analysed by SDS-PAGE using NuPAGE 4-12% Bis-Tris Gel, NuPAGE MES SDS running buffer (Invitrogen Carlsbad, CA) and visualized by Coomassie staining. The bands were quantified based on their intensity and size and the mean intensities were plotted and curve-fitted using Graphpad Prism.

Fc Mutants and FcRn Affinity Measurements

Surface plasmon resonance (SPR) instruments were used to measure the binding affinity of human and cynomolgus monkey (cyno) FcRn/β2m for anti-human C2 antibodies carrying Fc mutations for improved FcRn binding at neutral (pH 7.3) and acidic (pH 6.0) conditions. Anti-C2 mAbs (1 μg/mL at pH 5) were immobilized on a carboxylmethyldextran (CM5) sensorchip surface using standard EDC/NHS chemistry. Human and Cyno FcRn/β2m (40 μM) were prepared in running buffer (10 mM HEPES, 150 mM NaCl, 10 mM MES adjusted to either pH 6 or pH 7.3) and injected on the immobilized anti-C2 surface at concentrations ranging from 0.078 to 40 μM, prepared in two-fold dilutions in running buffer. Association and dissociation phases were monitored for 180 and 600 seconds, respectively. Surface regeneration was achieved with two 60 second injections of 25 mM TRIS, 150 mM NaCl, pH 8.0 at the end of each cycle. Double referenced sensorgrams were fitted to either a 1:1 kinetic model (pH 6), including a term for mass transport limitation or to a 1:1 steady state model (pH 7.3) where responses at the end of the association phase were plotted against respective concentrations.

C2 and Anti-C2 Antibody Trafficking Assay

Freestyle 293 cells stably expressing FcRn and β2-microglobulin (Chia et al., 2018, J Biol Chem 293, 6363-6373) were seeded in Nunc Lab-Tek II CC2 chamber slide system (Thermo Fisher, NUN154534) at $0.3 \times 10^{\wedge}5$ cells/well and allowed to grow to 80-90% confluency over 2 days in 37° C. incubator. On the day of experiment, monolayers were pre-incubated with protease inhibitors (Sigma Aldrich, P1860) or carrier control (0.01% DMSO) in complete growth medium (RPMI supplemented with Glutamax and 10% fetal bovine serum) for 4.5 h at 37° C. Cell monolayers were then washed twice with PBS and incubated with 1 μM Alexa Fluor 488-labelled C2 (C2-AF488) and 0.125 UM anti-C2 antibodies diluted in either PBS, pH 7 or pH 5.5. After a 10 min pulse at 37° C., cells were washed 3 times with PBS and fresh complete growth medium was added. Cells were returned to 37° C. and internalised cargo was allowed to traffic for a further 60 min (chase). Cells were maintained in protease inhibitors or carrier control during the course of the experiment. At the specified time points, cells were fixed in 4% paraformaldehyde (PFA)/PBS (Novachem) for 10 min at room temperature, followed by quenching in 50 mM $NH_4Cl$ in PBS for 10 min at room temperature and blocking in blocking solution (5% FCS and 0.02% sodium azide in PBS) for at least 30 min to reduce unspecific binding. Monolayers were incubated with Alexa Fluor 568-conjugated anti-human IgG (Thermo Fisher, A-21090: 1/500 dilution) to detect anti-C2 antibodies for 30 min at room temperature, washed three times in PBS and stained with Hoechst 33342 (Molecular probes, H3570: 1/5000 dilution) for 10 min at room. Coverslips were washed in milli-Q water before mounting in Mowoil [10% (w/v) Hopval 5-88, 25% (w/v) glycerol and 0.1 M Tris in milli-Q water] (Merck Millipore). Confocal microscopy was performed using a Leica SP8 system. Images were collected sequentially for multicolour imaging using a 63×/1.4 NA HCX PL APO CS oil immersion objective. Alexa Fluor 488 was excited with the 488-nm line of an argon laser, Alexa Fluor 568 was excited with a 543-nm HeNe laser, and Hoechst 33342 with a 405-nm UV laser. Images were collected with pixel dimensions of at least 512×512, using the same laser intensity, exposure and gain settings to allow for direct comparison. For multicolour labelling, images were collected independently.

Quantification of fluorescence intensity was performed using a custom macro developed in the open-source software Fiji (Schindelin et al., 2012, Nat Methods 9, 676-82) (version 1.49r). Briefly, each file was imported with the Bio-Formats plugin to the workspace as an image stack containing multiple channels. Threshold values for each channel were manually inputted and kept constant for all images. The average fluorescence intensity was calculated for each image and divided by the total number of cell nuclei per image. All data was plotted in Prism graphpad and expressed as mean+/−S.E.M of 5 images (where each image contains 8-12 cells).

Example 1—pH-Dependent Binding of C2 Antibodies

In order to identify potential C2 "sweeping" antibodies, 46 anti-C2 monoclonal antibodies from a phage display library were tested for pH-dependent binding to C2 using an ELISA titration assay as described above. The candidate antibodies were initially tested for binding to human C2 at pH 7.4 and pH 5.5. Five of the 46 anti-C2 antibodies showed pH-dependent binding to C2.

FIG. 1 shows that the level of binding of antibodies RF16-191, RF16-203, RF16-214, RF16-226, and RF16-242 to C2 was greatly diminished at pH 5.5 relative to pH 7.4. Whereas, the binding of antibodies RF16-207 and RF216-240 was unaffected by the difference in pH.

To minimize potential immunogenicity, the variable region framework of the pH-dependent anti-C2 antibodies was changed to match that of the closest human germline framework. The resulting antibodies were termed RF16-191G, RF16-203G, RF16-214G, RF16-226G, and RF16-242G. Table 2 shows the corresponding $V_H$ and $V_L$ SEQ ID NOs of the pH-dependent anti-C2 antibodies and their germlined counterparts.

TABLE 2

| pH-dependent C2 binding protein amino acid sequences | | |
|---|---|---|
| Protein | $V_H$ sequence SEQ ID NO | $V_L$ sequence SEQ ID NO |
| RF16-191 | 46 | 50 |
| RF16-191G | 48 | 52 |
| RF16-203 | 47 | 51 |
| RF16-203G | 49 | 53 |
| RF16-214 | 3 | 10 |
| RF16-214G | 3 | 7 |
| RF16-226 | 2 | 9 |
| RF16-226G | 2 | 6 |
| RF16-242 | 5 | 11 |
| RF16-242G | 4 | 8 |

The pH dependent anti-C2 antibodies and their germlined versions were tested for their affinity to C2 at pH 7.3 (neutral pH) and pH 6.0 (early endosome pH) using the SPR methods described above in HBS-EP buffer. Table 3 shows that the majority of these antibodies demonstrated pH-dependent binding to human C2.

TABLE 3

| affinities of pH-dependent anti-C2 antibodies to human C2 in HBS-EP buffer | | |
|---|---|---|
| | Human C2 pH 7.3 $(K_D)$ | Human C2 pH 6.0 $(K_D)$ |
| RF16-191 | 10.9 nM | 13.0 nM |
| RF16-191G | 18.9 nM | 13.0 nM |
| RF16-203 | 2.5 nM | 73 nM* |
| RF16-203G | 506 nM | NT |
| RF16-214 | 31.0 nM | 148 nM |
| RF16-214G | 25.1 nM | 53.9 nM |
| RF16-226 | 11.6 nM | 114 nM |
| RF16-226G | 10.0 nM | 128 nM |
| RF16-242 | 7.0 nM | 16.0 nM |
| RF16-242G | 6.7 nM | 14.0 nM |

*indicates a steady state dissociation constant
"NT" indicates that the antibody was not tested To confirm that the pH-dependent binding to C2 was not buffer specific, the same antibodies were tested for their affinity to C2 at pH 7.3 and 6.0 in a buffer containing 10 mM HEPES, 10 mM MES, 150 mM $(NH_4)_2SO_4$, 3 mM EDTA, 0.05% Tween, 0.1% BSA (referred to as MHAs). This buffer contains ammonium sulfate instead of sodium chloride. Table 4 shows that the antibodies demonstrated pH-dependent binding to C2 in MHAs buffer as well as the HBS-EP buffer used to determine the affinities in Table 3. Table 4 also shows that, in MHAs buffer, the affinities of the antibodies tested for C2 are further decreased as the pH is decreased to 5.8.

TABLE 4 affinities of pH-dependent anti-C2 antibodies to human C2 in MHAs buffer

| | Human C2 pH7.3 ($K_D$) | Human C2 pH6.0 ($K_D$) | Human C2 pH5.8 ($K_D$) |
|---|---|---|---|
| RF16-191 | NT | NT | NT |
| RF16-191G | NT | NT | NT |
| RF16-203 | 12.6 nM | NT | NT |
| RF16-203G | NT | NT | NT |
| RF16-214 | 233 nM | 2.17 µM* | 4.67 µM* |
| RF16-214G | 176 nM | 1.48 µM* | 3.34 µM* |
| RF16-226 | 44 nM | 2.23 µM* | 5.51 µM* |
| RF16-226G | 45.6 nM | 1.9 µM* | 4.06 µM* |
| RF16-242 | 460 nM | 11.58 µM* | 32 µM* |
| RF16-242G | 558 nM | 12 µM* | 47 µM* |

*indicates a steady state dissociation constant
"NT" indicates that the antibody was not tested

Example 2—Species Selectivity

In addition to human C2, the pH dependent anti-C2 antibodies were also tested for their ability to bind to C2 from other mammalian species using the SPR methods described above in order to identify suitable surrogate species for in vivo testing. The antibodies were tested for binding at neutral pH against C2 from cynomolgus monkeys, mice, dogs, rabbits, rats, pigs, and sheep.

In addition to human C2, of the proteins tested, the antibodies only detectably bound to C2 from cynomolgus monkeys ("cyno C2") and mice. The antibodies bound to cyno C2 with a similar affinity to human C2, whereas binding to mouse C2 was very weak. The antibodies also demonstrated pH-dependent binding to cyno C2, as they did for human C2, which is shown in Table 5.

TABLE 5 affinities of pH dependent anti-C2 antibodies to cyno C2 and mouse C2

| | Cyno C2 pH7.3 ($K_D$) | Cyno C2 pH 6.0 ($K_D$) | Mouse C2 pH 7.3 ($K_D$) |
|---|---|---|---|
| RF16-191 | 27.4 nM | 71.3 nM | 303.3 nM |
| RF16-191G | 35.7 nM | 87.3 nM | VWB |
| RF16-203 | 2.82 nM | NT | 153 nM |
| RF16-203G | 485.4 nM | NT | VWB |
| RF16-214 | 46.8 nM | 137.3 nM | 884.6 nM |
| RF16-214G | 41.5 nM | 110.7 nM | VWB |
| RF16-226 | 5.1 nM | 140.9 nM | 159.7 nM |
| RF16-226G | 4.7 nM | 113.6 nM | VWB |
| RF16-242 | 5.2 nM | 134.1 nM | NT |
| RF16-242G | 4.4 nM | 131.9 nM | VWB |

"NT" indicates that the antibody was not tested
"VWB" indicates very weak binding, i.e., a $K_D$ was not able to be determined

Example 3—Complement Inhibition

To assess complement inhibitory activity, the pH-dependent anti-C2 antibodies were tested in the Wieslab® complement assay as described above.

As shown in Table 6, all antibodies tested except RF16-203G inhibited both the classical and lectin human complement pathways with an $IC_{50}$ in the low nanomolar range.

TABLE 6 inhibition of human complement activity; Wieslab ® assay

| | Classical pathway ($IC_{50}$) | Lectin pathway ($IC_{50}$) |
|---|---|---|
| RF16-191 | 1.09 nM | 0.857 nM |
| RF16-191G | 1.64 nM | 1.62 nM |
| RF16-203 | 5.4 nM | 1.29 nM |
| RF16-203G | 2033 nM | 33.2 nM |
| RF16-214 | 18.6 nM | 7.69 nM |
| RF16-214G | 20.3 nM | 6.4 nM |
| RF16-226 | 12.5 nM | 5.6 nM |
| RF16-226G | 5.58 nM | 3.25 nM |
| RF16-242 | 9.19 nM | 2.91 nM |
| RF16-242G | 26.3 nM | 3.19 nM |

As shown in Table 7, the antibodies also inhibited complement activity in the classical and lectin complement pathways when cynomolgus monkey serum was used with only slightly reduced potency relative to human serum (Table 6).

TABLE 7 inhibition of cynomolgus monkey complement activity; Wieslab ® assay

| | Classical pathway ($IC_{50}$) | Lectin pathway ($IC_{50}$) |
|---|---|---|
| RF16-191 | 11.03 nM | 49.2 nM |
| RF16-191G | 8.73 nM | 42.9 nM |
| RF16-203 | 13.27 nM | 112.1 nM |
| RF16-203G | 14130 nM | 5780 nM |
| RF16-214 | 134.1 nM | 361.9 nM |
| RF16-214G | 135 nM | 223.1 nM |
| RF16-226 | 18.8 nM | 140.2 nM |
| RF16-226G | 8.24 nM | 66.5 nM |
| RF16-242 | 8.97 nM | 91.12 nM |
| RF16-242G | 19.3 nM | 274.7 nM |

To confirm the inhibitory activity determined by the Wieslab® assay described above, the antibodies were also tested for their ability to inhibit erythrocyte lysis caused by the human and cynomolgus complement systems, as described above.

The results shown in Table 8 confirm that the anti-C2 antibodies are effective inhibitors of the human and cynomolgus monkey complement systems in vitro.

TABLE 8 inhibition of human and cynomolgus monkey complement activity; hemolysis assay

| | Human - Classical pathway ($IC_{50}$) | Cyno - Classical pathway ($IC_{50}$) |
|---|---|---|
| RF16-191 | 29.4 nM | 188.5 nM |
| RF16-191G | 94 nM | 213.4 nM |
| RF16-203 | 42 nM | 360.8 nM |
| RF16-203G | NI | NI |
| RF16-214 | 241.2 nM | 630.1 nM |
| RF16-214G | 337.2 nM | 396.3 nM |
| RF16-226 | 284.2 nM | 123.5 nM* |
| RF16-226G | 230 nM | 175.7 nM* |

TABLE 8-continued

| inhibition of human and cynomolgus monkey complement activity; hemolysis assay | | |
|---|---|---|
| | Human - Classical pathway (IC$_{50}$) | Cyno - Classical pathway (IC$_{50}$) |
| RF16-242 | 55.4 nM | 641.7 nM |
| RF16-242G | 80.3 nM | 302.3 nM |

"NI" indicates no inhibition detected.

*indicates that the IC$_{50}$ is a mean value from three separate experiments. The remaining values are from a single experiment.

The remaining values are from a single experiment.

Example 4—Epitope Mapping

The anti-C2 antibodies were assessed for their ability to compete with each other with respect to binding to human C2.

Figure 2:
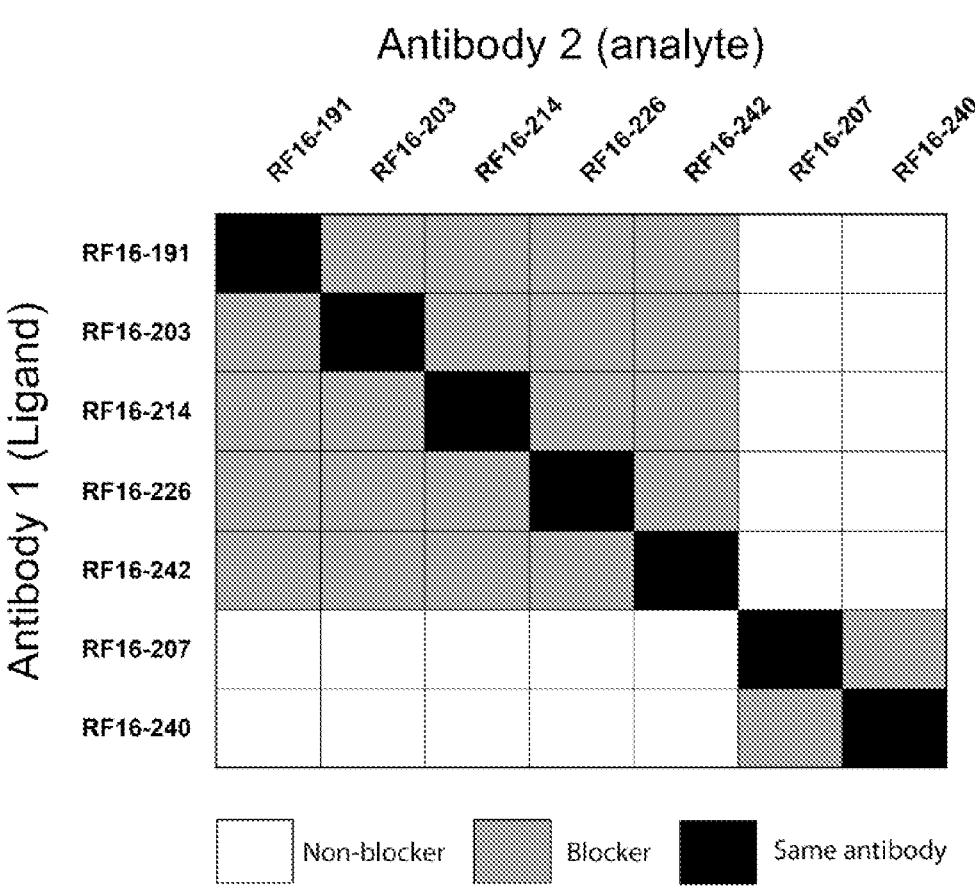
FIG. 2 shows competitive binding of antibody pairs to C2. Colours indicate qualitative binding (white) or non-binding (grey) of an antibody (analyte/mAb2) to C2 captured by an anti-C2 antibody (ligand/mAb1) at the biosensor surface. "Sweeping" antibodies RF16-191, RF16-203, RF16-214, RF16-226 and RF16-242 bound C2 at a distinct epitope relative to "neutralizing" antibodies RF16-207 and RF16-240 but compete with themselves (black) and among each other for binding to C2, indicating their epitopes overlap. Likewise, RF16-207 and RF16-240 bound C2 captured by any sweeping antibody tested but compete with each other for binding to C2.

Qualitative competition binding ("binning") experiments shown in FIG. 2 demonstrate that pH-dependent anti-C2 antibodies RF16-191, RF16-203, RF16-214, RF16-226, and RF16-242 bind to C2 in a competitive manner but do not compete with "neutralizer" anti-C2 antibodies RF16-207 and RF16-240 that do not have pH-dependent binding to C2 (see FIG. 1). This result demonstrates that the pH-dependent anti-C2 antibodies bind to a unique epitope on C2 relative to non-pH dependent binders.

To determine the epitope that the pH-dependent anti-C2 antibodies bind to, a panel of 120 human C2 proteins (WT and 119 mutants) were tested against anti-C2 antibodies RF16-214, RF16-226, and RF16-242. The C2 mutants were designed to test the importance of surface exposed residues for antibody binding. Residues located at either the N-terminal VWA domain or C-terminal protease domain of C were replaced by either alanine or serine and tested for binding against anti-C2 antibodies.

The affinities of RF16-214, RF16-226, and RF16-242 to each of the mutants are shown in Tables 9 to 11 respectively. Biosensor data obtained from these mutants allowed the mapping of residues important for binding.

TABLE 9

| Binding of RF16-214 to C2 alanine mutants | | | |
|---|---|---|---|
| C2 Mutant | K$_D$ (nM) | Fold diff | N |
| WT | 31.0 | 1 | 13 |
| K244A | 97.1 | 3 | 1 |
| E267A | 26.2 | 1 | 1 |
| N268A | 60.8 | 2 | 1 |
| D269A | 17.2 | 1 | 1 |
| F270A | NB | NB | 2 |
| L271A | PB | PB | 2 |
| I272A | 477.2 | 15 | 1 |
| K274A | NB | NB | 2 |
| E275A | PB | PB | 2 |
| S278A | 34.5 | 1 | 1 |
| L279A | 239.9 | 8 | 1 |
| D282A | NB | NB | 2 |
| M316A | 30.2 | 1 | 1 |
| T317A | 27.9 | 1 | 1 |
| I320A | NB | NB | 2 |
| E324A | 27.8 | 1 | 1 |
| N325A | 327.8 | 11 | 1 |
| A326S | 45.5 | 1 | 1 |
| N327A | 205.3 | 7 | 1 |
| Y328A | 195.6 | 6 | 1 |
| K329A | 62.6 | 2 | 1 |
| H331A | NB | NB | 3 |

TABLE 9-continued

| Binding of RF16-214 to C2 alanine mutants | | | |
|---|---|---|---|
| C2 Mutant | K$_D$ (nM) | Fold diff | N |
| N380A | 58.8 | 2 | 1 |
| N403A | 29.6 | 1 | 1 |
| D404A | 77.6 | 3 | 2 |
| G414A | 14.8 | 0 | 1 |
| K415A | 46.0 | 1 | 1 |
| D417A | 56.4 | 2 | 1 |
| V418A | 15.6 | 1 | 2 |
| D419A | 70.7 | 2 | 1 |
| W420A | 34.9 | 1 | 2 |
| N424A | 16.1 | 1 | 1 |
| G427A | 8.8 | 0 | 1 |
| S428A | 58.6 | 2 | 1 |
| K430A | 307.6 | 10 | 2 |
| D431A | 71.8 | 2 | 1 |
| G432A | 26.0 | 1 | 1 |
| E433A | 16.4 | 1 | 1 |
| R434A | 230.0 | 7 | 1 |
| H435A | PB | PB | 2 |
| A436S | 31.2 | 1 | 1 |
| F437A | 380.7 | 12 | 1 |
| I438A | 30.6 | 1 | 2 |
| L439A | 1317.3 | 42 | 1 |
| D441A | 51.5 | 2 | 1 |
| T442A | 70.7 | 2 | 1 |
| K443A | NB | NB | 2 |
| A444S | 20.7 | 1 | 1 |
| H446A | 152.9 | 5 | 1 |
| Q447A | 132.9 | 4 | 1 |
| V448A | 6.9 | 0 | 1 |
| E450A | 626.7 | 20 | 1 |
| H451A | 138.2 | 4 | 1 |
| M452A | 21.3 | 1 | 1 |
| L453A | 1407.1 | 45 | 1 |
| D454A | 111.0 | 4 | 1 |
| V455A | 9.8 | 0 | 1 |
| S456A | 157.2 | 5 | 1 |
| K457A | 41.8 | 1 | 1 |
| V465A | 72.7 | 2 | 1 |
| G466A | 143.8 | 5 | 1 |
| N467A | 77.2 | 2 | 1 |
| S469A | 105.8 | 3 | 1 |
| A470S | 32.8 | 1 | 2 |
| N471A | 32.8 | 1 | 1 |
| A472S | 234.3 | 8 | 1 |
| S473A | 68.7 | 2 | 1 |
| E476A | 58.6 | 2 | 1 |
| R493A | 25.3 | 1 | 1 |
| R519A | 40.0 | 1 | 1 |
| L620A | 30.8 | 1 | 1 |
| G677A | 28.1 | 1 | 1 |
| E686A | 138.8 | 4 | 1 |
| R688A | 96.2 | 3 | 1 |
| F689A | 36.5 | 1 | 1 |

"NB" indicates that no binding was detected

"PB" indicates that affinity could not be determined due to poor binding

TABLE 10

| Binding of RF16-226 to C2 alanine mutants | | | |
|---|---|---|---|
| C2 Mutant | KD (nM) | Fold diff | N |
| WT | 10.1 | 1 | 16 |
| K244A | 22.7 | 2 | 2 |
| E267A | 11.2 | 1 | 1 |
| N268A | 11.8 | 1 | 1 |
| D269A | 13.1 | 1 | 1 |
| F270A | 96.8 | 10 | 1 |
| L271A | 10.8 | 1 | 1 |
| I272A | 10.4 | 1 | 1 |
| K274A | 291.1 | 29 | 1 |
| E275A | 9.4 | 1 | 1 |
| S278A | 9.4 | 1 | 1 |

69

TABLE 10-continued

Binding of RF16-226 to C2 alanine mutants

| C2 Mutant | KD (nM) | Fold diff | N |
|---|---|---|---|
| L279A | 54.4 | 5 | 1 |
| D282A | 8.9 | 1 | 1 |
| M316A | 12.3 | 1 | 1 |
| T317A | 9.0 | 1 | 1 |
| I320A | 116.4 | 12 | 1 |
| E324A | 12.2 | 1 | 1 |
| N325A | 51.3 | 5 | 1 |
| A326S | 13.2 | 1 | 1 |
| N327A | 67.4 | 7 | 2 |
| Y328A | 78.4 | 8 | 1 |
| K329A | 25.6 | 3 | 1 |
| H331A | NB | NB | 3 |
| N380A | 15.1 | 2 | 1 |
| N403A | 10.5 | 1 | 1 |
| D404A | 12.8 | 1 | 2 |
| G414A | 11.2 | 1 | 1 |
| K415A | 11.7 | 1 | 1 |
| D417A | 17.9 | 2 | 1 |
| V418A | 8.0 | 1 | 1 |
| D419A | 17.6 | 2 | 1 |
| W420A | 15.6 | 2 | 2 |
| N424A | 3.2 | 0 | 1 |
| G427A | 4.2 | 0 | 1 |
| S428A | 18.8 | 2 | 1 |
| K430A | 62.0 | 6 | 1 |
| D431A | 43.4 | 4 | 1 |
| G432A | 6.6 | 1 | 1 |
| E433A | 2.6 | 0 | 1 |
| R434A | 141.5 | 14 | 1 |
| H435A | 24.3 | 2 | 1 |
| A436S | 6.2 | 1 | 1 |
| F437A | 260.1 | 26 | 1 |
| I438A | 8.7 | 1 | 2 |
| L439A | 118.0 | 12 | 1 |
| D441A | 63.9 | 6 | 1 |
| T442A | 23.7 | 2 | 1 |
| K443A | NB | NB | 2 |
| A444S | 19.8 | 2 | 1 |
| H446A | 16.3 | 2 | 1 |
| Q447A | 5.4 | 1 | 1 |
| V448A | 4.4 | 0 | 1 |
| E450A | 4.2 | 0 | 1 |
| H451A | 105.2 | 11 | 1 |
| M452A | 4.1 | 0 | 1 |
| L453A | 29.9 | 3 | 1 |
| D454A | 247.1 | 25 | 1 |
| V455A | 9.0 | 1 | 1 |
| S456A | 71.8 | 7 | 1 |
| K457A | PB | PB | 2 |
| V465A | 17.1 | 2 | 1 |
| G466A | 32.4 | 3 | 1 |
| N467A | 19.7 | 2 | 1 |
| S469A | 28.2 | 3 | 1 |
| A470S | 7.8 | 1 | 1 |
| N471A | 9.7 | 1 | 1 |
| A472S | 53.0 | 5 | 1 |
| S473A | 14.2 | 1 | 1 |
| E476A | 19.6 | 2 | 1 |
| T483A | 5.5 | 1 | 1 |
| K485A | 12.5 | 1 | 1 |
| P486A | 11.1 | 1 | 1 |
| K487A | 93.0 | 9 | 1 |
| Q489A | 104.3 | 10 | 1 |
| E490A | 15.6 | 2 | 1 |
| T491A | 15.5 | 2 | 1 |
| R493A | 24.3 | 2 | 2 |
| R510A | 109.6 | 11 | 1 |
| D511A | 31.2 | 3 | 1 |
| R519A | 11.2 | 1 | 1 |
| G530A | 16.7 | 2 | 1 |
| K531A | 12.1 | 1 | 1 |
| E532A | 17.2 | 2 | 1 |
| K550A | 15.0 | 1 | 1 |
| E556A | 5.9 | 1 | 1 |
| Y558A | 158.0 | 16 | 1 |
| D561A | 101.5 | 10 | 1 |

70

TABLE 10-continued

Binding of RF16-226 to C2 alanine mutants

| C2 Mutant | KD (nM) | Fold diff | N |
|---|---|---|---|
| L620A | 11.1 | 1 | 1 |
| N621A | 51.5 | 5 | 2 |
| E645A | 14.0 | 1 | 1 |
| T647A | 147.1 | 15 | 1 |
| M648A | 203.3 | 20 | 1 |
| P650A | 18.3 | 2 | 1 |
| K676S | 16.3 | 2 | 1 |
| G677A | 8.7 | 1 | 1 |
| E686A | 47.3 | 5 | 2 |
| R688A | 25.3 | 3 | 1 |
| F689A | 9.3 | 1 | 1 |
| L701A | 165.0 | 16 | 1 |
| Y702A | 106.5 | 11 | 1 |
| N703A | 292.4 | 29 | 1 |
| P704A | 120.2 | 12 | 1 |
| L706A | 228.7 | 23 | 1 |
| G707A | 19.4 | 2 | 1 |
| S708A | 21.1 | 2 | 1 |
| A709S | 126.8 | 13 | 1 |
| D710A | 97.4 | 10 | 1 |
| K711A | 49.6 | 5 | 1 |
| S713A | 19.0 | 2 | 1 |
| R714A | 53.0 | 5 | 1 |
| K715A | 16.2 | 2 | 1 |
| A717S | 405.9 | 41 | 1 |
| P718A | 15.2 | 2 | 1 |
| R719A | 8.5 | 1 | 1 |
| S720A | 14.6 | 1 | 1 |
| K721A | 99.9 | 10 | 1 |
| V722A | 95.2 | 10 | 1 |
| P723A | 121.9 | 12 | 1 |
| P724A | 397.1 | 40 | 1 |

"NB" indicates that no binding was detected
"PB" indicates that affinity could not be determined due to poor binding

TABLE 11

Binding of RF16-242 to C2 alanine mutants

| C2 Mutant | KD (nM) | Fold diff | N |
|---|---|---|---|
| WT | 7.0 | 1 | 9 |
| K244A | 26.2 | 4 | 1 |
| E267A | 12.1 | 2 | 1 |
| N268A | 14.8 | 2 | 1 |
| D269A | 12.9 | 2 | 1 |
| F270A | 104.4 | 15 | 1 |
| L271A | 6.9 | 1 | 1 |
| I272A | 10.3 | 1 | 1 |
| K274A | 86.9 | 12 | 1 |
| E275A | 42.8 | 6 | 1 |
| S278A | 6.5 | 1 | 1 |
| L279A | 49.2 | 7 | 1 |
| D282A | 8.0 | 1 | 1 |
| M316A | 10.1 | 1 | 1 |
| T317A | 5.9 | 1 | 1 |
| I320A | 73.5 | 10 | 1 |
| E324A | 10.7 | 2 | 1 |
| N325A | 39.9 | 6 | 1 |
| A326S | 9.9 | 1 | 1 |
| N327A | 37.5 | 5 | 1 |
| Y328A | 45.4 | 6 | 1 |
| K329A | 14.8 | 2 | 1 |
| H331A | 191.2 | 27 | 2 |
| N380A | 10.2 | 1 | 1 |
| N403A | 8.2 | 1 | 1 |
| D404A | 16.4 | 2 | 1 |
| G414A | 4.2 | 1 | 1 |
| K415A | 4.1 | 1 | 1 |
| D417A | 23.0 | 3 | 1 |
| V418A | 6.8 | 1 | 2 |
| D419A | 10.5 | 2 | 1 |
| W420A | 13.2 | 2 | 2 |

TABLE 11-continued

| Binding of RF16-242 to C2 alanine mutants | | | |
| --- | --- | --- | --- |
| C2 Mutant | KD (nM) | Fold diff | N |
| N424A | 5.7 | 1 | 1 |
| G427A | 4.0 | 1 | 1 |
| S428A | 18.6 | 3 | 1 |
| K430A | 91.0 | 13 | 1 |
| D431A | 22.9 | 3 | 1 |
| G432A | 8.8 | 1 | 1 |
| E433A | 3.0 | 0 | 1 |
| R434A | 98.9 | 14 | 1 |
| H435A | 62.5 | 9 | 1 |
| A436S | 4.9 | 1 | 1 |
| F437A | 107.1 | 15 | 1 |
| I438A | 8.7 | 1 | 1 |
| L439A | 170.1 | 24 | 1 |
| D441A | 113.9 | 16 | 1 |
| T442A | 18.0 | 3 | 1 |
| K443A | NB | NB | 2 |
| A444S | 22.4 | 3 | 1 |
| H446A | 16.1 | 2 | 1 |
| Q447A | 26.0 | 4 | 1 |
| V448A | 5.0 | 1 | 1 |
| E450A | 20.3 | 3 | 1 |
| H451A | 21.3 | 3 | 1 |
| M452A | 5.3 | 1 | 1 |
| L453A | 6.8 | 1 | 1 |
| D454A | 35.4 | 5 | 2 |
| V455A | 5.9 | 1 | 1 |
| S456A | 59.8 | 9 | 1 |
| K457A | 233.0 | 33 | 1 |
| V465A | 16.3 | 2 | 1 |
| G466A | 24.9 | 4 | 1 |
| N467A | 13.4 | 2 | 1 |
| S469A | 21.4 | 3 | 1 |
| A470S | 5.0 | 1 | 2 |
| N471A | 9.2 | 1 | 1 |
| A472S | 51.1 | 7 | 1 |
| S473A | 15.5 | 2 | 1 |
| E476A | 14.0 | 2 | 1 |
| R493A | 7.2 | 1 | 1 |
| R519A | 7.6 | 1 | 1 |
| L620A | 8.0 | 1 | 1 |
| G677A | 6.8 | 1 | 1 |
| E686A | 32.6 | 5 | 1 |
| R688A | 17.3 | 2 | 1 |
| F689A | 6.3 | 1 | 1 |

"NB" indicates that no binding was detected
"PB" indicates that affinity could not be determined due to poor binding Tables 9 to 11 show that the epitope of pH-dependent anti-C2 antibodies RF16-214, RF16-226 and RF16-242 is mostly confined to the VWA domain (amino acids 254 to 452). In particular, the lysine at position 443, histidine at position 331 and lysine at position 457 appear to be very important for binding of the pH-dependent anti-C2 antibodies to C2. RF16-226 is also partially sensitive to mutations of protease domain (amino acids 464-744) residues suggesting that the stability of its epitope requires both domains.

Mutation of the histidine at position 331 and the lysine at position 443 had a major impact (>20-fold reduction in KD) on the binding affinity of all three antibodies and likely explains the sensitivity of these antibodies to changes in local pH.

Example 5—Increasing Affinity to FcRn

In order to enhance the recycling of the pH-dependent anti-C2 antibodies, several residues in the Fc regions of these antibodies, which are involved in binding to FcRn, were mutated to increase their affinity to FcRn at pH 6.0 (early endosomal pH) and 7.3 (neutral pH). Binding to both human and cynomolgus monkey FcRn was tested using the SPR methods described above.

Tables 12 and 13 show the resulting affinities of the RF16-226 Fc mutants for human and cynomolgus monkey FcRn respectively. Similar results were obtained for RF16-214 and RF16-242 (data not shown).

TABLE 12

| Affinity of RF16-226 Fc mutants to human FcRn | | |
| --- | --- | --- |
| | $K_D$ (nM) at pH 6.0 | $K_D$ (nM) at pH 7.3 |
| WT | 3800 | >10 μM |
| I253A | >10 μM | >10 μM |
| M428L, N434A | 640 | >10 μM |
| M252Y, S254T, T256E | 680 | >10 μM |
| M252Y, N286E, N434Y | 22 | 3300 |
| M252Y, V308P, N434Y | 10 | 1200 |

TABLE 13

| Affinity of RF16-226 Fc mutants to cynomolgus monkey FcRn | | |
| --- | --- | --- |
| | $K_D$ (nM) at pH 6.0 | $K_D$ (nM) at pH 7.3 |
| WT | 2100 | >10 μM |
| I253A | >10 μM | >10 μM |
| M428L, N434A | 420 | >10 μM |
| M252Y, S254T, T256E | 450 | >10 μM |
| M252Y, N286E, N434Y | 19 | 2200 |
| M252Y, V308P, N434Y | 8.7 | 1100 |

Example 6—Neutralisation Mechanism of Action

A representative pH-dependent anti-C2 antibody, RF16-226, was assessed for its ability to inhibit C1s-mediated cleavage of C2 to determine, at least in part, its mechanism of action of complement inhibition. Human C2 was incubated with RF16-226 at room temperature for 30 mins and subsequently varying concentrations of C1s were added to the mixture before incubation for a further 1 h. An SDS-PAGE gel was run to analyse the amount of C2a (the larger enzymatically active fragment of C2) produced by proteolytic cleavage of C2 by C1s.

Figure 3:
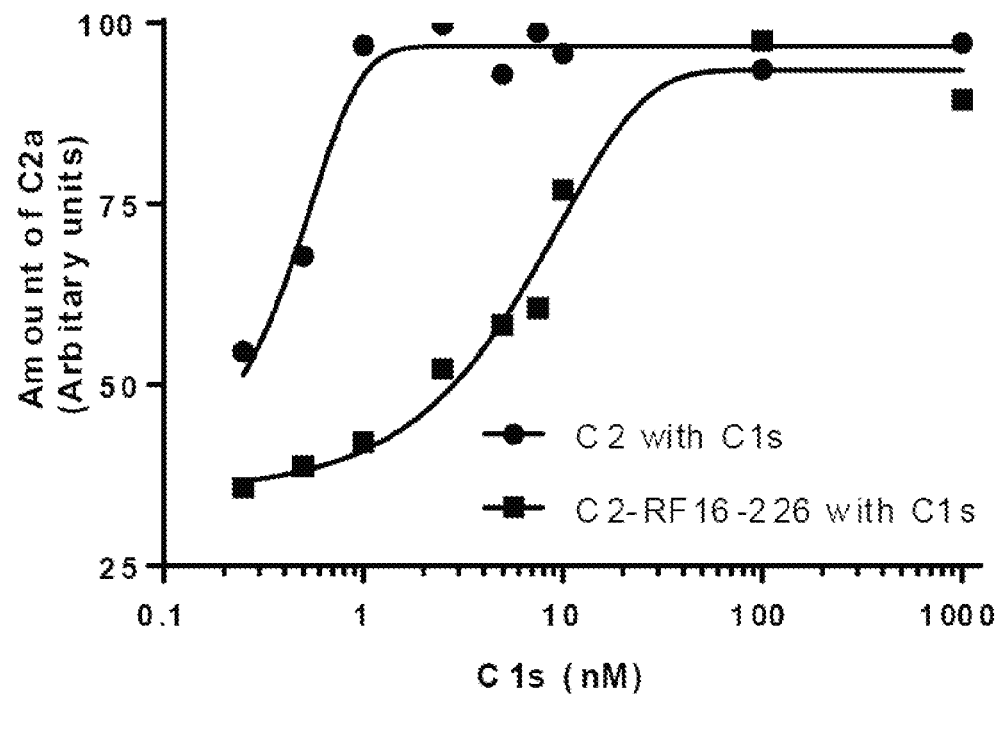
FIG. 3 is a graph illustrating the inhibition of C1s-mediated proteolytic degradation of C2 by pH-dependent anti-C2 antibody RF16-226. Human C2 was incubated with RF16-226 at room temperature for 30 mins and subsequently varying concentrations of C1s (0-1000 nM) was added to the mixture before incubation for a further 1 h. A 4-12% SDS-PAGE gel was run to analyse the amount of C2a produced by proteolytic cleavage of C2 by C1s. The bands were quantified based on their intensity and size and the mean intensities were plotted against the concentration of C1s and curve-fitted to a sigmoidal 4-parameter logistic curve using Graphpad Prism.

FIG. 3 shows that the antibody RF16-226 was able to inhibit the proteolytic activity of C1s resulting in protection of C2 from activation. The data was fitted to a sigmoidal four parameter logistic curve where X is log (concentration of C1s). The log IC50 for inhibition by RF16-226 as calculated from this fitting was 50.3 nM. Notably, inhibition of C2 activation by RF16-226 was a C1s concentration-dependent phenomenon.

The inhibitory effect of RF16-226 on C1s activity shown in FIG. 3 was also determined for the germlined version of this antibody, RF16-226G. In this experiment, 0.2 μM human C2 was incubated with 0.25 μM RF16-226G (or control antibody RF16-240) at room temperature for 30 mins and subsequently 2.5 nM C1s was added to the mixture before incubation for a further 1 h. An SDS-PAGE gel was run to analyse the amount of C2b (the smaller inactive fragment of C2) produced by proteolytic cleavage of C2 by C1s.

Figure 4:
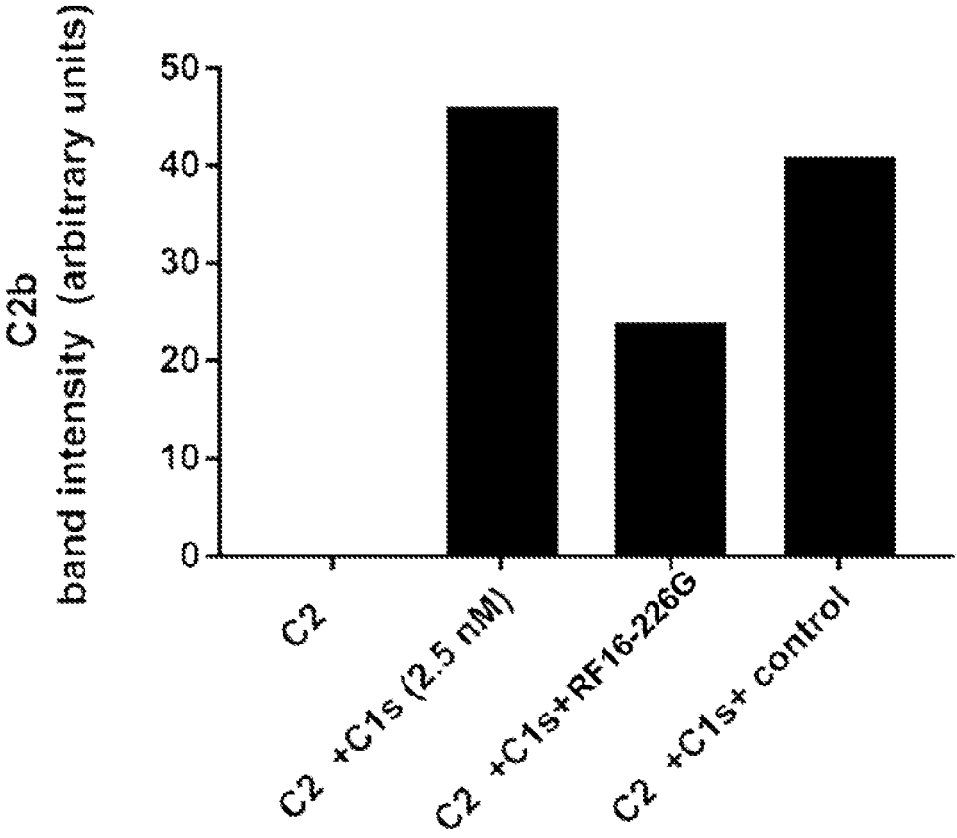
FIG. 4 is a graph illustrating the inhibition of C1s-mediated proteolytic degradation of C2 by pH-dependent anti-C2 antibody RF16-226G. 0.2 μM human C2 was incubated with 0.25 μM RF16-226G (or control antibody RF16-240) at room temperature for 30 mins and subsequently 2.5 nM C1s was added to the mixture before incubation for a further 1 h. A 4-12% SDS-PAGE gel was run to analyse the amount of C2b produced by proteolytic cleavage of C2 by C1s. The bands on the SDS-PAGE gel were quantified based on their intensity and size.

FIG. 4 shows that the antibody RF16-226G inhibited the proteolytic activity of C1s, as determined by the amount of C2b produced.

Example 7—Confirmation of Sweeping Activity

The sweeping activity of RF16-226G and RF16-226G YPY (i.e., the RF16-226G antibody with the M252Y, V308P and N434Y Fc mutations described in Example 5) was assessed in vitro with cellular assays using 293-F cells stably expressing human FcRn and $\beta_2$-microglobulin (Chia et al., 2018, J Biol Chem 293, 6363-6373). The sweeping activity of these antibodies was assessed against a non-pH dependent C2-binding antibody RF16-207 as a control. Cells were simultaneously pulsed with fluorescently-labelled C2 (C2-AF488) and control, RF16-226G or RF16-226G YPY anti-C2 antibodies (molar ratio of C2:antibody, 8:1) at pH 7 (FIGS. 5A and 5B) or pH 5.5 (FIGS. 5C and 5D). Fluorescence corresponding to C2 is depicted in FIGS. 5A and 5C and fluorescence corresponding to the respective anti-C2 antibody is depicted in FIGS. 5B and 5D.

Figure 5:
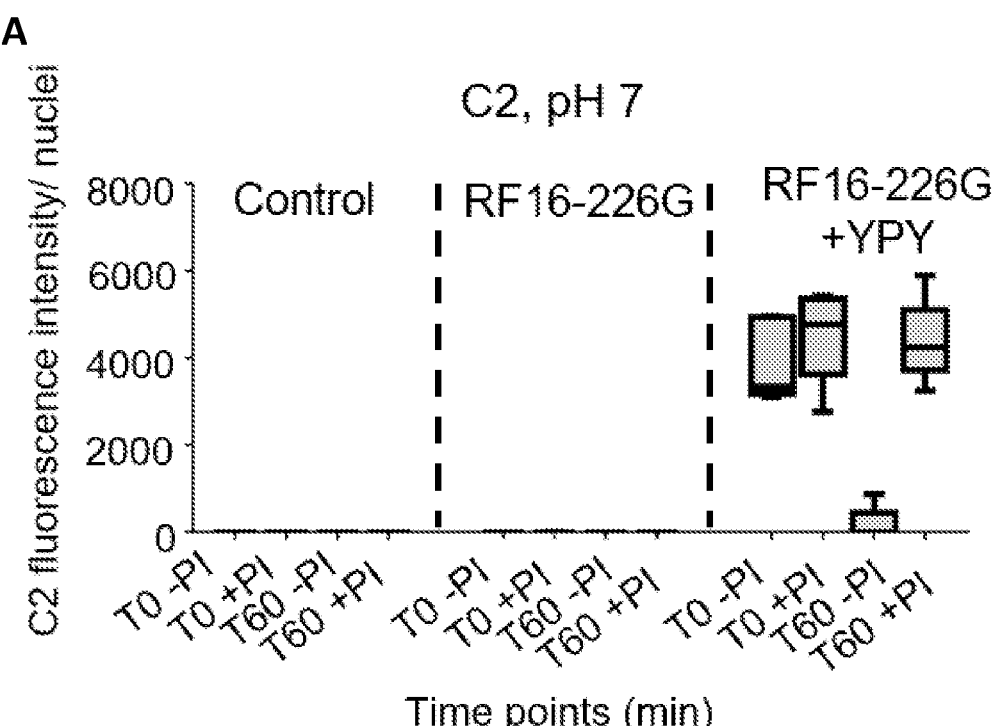
FIG. 5 is a series of graphs showing the sweeping activity of anti-C2 antibodies at pH 7 and pH 5.5. Freestyle™ 293 cells stably expressing human FcRn and β2-microglobulin were incubated with C2-AF488 and anti-C2 antibodies (RF16-207 "control"; RF16-226G; RF16-226G+YPY) at either pH 5.5 or pH 7 in the presence or absence of protease inhibitors ("+PI" or "-PI") in serum-free media (SFM) for 10 min. Cells were washed in PBS and C2-AF488 and anti-C2 antibodies (were chased in C-RPMI containing either protease inhibitors (+PI) or DMSO (-PI) for 0 min or 60 min. Fluorescent intensity corresponding to C2 (A, C) or the anti-C2 antibodies (B, D) in the Freestyle™ 293 cells was quantified at 0 and 60 min chase time points at either pH 7 (A, B) or pH 5.5 (C, D). Graphs shown are representative of two independent experiments where an average fluorescent intensity value was determined from 5 images (each containing 8 or more cells) for each time point. Error bars show mean+/-sem.
Figure 5:
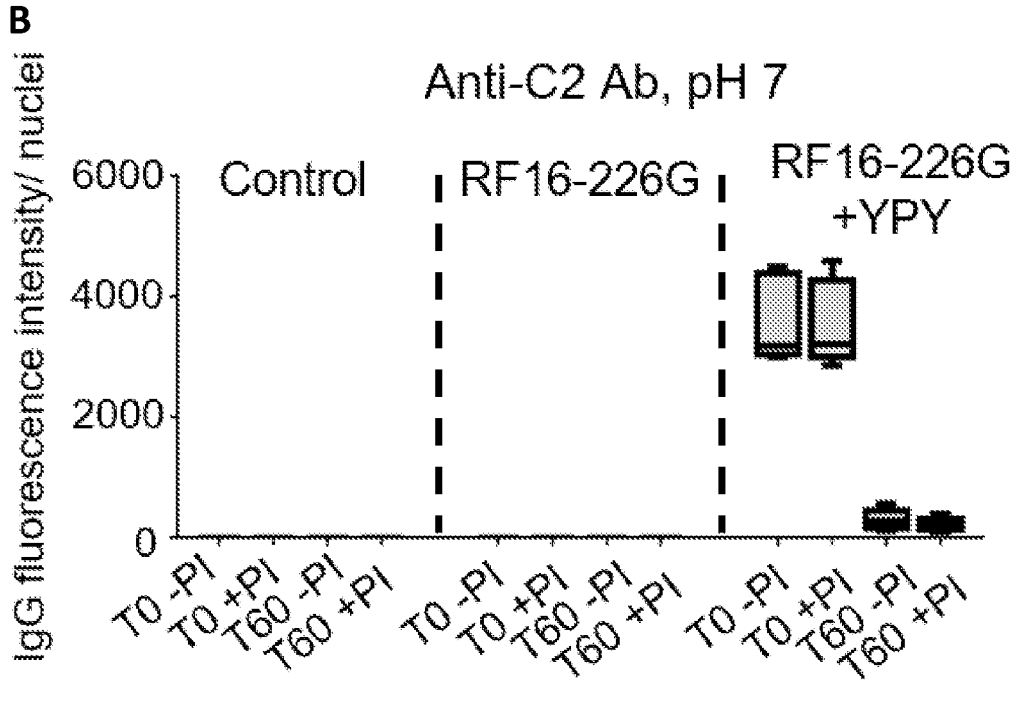
Figure 5:
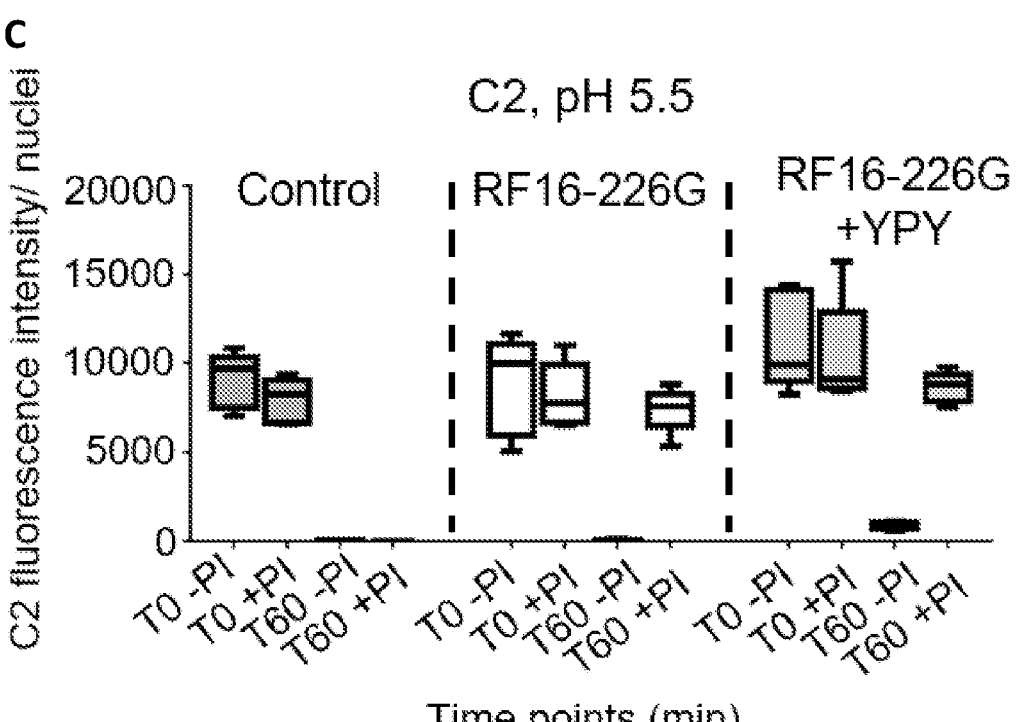
Figure 5:
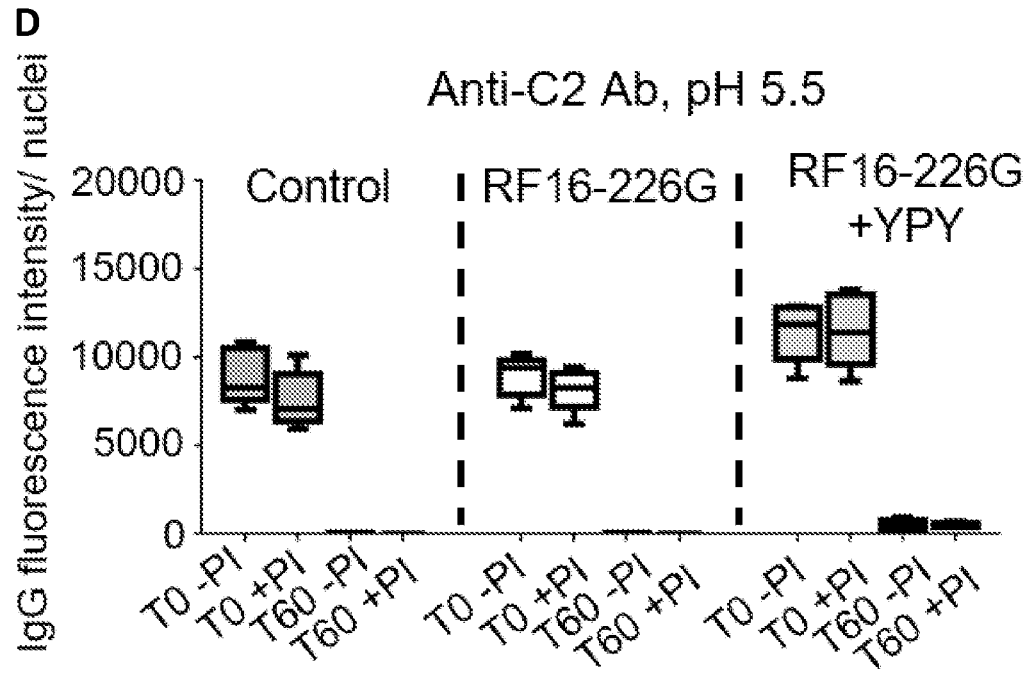

At pH 7, when C2 was co-administered with the control or RF16-226G anti-C2 antibodies there was no uptake of C2 or the anti-C2 antibodies (FIGS. 5A and 5B respectively) into the cells, reflecting the minimal binding of these two antibodies to FcRn at neutral pH. In contrast, C2 was efficiently internalised when co-administered with the anti-C2 RF16-226G YPY antibody (FIGS. 5A and 5B), which can bind to FcRn at pH 7. Significant co-localisation was evident between C2 and RF16-226G+YPY, suggesting these molecules were taken up as a complex, and C2 was not internalised in the absence of anti-C2 antibody (data not shown): After a 60 min chase, very little C2 or RF16-226G YPY was detected in cells (FIGS. 5A and 5B). However, in the presence of a cocktail of protease inhibitors ("+PI" in FIG. 5), where rescue of the signal would indicate lysosomal degradation, the signal for C2 (FIG. 5A), but not RF16-226G YPY (FIG. 5B), was retained. These results are consistent with a sweeping activity for RF16-226G YPY, whereby C2 is internalised in complex RF16-226G YPY via the FcRn receptor at pH 7, followed by release of C2 within the acidic endosome and subsequent lysosomal degradation, whilst RF16-226G YPY is recycled back to the cell surface.

Pulse-chase experiments were also conducted at pH 5.5 to facilitate FcRn-mediated uptake of all antibodies and complexes (FIGS. 5C and 5D). Under these conditions, there was significant uptake of C2-AF488 and all respective antibodies after a 10 min pulse. Following a further 60 min chase, the fluorescence of C2-AF488 and all anti-C2 antibodies almost completely diminished. Addition of protease inhibitors rescued the C2-AF488 fluorescence when co-administered with RF16-226G and RF16-226G YPY antibodies, suggesting lysosomal degradation of C2 under these conditions, but not when co-administered with the control antibody (FIGS. 5C and 5D). The fluorescence for all antibodies was not rescued with the addition of protease inhibitors, suggesting recycling of all of the antibodies via FcRn. Overall, these results suggest that the RF16-226G and RF16-226G YPY antibodies are able to release C2 within the acidic endosomal compartments for subsequent lysosomal degradation, due to their pH-dependent binding of C2.

Example 8—Comparison to Other Anti-C2 Antibodies

The binding properties of the pH-dependent anti-C2 antibodies disclosed herein were compared against antibodies "Ch13" and "Ch5F2.4", which are described in WO 2014/189378.

Binding Competition

Antibodies RF16-226, RF16-240, Ch5F2.4 and Ch13 were analysed in pairwise binding (ie. binning) experiments using human C2 zymogen (huC2) as a binding partner to determine if these antibodies competed for binding. Binding data was analysed in a qualitative manner since positive binding responses indicate complex formation by non-competitive antibodies binding to huC2 (indicated in white in FIG. 6). Likewise, negative binding responses indicate that an antibody cannot bind huC2 captured by an anti-C2 mAb tethered at the chip surface; (indicated in grey in FIG. 6). Pairwise analysis also included the same antibody tested as ligand and analyte (indicated in black in FIG. 6).

Figure 6:
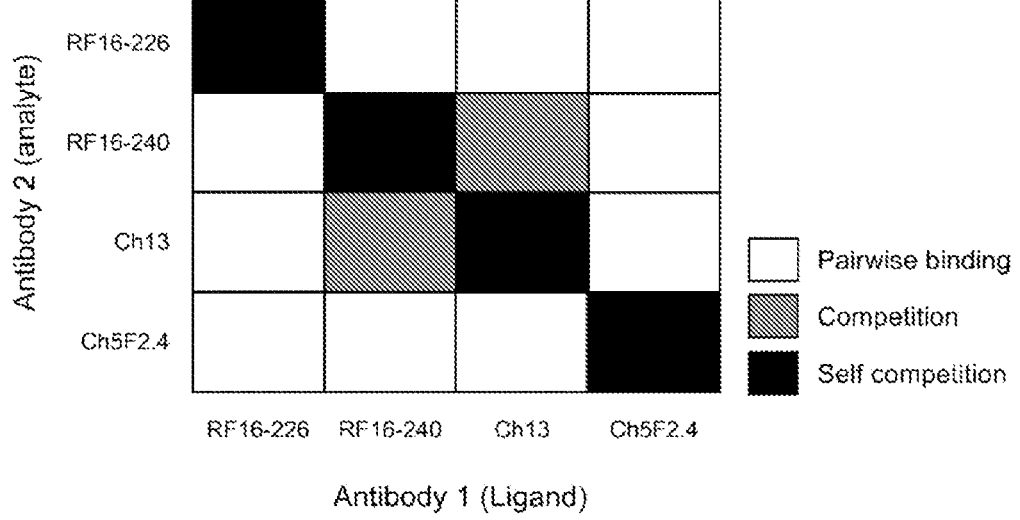
FIG. 6 shows competitive binding of antibody pairs to human C2 zymogen at neutral pH in the presence of 2 mM Ca$^{+2}$. Colours indicate qualitative non-competitive binding (white) by a secondary antibody (antibody 2/analyte) injected over human C2 bound to a captured antibody (antibody 1/ligand). Absence of binding responses for antibody 2 indicates competition with antibody 1 (i.e. non-binding, grey) at the biosensor surface or combinations where an antibody is tested both as analyte and ligand (black).

The binning experiment described here used similar design as that described in Example 4. The major difference was the use of 2 mM calcium chloride instead of 3 mM EDTA, because calcium is required for optimal binding of Ch5F2.4 to C2. FIG. 6 shows that antibody pairs RF16-226/RF16-240, RF16-226/Ch5F2.4, RF16-240/Ch5F2.4 and Ch5F2.4/Ch13 do not compete for binding to huC2, suggesting that their epitopes do not overlap. Only antibodies RF16-240 and Ch13 showed competition in pairwise binding experiments when tested in both orientations (ie. as ligand or analyte mAbs), suggesting that their epitopes overlap.

Effect of Calcium on C2 Binding

The effect of calcium on C2 binding of RF16-226, RF16-226 YTE (Fc mutations M252Y, S254T, T256E), RF16-226 YEY (M252Y, N286E, N434Y), RF16-226 YPY (M252Y, V308P, N434Y), Ch5F2.4 and Ch13 was determined with the addition of calcium chloride to the SPR running buffer. Calcium concentrations ranged from zero (i.e. no added calcium, control) to near physiological levels (0.02, 0.2 and 2 mM $CaCl_2 \cdot 2H_2O$, MW 147.02 Da).

As was found in Example 1, human complement C2 zymogen (huC2) binding to RF16-226 was pH sensitive, ranging from $K_D$ ~10 nM at neutral (pH 7.3) to $K_D$ ~95 nM in acidic (pH 6) conditions (Table 14 and 15). The addition of calcium did not have a significant impact on the binding affinity of huC2 (Table 14 and 15), suggesting the mode of action of this antibody is not dependent on $Ca^{2+}$ ion concentration.

Activated human C2 (huC2a) did not bind RF16-226 either in the presence or absence of calcium.

TABLE 14

Binding kinetics of huC2 to RF16-226 antibody measured in presence of increasing concentrations of Calcium Chloride (Ca2+) at neutral conditions (pH 7.3).

| Analyte | Ligand | $k_a$ (1/Ms) | $k_d$ (1/s) | $K_D$ (nM) | SEM (nM) | N |
|---|---|---|---|---|---|---|
| huC2 0 mM $Ca^{2+}$ | RF16-226 (WT) | $5.46 \times 10^5$ | $4.99 \times 10^{-3}$ | 9.2 | 0.3 | 6 |
| huC2 20 mM $Ca^{2+}$ | RF16-226 (WT) | $5.69 \times 10^5$ | $5.70 \times 10^{-3}$ | 10.2 | 0.9 | 6 |
| huC2 200 mM $Ca^{2+}$ | RF16-226 (WT) | $6.31 \times 10^5$ | $5.90 \times 10^{-3}$ | 9.3 | 0.4 | 6 |
| huC2 2000 mM $Ca^{2+}$ | RF16-226 (WT) | $5.61 \times 10^5$ | $6.20 \times 10^{-3}$ | 11.1 | 0.5 | 6 |

TABLE 15

Steady-state binding affinity of huC2 to RF16-226 antibody measured in
presence of increasing concentrations of Calcium Chloride (Ca2+)
at acidic pH (pH 6.0).

| Analyte | Ligand | $K_D$* (nM) | SEM (nM) | N |
|---|---|---|---|---|
| huC2 0 mM $Ca^{2+}$ | RF16-226 (WT) | 93.6 | 1.2 | 3 |
| huC2 20 mM $Ca^{2+}$ | RF16-226 (WT) | 87.4 | 2.2 | 3 |
| huC2 200 mM $Ca^{2+}$ | RF16-226 (WT) | 94.2 | 3.0 | 3 |
| huC2 2000 mM $Ca^{2+}$ | RF16-226 (WT) | 111.2 | 4.3 | 3 |

*Steady state $K_D$

Fc mutations YTE (M252Y, S254T, T256E), YEY (M252Y, N286E, N434Y) and YPY (M252Y, V308P, N434Y) did not impact the affinity of RF16-226 to human C2 (Tables 16 to 21). Overall, huC2 bound RF16-226 and its Fc variants at affinities of $K_D$ ~9 nM at pH 7 and $K_D$ ~80 nM at pH 6. Calcium did not impact the binding of huC2 to any of these antibodies (Tables 16 to 21).

TABLE 16

Binding kinetics of huC2 to RF16-226 YTE antibody measured in presence
of increasing concentrations of Calcium Chloride (Ca2+) at neutral conditions (pH 7.3).

| Analyte | Ligand | $k_a$ (1/Ms) | $k_d$ (1/s) | $K_D$ (nM) | SEM (nM) | N |
|---|---|---|---|---|---|---|
| huC2 0 mM $Ca^{2+}$ | RF16-226 YTE | $5.84 \times 10^5$ | $4.95 \times 10^{-3}$ | 8.5 | n/a | 1 |
| huC2 20 mM $Ca^{2+}$ | RF16-226 YTE | $6.57 \times 10^5$ | $5.21 \times 10^{-3}$ | 7.9 | n/a | 1 |
| huC2 200 mM $Ca^{2+}$ | RF16-226 YTE | $6.53 \times 10^5$ | $5.43 \times 10^{-3}$ | 8.3 | n/a | 1 |
| huC2 2000 mM $Ca^{2+}$ | RF16-226 YTE | $6.01 \times 10^5$ | $5.92 \times 10^{-3}$ | 9.9 | n/a | 1 |

TABLE 17

Steady-state binding affinity of huC2 to RF16-226 YTE antibody
measured in presence of increasing concentrations of Calcium
Chloride (Ca2+) at acidic pH (pH 6.0).

| Analyte | Ligand | $K_D$* (nM) | SEM (nM) | N |
|---|---|---|---|---|
| huC2 0 mM $Ca^{2+}$ | RF16-226 YTE | 74.3 | n/a | 1 |
| huC2 20 mM $Ca^{2+}$ | RF16-226 YTE | 71.0 | n/a | 1 |
| huC2 200 mM $Ca^{2+}$ | RF16-226 YTE | 74.6 | n/a | 1 |
| huC2 2000 mM $Ca^{2+}$ | RF16-226 YTE | 92.8 | n/a | 1 |

*Steady state $K_D$

TABLE 18

Binding kinetics of huC2 to RF16-226 YEY antibody measured in presence
of increasing concentrations of Calcium Chloride (Ca2+) at neutral conditions (pH 7.3).

| Analyte | Ligand | $k_a$ (1/Ms) | $k_d$ (1/s) | $K_D$ (nM) | SEM (nM) | N |
|---|---|---|---|---|---|---|
| huC2 0 mM $Ca^{2+}$ | RF16-226 YEY | $6.01 \times 10^5$ | $5.21 \times 10^{-3}$ | 8.7 | n/a | 1 |
| huC2 20 mM $Ca^{2+}$ | RF16-226 YEY | $5.85 \times 10^5$ | $5.16 \times 10^{-3}$ | 8.8 | n/a | 1 |
| huC2 200 mM $Ca^{2+}$ | RF16-226 YEY | $5.73 \times 10^5$ | $5.27 \times 10^{-3}$ | 9.2 | n/a | 1 |
| huC2 2000 mM $Ca^{2+}$ | RF16-226 YEY | $5.38 \times 10^5$ | $5.73 \times 10^{-3}$ | 10.7 | n/a | 1 |

TABLE 19

Steady-state binding affinity of huC2 to RF16-226 YEY antibody
measured in presence of increasing concentrations of Calcium
Chloride (Ca2+) at acidic pH (pH 6.0).

| Analyte | Ligand | $K_D$* (nM) | SEM (nM) | N |
|---|---|---|---|---|
| huC2 0 mM Ca$^{2+}$ | RF16-226 YEY | 84.0 | n/a | 1 |
| huC2 20 mM Ca$^{2+}$ | RF16-226 YEY | 81.9 | n/a | 1 |
| huC2 200 mM Ca$^{2+}$ | RF16-226 YEY | 86.9 | n/a | 1 |
| huC2 2000 mM Ca$^{2+}$ | RF16-226 YEY | 104.8 | n/a | 1 |

*Steady state $K_D$

TABLE 20

Binding kinetics of huC2 to RF16-226 YPY antibody measured in presence
of increasing concentrations of Calcium Chloride (Ca2+) at neutral conditions (pH 7.3).

| Analyte | Ligand | $k_a$ (1/Ms) | $k_d$ (1/s) | $K_D$ (nM) | SEM (nM) | N |
|---|---|---|---|---|---|---|
| huC2 0 mM Ca$^{2+}$ | RF16-226 YPY | $5.78 \times 10^5$ | $4.93 \times 10^{-3}$ | 8.5 | n/a | 1 |
| huC2 20 mM Ca$^{2+}$ | RF16-226 YPY | $6.26 \times 10^5$ | $5.26 \times 10^{-3}$ | 8.4 | n/a | 1 |
| huC2 200 mM Ca$^{2+}$ | RF16-226 YPY | $6.12 \times 10^5$ | $5.39 \times 10^{-3}$ | 8.8 | n/a | 1 |
| huC2 2000 mM Ca$^{2+}$ | RF16-226 YPY | $5.72 \times 10^5$ | $5.84 \times 10^{-3}$ | 10.2 | n/a | 1 |

TABLE 21

Steady-state binding affinity of huC2 to RF16-226 YPY antibody
measured in presence of increasing concentrations of Calcium
Chloride (Ca2+) at acidic pH (pH 6.0).

| Analyte | Ligand | $K_D$* (nM) | SEM (nM) | N |
|---|---|---|---|---|
| huC2 0 mM Ca$^{2+}$ | RF16-226 YPY | 87.3 | n/a | 1 |
| huC2 20 mM Ca$^{2+}$ | RF16-226 YPY | 83.1 | n/a | 1 |
| huC2 200 mM Ca$^{2+}$ | RF16-226 YPY | 91.9 | n/a | 1 |
| huC2 2000 mM Ca$^{2+}$ | RF16-226 YPY | 102.4 | n/a | 1 |

*Steady state $K_D$

In contrast to RF16-226, Ch5F2.4 binding to C2 was sensitive to calcium concentration (Tables 22 and 23). The steady-state affinity of huC2 to Ch5F2.4 was comparable under neutral (pH 7.3, $K_D$ ~14 nM) and acidic (pH 6, $K_D$ ~22 nM) conditions when calcium is present at near physiological levels (ie. 2000 UM Ca$^{2+}$). However, removal of calcium and other divalent ions with 3 mM EDTA reduced the affinity of Ch5F2.4 to huC2 at neutral pH by ~27-fold at pH 7.3 ($K_D$ ~360 nM) and by 10-fold at acidic pH 6 ($K_D$ ~225 nM). The sensitivity of Ch5F2.4 to calcium suggest this ion is a key determinant for huC2/Ch5F2.4 complex formation and release (i.e. sweeping) of huC2 into the lumen of the recycling endosome.

Ch5F2.4 did not detectably bind huC2a.

TABLE 22

Steady-state binding affinity of huC2 to Ch5F2.4 antibody
measured in presence of increasing concentrations of Calcium
Chloride (Ca2+) at neutral pH (pH 7.3).

| Analyte | Ligand | $K_D$* (nM) | SEM (nM) | N |
|---|---|---|---|---|
| huC2 0 mM Ca$^{2+}$ | Ch5F2.4 | 357.5 | 6.6 | 3 |
| huC2 20 mM Ca$^{2+}$ | Ch5F2.4 | 150.7 | 2.8 | 3 |

TABLE 22-continued

Steady-state binding affinity of huC2 to Ch5F2.4 antibody
measured in presence of increasing concentrations of Calcium
Chloride (Ca2+) at neutral pH (pH 7.3).

| Analyte | Ligand | $K_D$* (nM) | SEM (nM) | N |
|---|---|---|---|---|
| huC2 200 mM Ca$^{2+}$ | Ch5F2.4 | 41.1 | 0.6 | 3 |
| huC2 2000 mM Ca$^{2+}$ | Ch5F2.4 | 13.9 | 0.2 | 3 |

*Steady state $K_D$

TABLE 23

Steady-state binding affinity of huC2 to Ch5F2.4 antibody
measured in presence of increasing concentrations of Calcium
Chloride (Ca2+) at acidic pH (pH 6.0).

| Analyte | Ligand | $K_D$* (nM) | SEM (nM) | N |
|---|---|---|---|---|
| huC2 0 mM Ca$^{2+}$ | Ch5F2.4 | 223.9 | 10.0 | 3 |
| huC2 20 mM Ca$^{2+}$ | Ch5F2.4 | 144.2 | 4.1 | 3 |
| huC2 200 mM Ca$^{2+}$ | Ch5F2.4 | 70.7 | 2.2 | 3 |
| huC2 2000 mM Ca$^{2+}$ | Ch5F2.4 | 21.7 | 0.6 | 3 |

*Steady state $K_D$

Calcium had negligible impact on the binding properties of huC2 to Ch13 at neutral and acidic pH (Tables 24 and 25). Furthermore, huC2 bound Ch13 with comparable affinities at neutral ($K_D$ ~4 nM) and acidic pH ($K_D$ ~4 nM).

Unlike RF16-226 and Ch5F2.4, Ch13 did detectably bind to human C2a (the larger enzymatically active fragment of C2). Ch13 bound to huC2a with an affinity of about 10 nM at neutral pH. huC2a binding to Ch13 was ~4-fold weaker at acidic pH ($K_D$ ~45 nM) (Tables 26 and 27).

TABLE 24

Binding kinetics of huC2 to Ch13 antibody measured
in presence of increasing concentrations of
Calcium Chloride (Ca2+) at neutral conditions (pH 7.3).

| Analyte | Ligand | $k_a$ (1/Ms) | $k_d$ (1/s) | $K_D$ (nM) | SEM (nM) | N |
|---|---|---|---|---|---|---|
| huC2 0 mM Ca$^{2+}$ | Ch13 | $3.39 \times 10^5$ | $1.44 \times 10^{-3}$ | 4.3 | 0.08 | 3 |
| huC2 20 mM Ca$^{2+}$ | Ch13 | $3.56 \times 10^5$ | $1.42 \times 10^{-3}$ | 4.0 | 0.03 | 3 |
| huC2 200 mM Ca$^{2+}$ | Ch13 | $3.59 \times 10^5$ | $1.40 \times 10^{-3}$ | 3.9 | 0.03 | 3 |
| huC2 2000 mM Ca$^{2+}$ | Ch13 | $3.50 \times 10^5$ | $1.39 \times 10^{-3}$ | 4.0 | 0.10 | 3 |

TABLE 25

Binding kinetics of huC2 to Ch13 antibody measured
in presence of increasing concentrations of
Calcium Chloride (Ca2+) at acidic pH (pH 6.0).

| Analyte | Ligand | $k_a$ (1/Ms) | $k_d$ (1/s) | $K_D$ (nM) | SEM (nM) | N |
|---|---|---|---|---|---|---|
| huC2 0 mM Ca$^{2+}$ | Ch13 | $5.90 \times 10^5$ | $1.67 \times 10^{-3}$ | 2.8 | 0.1 | 3 |
| huC2 20 mM Ca$^{2+}$ | Ch13 | $7.72 \times 10^5$ | $1.65 \times 10^{-3}$ | 2.1 | 0.1 | 3 |
| huC2 200 mM Ca$^{2+}$ | Ch13 | $7.22 \times 10^5$ | $1.66 \times 10^{-3}$ | 2.3 | 0.1 | 3 |
| huC2 2000 mM Ca$^{2+}$ | Ch13 | $5.01 \times 10^5$ | $1.76 \times 10^{-3}$ | 3.5 | 0.1 | 3 |

TABLE 26

Binding kinetics of huC2a to Ch13 antibody measured
in presence of increasing concentrations of
Calcium Chloride (Ca2+) at neutral conditions (pH 7.3).

| Analyte | Ligand | $k_a$ (1/Ms) | $k_d$ (1/s) | $K_D$ (nM) | SEM (nM) | N |
|---|---|---|---|---|---|---|
| huC2 0 mM Ca$^{2+}$ | Ch13 | $1.67 \times 10^5$ | $1.79 \times 10^{-3}$ | 10.7 | n/a | 1 |
| huC2 20 mM Ca$^{2+}$ | Ch13 | $1.64 \times 10^5$ | $1.75 \times 10^{-3}$ | 10.7 | n/a | 1 |
| huC2 200 mM Ca$^{2+}$ | Ch13 | $1.62 \times 10^5$ | $1.82 \times 10^{-3}$ | 11.2 | n/a | 1 |
| huC2 2000 mM Ca$^{2+}$ | Ch13 | $1.59 \times 10^5$ | $1.84 \times 10^{-3}$ | 11.6 | n/a | 1 |

TABLE 27

Binding kinetics of huC2a to Ch13 antibody measured
in presence of increasing concentrations of
Calcium Chloride (Ca2+) at acidic pH (pH 6.0).

| Analyte | Ligand | $k_a$ (1/Ms) | $k_d$ (1/s) | $K_D$ (nM) | SEM (nM) | N |
|---|---|---|---|---|---|---|
| huC2 0 mM Ca$^{2+}$ | Ch13 | $5.46 \times 10^4$ | $2.53 \times 10^{-3}$ | 46.4 | n/a | 1 |
| huC2 20 mM Ca$^{2+}$ | Ch13 | $5.50 \times 10^4$ | $2.56 \times 10^{-3}$ | 46.6 | n/a | 1 |
| huC2 200 mM Ca$^{2+}$ | Ch13 | $5.62 \times 10^4$ | $2.51 \times 10^{-3}$ | 44.7 | n/a | 1 |
| huC2 2000 mM Ca$^{2+}$ | Ch13 | $5.50 \times 10^4$ | $2.53 \times 10^{-3}$ | 46.0 | n/a | 1 |

Example 9—Binding to C2a and C2b

Antibodies RF16-226, RF16-226G, RF16-226G YPY, and Ch5F2.4 were tested for their ability to bind to C2 zymogen, C2a and C2b using similar surface plasmon resonance assays to those described above. Purified human C2 zymogen and human C2a were tested at concentrations ranging from 1.9 to 500 M while human C2b was tested at concentrations ranging from 1.9 to 1000 nM. All experiments were performed in HBS-EP buffer supplemented with 0.1% BSA at 37° C. and pH 7.3. Each antibody was tested against human C2 zymogen and human C2a in duplicate and against C2b in quadruplicate. The flow rate was set to 30 μL/min. Each analyte concentration was tested in duplicate. Experiments involving Ch5F2.4 were performed using 2 mM Ca$^{2+}$ in the running buffer, as this is required for optimal binding of Ch5F2.4.

As shown in Table 28, human C2 zymogen bound RF16-226 with a $K_D$ of 8 nM, RF16-226G at $K_D$ 7 nM, RF16-226G YPY at $K_D$ 8 nM, and Ch5F2.4 at $K_D$ 0.6 nM (affinities are an average of two experiments). No binding of human C2a was detected for RF16-226, RF16-226G, RF16-226G YPY, or Ch5F2.4. No binding of human C2b was detected for RF16-226, RF16-226G, or RF16-226G YPY. However, Ch5F2.4 did bind to human C2b with a $K_D$ 0.25 nM.

TABLE 28 binding affinities of pH-dependent anti-C2 antibodies to human C2
zymogen, C2a and C2b.

| Antibody | C2 affinity ($K_D$) | C2a affinity ($K_D$) | C2b affinity ($K_D$) |
|---|---|---|---|
| RF16-226 | 8 nM | NB | NB |
| RF16-226G | 7 nM | NB | NB |
| RF16-226G YPY | 8 nM | NB | NB |
| Ch5F2.4 | 0.6 nM | NB | 0.25 nM |

"NB" indicates that no binding was detected.

These data, in combination with the epitope mapping experiments described in Example 4, suggest that the epitope of RF16-226, and modified versions thereof, lies near or at the interface between the C2a and C2b domains of C2 zymogen, because both domains are required for detectable binding.

The invention claimed is:

1. A protein comprising an antigen binding site which binds to human complement C2 (C2) with greater affinity at pH 7.3 than at pH 6.0, wherein the protein comprises:

(i) a heavy chain variable region ($V_H$) comprising a complementarity determining region (CDR)1 comprising the amino acid sequence set forth in SEQ ID NO: 12, a CDR2 comprising the amino acid sequence set forth in SEQ ID NO: 15, and a CDR3 comprising the amino acid sequence set forth in SEQ ID NO: 18, and a light chain variable region ($V_L$) comprising a CDR1 comprising the amino acid sequence set forth in SEQ ID NO: 21, a CDR2 comprising the amino acid sequence set forth in SEQ ID NO: 24, and a CDR3 comprising the amino acid sequence set forth in SEQ ID NO: 27;

(ii) a $V_H$ comprising a CDR1 comprising the amino acid sequence set forth in SEQ ID NO: 13, a CDR2 comprising the amino acid sequence set forth in SEQ ID NO: 16, and a CDR3 comprising the amino acid sequence set forth in SEQ ID NO: 19, and a VL comprising a CDR1 comprising the amino acid sequence set forth in SEQ ID NO: 22, a CDR2 comprising the amino acid sequence set forth in SEQ ID NO: 25, and a CDR3 comprising the amino acid sequence set forth in SEQ ID NO: 28;

(iii) a VH comprising a CDR1 comprising the amino acid sequence set forth in SEQ ID NO: 14, a CDR2 comprising the amino acid sequence set forth in SEQ ID NO: 17, and a CDR3 comprising the amino acid sequence set forth in SEQ ID NO: 20, and a VL comprising a CDR1 comprising the amino acid sequence set forth in SEQ ID NO: 23, a CDR2 comprising the amino acid sequence set forth in SEQ ID NO: 26, and a CDR3 comprising the amino acid sequence set forth in SEQ ID NO: 29;

(iv) a VH comprising a CDR1 comprising the amino acid sequence set forth in SEQ ID NO: 54, a CDR2 comprising the amino acid sequence set forth in SEQ ID NO: 55, and a CDR3 comprising the amino acid sequence set forth in SEQ ID NO: 56 and, a VL comprising a CDR1 comprising the amino acid sequence set forth in SEQ ID NO: 57, a CDR2 comprising the amino acid sequence set forth in SEQ ID NO: 58, and a CDR3 comprising the amino acid sequence set forth in SEQ ID NO: 59; or (v) a VH comprising a CDR1 comprising the amino acid sequence set forth in SEQ ID NO: 60, a CDR2 comprising the amino acid sequence set forth in SEQ ID NO: 61, and a CDR3 comprising the amino acid sequence set forth in SEQ ID NO: 62, and a $V_L$ comprising a CDR1 comprising the amino acid sequence set forth in SEQ ID NO: 63, a CDR2 comprising the amino acid sequence set forth in SEQ ID NO: 64, and a CDR3 comprising the amino acid sequence set forth in SEQ ID NO: 65.

2. The protein of claim 1, wherein the protein:

(a) binds to C2 at pH 7.3 with an affinity which is at least 2-fold greater or at least 10-fold greater than at pH 6.0;

(b) binds to C2 at pH 7.3 with an affinity of at least about 30 nM, wherein affinity is determined in an assay in which the protein is immobilized and C2 is contacted with the immobilized protein;

(c) binds to C2 at pH 6.0 with an affinity of at most about 50 nM, wherein affinity is determined in an assay in which the protein is immobilized and C2 is contacted with the immobilized protein;

(d) binds to both human and cynomolgus monkey C2 with a similar affinity;

(e) does not detectably bind to dog C2, rat C2, rabbit C2, pig C2, and/or sheep C2;

(f) does not detectably bind to a polypeptide comprising the alanine substitution at position 443 of SEQ ID NO: 1;

(g) binds to an epitope comprising residues within one or two or three regions selected from 266-284, 318-333, and 428-459 of SEQ ID NO: 1; and/or (h) inhibits the classical complement pathway and/or the lectin complement pathway with an IC50 of at least 50 nM or at least 10 nM, wherein the IC50 is determined by an immunoassay that measures complement activation.

3. The protein of claim 1, wherein the affinity of the protein to a polypeptide of SEQ ID NO: 1 in which an alanine is substituted for one of:

(i) the lysine at position 443 of SEQ ID NO:1;

(ii) the histidine at position 331 of SEQ ID NO:1; or (iii) the lysine at position 457 of SEQ ID NO:1, is lower than the affinity of the protein to a polypeptide of SEQ ID NO: 1.

4. The protein of claim 3, wherein the affinity of the protein to the polypeptide comprising any one of the alanine substitutions is at least 10-fold lower than the affinity of the protein to the polypeptide of SEQ ID NO:1.

5. The protein of claim 1, which comprises (i) a $V_H$ comprising the amino acid sequence set forth in SEQ ID NO: 2 and a $V_L$ comprising the amino acid sequence set forth in SEQ ID NO: 6 or 9;

(ii) a $V_H$ comprising the amino acid sequence set forth in SEQ ID NO: 3 and a $V_L$ comprising the amino acid sequence set forth in SEQ ID NO: 7 or 10;

(iii) a $V_H$ comprising the amino acid sequence set forth in SEQ ID NO: 4 and a $V_L$ comprising the amino acid sequence set forth in SEQ ID NO: 8;

(iv) a $V_H$ comprising the amino acid sequence set forth in SEQ ID NO: 5 and a $V_L$ comprising the amino acid sequence set forth in SEQ ID NO: 11;

(v) a $V_H$ comprising the amino acid sequence set forth in SEQ ID NO: 46 and a $V_L$ comprising the amino acid sequence set forth in SEQ ID NO: 50; or (vi) a $V_H$ comprising the amino acid sequence set forth in SEQ ID NO: 47 and a $V_L$ comprising the amino acid sequence set forth in SEQ ID NO: 51.

6. The protein of claim 1 comprising at least a $V_H$ and a $V_L$, wherein the $V_H$ and $V_L$ bind to form a Fv comprising the antigen binding site.

7. The protein of claim 6, wherein the $V_H$ and the $V_L$ are in a single polypeptide chain.

8. The protein of claim 7, which is:

(i) a single chain Fv fragment (scFv);

(ii) a dimeric scFv (di-scFv); or (iii) at least one of (i) and/or (ii) linked to a constant region of an antibody, a fragment crystallizable (Fc) region or a heavy chain constant domain $(C_H)2$ and/or $C_H3$.

9. The protein of claim 6, wherein the $V_L$ and $V_H$ are in separate polypeptide chains.

10. The protein of claim 1, wherein the protein is an antibody that comprises an Fc region.

11. The protein of claim 10, which comprises one or more amino acid substitutions in the Fc region which increases the protein's affinity to neonatal Fc receptor (FcRn).

12. The protein of claim 11, wherein the one or more amino acid substitutions are selected from M252Y, S254T, T256E, V308P, N286E, M428L, N434A, and N434Y.

13. The protein of claim 12, which comprises the following amino acid substitutions in its Fc region:

(i) M252Y, (ii) N286E or V308P, and (iii) N434Y.

14. The protein of claim 10, which is an antibody comprising a heavy chain comprising the amino acid sequence set forth in any one of SEQ ID NOs: 30-33 and a light chain comprising the amino acid sequence set forth in any one of SEQ ID NOs: 34-39.

15. A composition comprising the protein of claim 1 and a pharmaceutically acceptable carrier.

16. The protein of claim 10, which is an antibody comprising a heavy chain comprising the amino acid sequence set forth in SEQ ID NO: 30 and a light chain comprising the amino acid sequence set forth in SEQ ID NO: 34 or 37.

17. The protein of claim 1, wherein the protein comprises a $V_H$ comprising CDR1 comprising the amino acid sequence set forth in SEQ ID NO: 12, a CDR2 comprising the amino acid sequence set forth in SEQ ID NO: 15, and a CDR3 comprising the amino acid sequence set forth in SEQ ID NO: 18, and a $V_L$ comprising a CDR1 comprising the amino acid sequence set forth in SEQ ID NO: 21, a CDR2 comprising the amino acid sequence set forth in SEQ ID NO: 24, and a CDR3 comprising the amino acid sequence set forth in SEQ ID NO: 27.

18. The protein of claim 17, wherein the protein comprises a $V_H$ comprising the amino acid sequence set forth in SEQ ID NO: 2 and a $V_L$ comprising the amino acid sequence set forth in SEQ ID NO: 6 or 9.

* * * * *

SEQUENCE LISTING

<160> NUMBER OF SEQ ID NOS: 71

<210> SEQ ID NO 1
<211> LENGTH: 752
<212> TYPE: PRT
<213> ORGANISM: Homo sapiens

<400> SEQUENCE: 1

Met Gly Pro Leu Met Val Leu Phe Cys Leu Leu Phe Leu Tyr Pro Gly
1               5                   10                  15

Leu Ala Asp Ser Ala Pro Ser Cys Pro Gln Asn Val Asn Ile Ser Gly

```
                20              25              30
Gly Thr Phe Thr Leu Ser His Gly Trp Ala Pro Gly Ser Leu Leu Thr
                35              40              45
Tyr Ser Cys Pro Gln Gly Leu Tyr Pro Ser Pro Ala Ser Arg Leu Cys
        50              55              60
Lys Ser Ser Gly Gln Trp Gln Thr Pro Gly Ala Thr Arg Ser Leu Ser
65              70              75              80
Lys Ala Val Cys Lys Pro Val Arg Cys Pro Ala Pro Val Ser Phe Glu
                85              90              95
Asn Gly Ile Tyr Thr Pro Arg Leu Gly Ser Tyr Pro Val Gly Gly Asn
                100             105             110
Val Ser Phe Glu Cys Glu Asp Gly Phe Ile Leu Arg Gly Ser Pro Val
            115             120             125
Arg Gln Cys Arg Pro Asn Gly Met Trp Asp Gly Glu Thr Ala Val Cys
            130             135             140
Asp Asn Gly Ala Gly His Cys Pro Asn Pro Gly Ile Ser Leu Gly Ala
145             150             155             160
Val Arg Thr Gly Phe Arg Phe Gly His Gly Asp Lys Val Arg Tyr Arg
            165             170             175
Cys Ser Ser Asn Leu Val Leu Thr Gly Ser Ser Glu Arg Glu Cys Gln
            180             185             190
Gly Asn Gly Val Trp Ser Gly Thr Glu Pro Ile Cys Arg Gln Pro Tyr
            195             200             205
Ser Tyr Asp Phe Pro Glu Asp Val Ala Pro Ala Leu Gly Thr Ser Phe
    210             215             220
Ser His Met Leu Gly Ala Thr Asn Pro Thr Gln Lys Thr Lys Glu Ser
225             230             235             240
Leu Gly Arg Lys Ile Gln Ile Gln Arg Ser Gly His Leu Asn Leu Tyr
            245             250             255
Leu Leu Leu Asp Cys Ser Gln Ser Val Ser Glu Asn Asp Phe Leu Ile
            260             265             270
Phe Lys Glu Ser Ala Ser Leu Met Val Asp Arg Ile Phe Ser Phe Glu
            275             280             285
Ile Asn Val Ser Val Ala Ile Ile Thr Phe Ala Ser Glu Pro Lys Val
    290             295             300
Leu Met Ser Val Leu Asn Asp Asn Ser Arg Asp Met Thr Glu Val Ile
305             310             315             320
Ser Ser Leu Glu Asn Ala Asn Tyr Lys Asp His Glu Asn Gly Thr Gly
            325             330             335
Thr Asn Thr Tyr Ala Ala Leu Asn Ser Val Tyr Leu Met Met Asn Asn
            340             345             350
Gln Met Arg Leu Leu Gly Met Glu Thr Met Ala Trp Gln Glu Ile Arg
            355             360             365
His Ala Ile Ile Leu Leu Thr Asp Gly Lys Ser Asn Met Gly Gly Ser
    370             375             380
Pro Lys Thr Ala Val Asp His Ile Arg Glu Ile Leu Asn Ile Asn Gln
385             390             395             400
Lys Arg Asn Asp Tyr Leu Asp Ile Tyr Ala Ile Gly Val Gly Lys Leu
            405             410             415
Asp Val Asp Trp Arg Glu Leu Asn Glu Leu Gly Ser Lys Lys Asp Gly
            420             425             430
Glu Arg His Ala Phe Ile Leu Gln Asp Thr Lys Ala Leu His Gln Val
            435             440             445
```

-continued

```
Phe Glu His Met Leu Asp Val Ser Lys Leu Thr Asp Thr Ile Cys Gly
    450                 455                 460

Val Gly Asn Met Ser Ala Asn Ala Ser Asp Gln Glu Arg Thr Pro Trp
465                 470                 475                 480

His Val Thr Ile Lys Pro Lys Ser Gln Glu Thr Cys Arg Gly Ala Leu
                485                 490                 495

Ile Ser Asp Gln Trp Val Leu Thr Ala Ala His Cys Phe Arg Asp Gly
                500                 505                 510

Asn Asp His Ser Leu Trp Arg Val Asn Val Gly Asp Pro Lys Ser Gln
            515                 520                 525

Trp Gly Lys Glu Phe Leu Ile Glu Lys Ala Val Ile Ser Pro Gly Phe
    530                 535                 540

Asp Val Phe Ala Lys Lys Asn Gln Gly Ile Leu Glu Phe Tyr Gly Asp
545                 550                 555                 560

Asp Ile Ala Leu Leu Lys Leu Ala Gln Lys Val Lys Met Ser Thr His
            565                 570                 575

Ala Arg Pro Ile Cys Leu Pro Cys Thr Met Glu Ala Asn Leu Ala Leu
            580                 585                 590

Arg Arg Pro Gln Gly Ser Thr Cys Arg Asp His Glu Asn Glu Leu Leu
            595                 600                 605

Asn Lys Gln Ser Val Pro Ala His Phe Val Ala Leu Asn Gly Ser Lys
    610                 615                 620

Leu Asn Ile Asn Leu Lys Met Gly Val Glu Trp Thr Ser Cys Ala Glu
625                 630                 635                 640

Val Val Ser Gln Glu Lys Thr Met Phe Pro Asn Leu Thr Asp Val Arg
                645                 650                 655

Glu Val Val Thr Asp Gln Phe Leu Cys Ser Gly Thr Gln Glu Asp Glu
            660                 665                 670

Ser Pro Cys Lys Gly Glu Ser Gly Gly Ala Val Phe Leu Glu Arg Arg
            675                 680                 685

Phe Arg Phe Phe Gln Val Gly Leu Val Ser Trp Gly Leu Tyr Asn Pro
    690                 695                 700

Cys Leu Gly Ser Ala Asp Lys Asn Ser Arg Lys Arg Ala Pro Arg Ser
705                 710                 715                 720

Lys Val Pro Pro Pro Arg Asp Phe His Ile Asn Leu Phe Arg Met Gln
            725                 730                 735

Pro Trp Leu Arg Gln His Leu Gly Asp Val Leu Asn Phe Leu Pro Leu
            740                 745                 750
```

```
<210> SEQ ID NO 2
<211> LENGTH: 119
<212> TYPE: PRT
<213> ORGANISM: Artificial Sequence
<220> FEATURE:
<223> OTHER INFORMATION: Synthetic antibody sequence.

<400> SEQUENCE: 2

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60
```

Gln Gly Gln Val Thr Ile Ser Ala Asp Lys Ser Ile Ser Thr Ala Tyr
65                      70                      75                      80

Leu Gln Trp Ser Ser Leu Lys Ala Ser Asp Thr Ala Met Tyr Tyr Cys
                        85                      90                      95

Ala Arg Arg Phe Ser Tyr Ser Ser Gly Trp Asp Met Trp Gly Gln Gly
            100                     105                     110

Thr Leu Val Thr Val Ser Ser
        115

<210> SEQ ID NO 3
<211> LENGTH: 116
<212> TYPE: PRT
<213> ORGANISM: Artificial Sequence
<220> FEATURE:
<223> OTHER INFORMATION: Synthetic antibody sequence.

<400> SEQUENCE: 3

Glu Val Gln Leu Leu Glu Ser Gly Gly Gly Leu Val Gln Pro Gly Gly
1                       5                       10                      15

Ser Leu Arg Leu Ser Cys Ala Ala Ser Gly Phe Thr Phe Ser Trp Tyr
            20                      25                      30

Gln Met Met Trp Val Arg Gln Ala Pro Gly Lys Gly Leu Glu Trp Val
            35                      40                      45

Ser Arg Ile Tyr Pro Ser Gly Gly Thr Ala Tyr Ala Asp Ser Val
            50                      55                      60

Lys Gly Arg Phe Thr Ile Ser Arg Asp Asn Ser Lys Asn Thr Leu Tyr
65                      70                      75                      80

Leu Gln Met Asn Ser Leu Arg Ala Glu Asp Thr Ala Val Tyr Tyr Cys
                        85                      90                      95

Ala Arg Asp Ala Gly Tyr Gly Asp Asn Trp Gly Gln Gly Thr Leu Val
            100                     105                     110

Thr Val Ser Ser
        115

<210> SEQ ID NO 4
<211> LENGTH: 119
<212> TYPE: PRT
<213> ORGANISM: Artificial Sequence
<220> FEATURE:
<223> OTHER INFORMATION: Synthetic antibody sequence.

<400> SEQUENCE: 4

Glu Val Gln Leu Val Gln Ser Gly Ala Glu Val Lys Lys Pro Gly Glu
1                       5                       10                      15

Ser Leu Lys Ile Ser Cys Lys Gly Ser Gly Tyr Ser Phe Thr Ser Tyr
            20                      25                      30

Trp Ile Gly Trp Val Arg Gln Met Pro Gly Lys Gly Leu Glu Trp Met
            35                      40                      45

Gly Ile Ile Tyr Pro Gly Asp Ser Asp Thr Arg Tyr Ser Pro Ser Phe
            50                      55                      60

Gln Gly Gln Val Thr Ile Ser Ala Asp Lys Ser Ile Ser Thr Ala Tyr
65                      70                      75                      80

Leu Gln Trp Ser Ser Leu Lys Ala Ser Asp Thr Ala Met Tyr Tyr Cys
                        85                      90                      95

Ala Arg Arg Gly His Tyr Gly Asp Tyr Phe Asp Tyr Trp Gly Gln Gly
            100                     105                     110

Thr Leu Val Thr Val Ser Ser

115

<210> SEQ ID NO 5
<211> LENGTH: 119
<212> TYPE: PRT
<213> ORGANISM: Artificial Sequence
<220> FEATURE:
<223> OTHER INFORMATION: Synthetic antibody sequence.

<400> SEQUENCE: 5

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Gly His Tyr Gly Asp Tyr Phe Asp Tyr Trp Gly Gln Gly
            100                 105                 110

Thr Leu Val Thr Val Ser Ser
        115

<210> SEQ ID NO 6
<211> LENGTH: 111
<212> TYPE: PRT
<213> ORGANISM: Artificial Sequence
<220> FEATURE:
<223> OTHER INFORMATION: Synthetic antibody sequence.

<400> SEQUENCE: 6

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Thr Ser Lys Tyr Val
            20                  25                  30

Ala Trp Tyr Gln Gln Lys Ser Gly Gln Ala Pro Val Leu Val Ile Tyr
        35                  40                  45

Glu Asp Thr Arg Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ala Ser Gly His Gln
                85                  90                  95

Arg Val Phe Gly Gly Gly Thr Lys Leu Thr Val Leu Gly Gln Pro
            100                 105                 110

<210> SEQ ID NO 7
<211> LENGTH: 109
<212> TYPE: PRT
<213> ORGANISM: Artificial Sequence
<220> FEATURE:
<223> OTHER INFORMATION: Synthetic antibody sequence.

<400> SEQUENCE: 7

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Glu Lys Tyr Ala
            20                  25                  30

Ser Trp Tyr Gln Gln Lys Pro Gly Gln Ser Pro Val Leu Val Ile Tyr
            35                  40                  45

Gln Asp Arg Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Thr Arg Ala Val Val
                85                  90                  95

Phe Gly Gly Gly Thr Lys Leu Thr Val Leu Gly Gln Pro
            100                 105

<210> SEQ ID NO 8
<211> LENGTH: 111
<212> TYPE: PRT
<213> ORGANISM: Artificial Sequence
<220> FEATURE:
<223> OTHER INFORMATION: Synthetic antibody sequence.

<400> SEQUENCE: 8

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
            35                  40                  45

Glu Asp Arg Arg Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Arg Asp Arg Ala Gly Asn Gln
                85                  90                  95

Arg Val Phe Gly Gly Gly Thr Gln Leu Thr Val Leu Gly Gln Pro
            100                 105                 110

<210> SEQ ID NO 9
<211> LENGTH: 111
<212> TYPE: PRT
<213> ORGANISM: Artificial Sequence
<220> FEATURE:
<223> OTHER INFORMATION: Synthetic antibody sequence.

<400> SEQUENCE: 9

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Thr Ser Lys Tyr Val
            20                  25                  30

Ala Trp Tyr Gln Gln Lys Ser Gly Leu Ala Pro Leu Leu Val Ile Tyr
            35                  40                  45

Glu Asp Thr Arg Arg Pro Ser Gly Ile Pro Ala Lys Phe Ser Gly Ser
    50                  55                  60

Ser Ser Gly Ser Val Ala Thr Leu Thr Ile Ser Gly Ala His Gly Asp
65                  70                  75                  80

Asp Glu Ala Asp Tyr Tyr Cys Tyr Ser Thr Asp Ala Ser Gly His Gln
                85                  90                  95

Arg Val Phe Gly Gly Gly Thr Lys Leu Thr Val Leu Ser Gln Pro

-continued

```
            100             105             110

<210> SEQ ID NO 10
<211> LENGTH: 109
<212> TYPE: PRT
<213> ORGANISM: Artificial Sequence
<220> FEATURE:
<223> OTHER INFORMATION: Synthetic antibody sequence.

<400> SEQUENCE: 10

Gln Ser Ala Leu Thr Gln Pro Pro Ser Val Ser Val Ser Pro Gly Gln
1               5                   10                  15

Thr Ala Ser Ile Thr Cys Ser Gly Asp Lys Leu Gly Glu Lys Tyr Ala
            20                  25                  30

Ser Trp Tyr Gln Gln Lys Ala Gly Gln Ser Pro Val Met Val Ile Tyr
        35                  40                  45

Gln Asp Arg Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Thr Arg Ala Val Val
                85                  90                  95

Phe Gly Gly Gly Thr Lys Leu Thr Val Leu Gly Gln Pro
            100                 105

<210> SEQ ID NO 11
<211> LENGTH: 111
<212> TYPE: PRT
<213> ORGANISM: Artificial Sequence
<220> FEATURE:
<223> OTHER INFORMATION: Synthetic antibody sequence.

<400> SEQUENCE: 11

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr His Gln Lys Ser Gly Gln Ala Pro Val Leu Val Ile Tyr
        35                  40                  45

Glu Asp Arg Arg Arg Pro Ser Glu Ile Pro Glu Arg Phe Ser Gly Ser
    50                  55                  60

Ser Ser Gly Thr Met Ala Thr Leu Thr Ile Thr Gly Ala Gln Val Glu
65                  70                  75                  80

Asp Glu Gly Val Tyr Phe Cys Tyr Ser Arg Asp Arg Ala Gly Asn Gln
                85                  90                  95

Arg Val Phe Gly Gly Gly Thr Gln Leu Thr Val Leu Gly Gln Pro
            100                 105                 110

<210> SEQ ID NO 12
<211> LENGTH: 5
<212> TYPE: PRT
<213> ORGANISM: Artificial Sequence
<220> FEATURE:
<223> OTHER INFORMATION: Synthetic antibody sequence.

<400> SEQUENCE: 12

Ser Tyr Trp Ile Gly
1               5

<210> SEQ ID NO 13
```

```
<211> LENGTH: 5
<212> TYPE: PRT
<213> ORGANISM: Artificial Sequence
<220> FEATURE:
<223> OTHER INFORMATION: Synthetic antibody sequence.

<400> SEQUENCE: 13

Trp Tyr Gln Met Met
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic antibody sequence.

<400> SEQUENCE: 14

Ser Tyr Trp Ile Gly
1               5

<210> SEQ ID NO 15
<211> LENGTH: 17
<212> TYPE: PRT
<213> ORGANISM: Artificial Sequence
<220> FEATURE:
<223> OTHER INFORMATION: Synthetic antibody sequence.

<400> SEQUENCE: 15

Ile Ile Tyr Pro Gly Asp Ser Asp Thr Arg Tyr Ser Pro Ser Phe Gln
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Synthetic antibody sequence.

<400> SEQUENCE: 16

Arg Ile Tyr Pro Ser Gly Gly Gly Thr Ala Tyr Ala Asp Ser Val Lys
1               5                   10                  15

Gly

<210> SEQ ID NO 17
<211> LENGTH: 17
<212> TYPE: PRT
<213> ORGANISM: Artificial Sequence
<220> FEATURE:
<223> OTHER INFORMATION: Synthetic antibody sequence.

<400> SEQUENCE: 17

Ile Ile Tyr Pro Gly Asp Ser Asp Thr Arg Tyr Ser Pro Ser Phe Gln
1               5                   10                  15

Gly

<210> SEQ ID NO 18
<211> LENGTH: 10
<212> TYPE: PRT
<213> ORGANISM: Artificial Sequence
<220> FEATURE:
<223> OTHER INFORMATION: Synthetic antibody sequence.

<400> SEQUENCE: 18
```

```
Arg Phe Ser Tyr Ser Ser Gly Trp Asp Met
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic antibody sequence.

<400> SEQUENCE: 19

Asp Ala Gly Tyr Gly Asp Asn
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic antibody sequence.

<400> SEQUENCE: 20

Arg Gly His Tyr Gly Asp Tyr Phe Asp Tyr
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic antibody sequence.

<400> SEQUENCE: 21

Ser Gly Asp Ala Leu Thr Ser Lys Tyr Val Ala
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic antibody sequence.

<400> SEQUENCE: 22

Ser Gly Asp Lys Leu Gly Glu Lys Tyr Ala Ser
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic antibody sequence.

<400> SEQUENCE: 23

Ser Gly Asp Ala Leu Pro Lys Lys Tyr Ala Tyr
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Synthetic antibody sequence.

<400> SEQUENCE: 24

Glu Asp Thr Arg Arg Pro Ser
```

-continued

```
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic antibody sequence.

<400> SEQUENCE: 25

Gln Asp Arg Lys Arg Pro Ser
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic antibody sequence.

<400> SEQUENCE: 26

Glu Asp Arg Arg Arg Pro Ser
1               5

<210> SEQ ID NO 27
<211> LENGTH: 11
<212> TYPE: PRT
<213> ORGANISM: Artificial Sequence
<220> FEATURE:
<223> OTHER INFORMATION: Synthetic antibody sequence.

<400> SEQUENCE: 27

Tyr Ser Thr Asp Ala Ser Gly His Gln Arg Val
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Synthetic antibody sequence.

<400> SEQUENCE: 28

Gln Ala Trp Asp Thr Arg Ala Val Val
1               5

<210> SEQ ID NO 29
<211> LENGTH: 11
<212> TYPE: PRT
<213> ORGANISM: Artificial Sequence
<220> FEATURE:
<223> OTHER INFORMATION: Synthetic antibody sequence.

<400> SEQUENCE: 29

Tyr Ser Arg Asp Arg Ala Gly Asn Gln Arg Val
1               5                   10

<210> SEQ ID NO 30
<211> LENGTH: 446
<212> TYPE: PRT
<213> ORGANISM: Artificial Sequence
<220> FEATURE:
<223> OTHER INFORMATION: Synthetic antibody sequence.

<400> SEQUENCE: 30

Glu Val Gln Leu Val Gln Ser Gly Ala Glu Val Lys Lys Pro Gly Glu
1               5                   10                  15
```

```
Ser Leu Lys Ile Ser Cys Lys Gly Ser Gly Tyr Ser Phe Thr Ser Tyr
            20              25              30

Trp Ile Gly Trp Val Arg Gln Met Pro Gly Lys Gly Leu Glu Trp Met
            35              40              45

Gly Ile Ile Tyr Pro Gly Asp Ser Asp Thr Arg Tyr Ser Pro Ser Phe
    50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Tyr Cys
            85              90              95

Ala Arg Arg Phe Ser Tyr Ser Ser Gly Trp Asp Met Trp Gly Gln Gly
            100             105             110

Thr Leu Val Thr Val Ser Ser Ala Ser Thr Lys Gly Pro Ser Val Phe
            115             120             125

Pro Leu Ala Pro Cys Ser Arg Ser Thr Ser Glu Ser Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
            180             185             190

Ser Ser Leu Gly Thr Lys Thr Tyr Thr Cys Asn Val Asp His Lys Pro
            195             200             205

Ser Asn Thr Lys Val Asp Lys Arg Val Glu Ser Lys Tyr Gly Pro Pro
    210             215             220

Cys Pro Pro Cys Pro Ala Pro Glu Phe Leu Gly Gly Pro Ser Val Phe
225             230             235             240

Leu Phe Pro Pro Lys Pro Lys Asp Thr Leu Met Ile Ser Arg Thr Pro
            245             250             255

Glu Val Thr Cys Val Val Val Asp Val Ser Gln Glu Asp Pro Glu Val
            260             265             270

Gln Phe Asn Trp Tyr Val Asp Gly Val Glu Val His Asn Ala Lys Thr
            275             280             285

Lys Pro Arg Glu Glu Gln Phe Asn Ser Thr Tyr Arg Val Val Ser Val
    290             295             300

Leu Thr Val Leu His Gln Asp Trp Leu Asn Gly Lys Glu Tyr Lys Cys
305             310             315             320

Lys Val Ser Asn Lys Gly Leu Pro Ser Ser Ile Glu Lys Thr Ile Ser
            325             330             335

Lys Ala Lys Gly Gln Pro Arg Glu Pro Gln Val Tyr Thr Leu Pro Pro
            340             345             350

Ser Gln Glu Glu Met Thr Lys Asn Gln Val Ser Leu Thr Cys Leu Val
            355             360             365

Lys Gly Phe Tyr Pro Ser Asp Ile Ala Val Glu Trp Glu Ser Asn Gly
    370             375             380

Gln Pro Glu Asn Asn Tyr Lys Thr Thr Pro Pro Val Leu Asp Ser Asp
385             390             395             400

Gly Ser Phe Phe Leu Tyr Ser Arg Leu Thr Val Asp Lys Ser Arg Trp
            405             410             415

Gln Glu Gly Asn Val Phe Ser Cys Ser Val Met His Glu Ala Leu His
            420             425             430
```

```
Asn His Tyr Thr Gln Lys Ser Leu Ser Leu Ser Leu Gly Lys
        435                 440                 445

<210> SEQ ID NO 31
<211> LENGTH: 443
<212> TYPE: PRT
<213> ORGANISM: Artificial Sequence
<220> FEATURE:
<223> OTHER INFORMATION: Synthetic antibody sequence.

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Gln Met Met Trp Val Arg Gln Ala Pro Gly Lys Gly Leu Glu Trp Val
        35                  40                  45

Ser Arg Ile Tyr Pro Ser Gly Gly Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gly Tyr Gly Asp Asn Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Pro
        210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
            340                 345                 350
```

-continued

```
Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly Lys
        435                 440
```

```
<210> SEQ ID NO 32
<211> LENGTH: 446
<212> TYPE: PRT
<213> ORGANISM: Artificial Sequence
<220> FEATURE:
<223> OTHER INFORMATION: Synthetic antibody sequence.

<400> SEQUENCE: 32
```

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Gly His Tyr Gly Asp Tyr Phe Asp Tyr Trp Gly Gln Gly
                100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
        180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
        260                 265                 270
```

-continued

```
Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
        435                 440                 445
```

<210> SEQ ID NO 33
<211> LENGTH: 446
<212> TYPE: PRT
<213> ORGANISM: Artificial Sequence
<220> FEATURE:
<223> OTHER INFORMATION: Synthetic antibody sequence.

<400> SEQUENCE: 33

```
Glu Val Gln Leu Leu Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Gly His Tyr Gly Asp Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

-continued

```
Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445
```

<210> SEQ ID NO 34
<211> LENGTH: 214
<212> TYPE: PRT
<213> ORGANISM: Artificial Sequence
<220> FEATURE:
<223> OTHER INFORMATION: Synthetic antibody sequence.

<400> SEQUENCE: 34

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Thr Ser Lys Tyr Val
            20                  25                  30

Ala Trp Tyr Gln Gln Lys Ser Gly Gln Ala Pro Val Leu Val Ile Tyr
        35                  40                  45

Glu Asp Thr Arg Arg Pro Ser Gly Ile Pro Glu Arg Phe Ser Gly Ser
        50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ala Ser Gly His Gln
                85                  90                  95

Arg Val Phe Gly Gly Gly Thr Lys Leu Thr Val Leu Gly Gln Pro Lys
            100                 105                 110
```

-continued

```
Ala Ala Pro Ser Val Thr Leu Phe Pro Pro Ser Ser Glu Glu Leu Gln
        115                 120             125

Ala Asn Lys Ala Thr Leu Val Cys Leu Ile Ser Asp Phe Tyr Pro Gly
        130                 135             140

Ala Val Thr Val Ala Trp Lys Ala Asp Ser Ser Pro Val Lys Ala Gly
145                 150             155                 160

Val Glu Thr Thr Thr Pro Ser Lys Gln Ser Asn Asn Lys Tyr Ala Ala
                165             170             175

Ser Ser Tyr Leu Ser Leu Thr Pro Glu Gln Trp Lys Ser His Arg Ser
            180             185             190

Tyr Ser Cys Gln Val Thr His Glu Gly Ser Thr Val Glu Lys Thr Val
            195             200             205

Ala Pro Thr Glu Cys Ser
    210
```

```
<210> SEQ ID NO 35
<211> LENGTH: 212
<212> TYPE: PRT
<213> ORGANISM: Artificial Sequence
<220> FEATURE:
<223> OTHER INFORMATION: Synthetic antibody sequence.

<400> SEQUENCE: 35
```

```
Ser Tyr Glu Leu Thr Gln Pro Pro Ser Val Ser Val Ser Pro Gly Gln
1               5               10              15

Thr Ala Ser Ile Thr Cys Ser Gly Asp Lys Leu Gly Glu Lys Tyr Ala
                20              25              30

Ser Trp Tyr Gln Gln Lys Pro Gly Gln Ser Pro Val Leu Val Ile Tyr
            35              40              45

Gln Asp Arg Lys Arg Pro Ser Gly Ile Pro Glu Arg Phe Ser Gly Ser
        50              55              60

Asn Ser Gly Asn Thr Ala Thr Leu Thr Ile Ser Gly Thr Gln Ala Met
65                  70              75                  80

Asp Glu Ala Asp Tyr Tyr Cys Gln Ala Trp Asp Thr Arg Ala Val Val
                85              90              95

Phe Gly Gly Gly Thr Lys Leu Thr Val Leu Gly Gln Pro Lys Ala Ala
                100             105             110

Pro Ser Val Thr Leu Phe Pro Pro Ser Ser Glu Glu Leu Gln Ala Asn
        115             120             125

Lys Ala Thr Leu Val Cys Leu Ile Ser Asp Phe Tyr Pro Gly Ala Val
        130             135             140

Thr Val Ala Trp Lys Ala Asp Ser Ser Pro Val Lys Ala Gly Val Glu
145             150             155                 160

Thr Thr Thr Pro Ser Lys Gln Ser Asn Asn Lys Tyr Ala Ala Ser Ser
            165             170             175

Tyr Leu Ser Leu Thr Pro Glu Gln Trp Lys Ser His Arg Ser Tyr Ser
            180             185             190

Cys Gln Val Thr His Glu Gly Ser Thr Val Glu Lys Thr Val Ala Pro
        195             200             205

Thr Glu Cys Ser
    210
```

```
<210> SEQ ID NO 36
<211> LENGTH: 214
<212> TYPE: PRT
<213> ORGANISM: Artificial Sequence
<220> FEATURE:
```

<223> OTHER INFORMATION: Synthetic antibody sequence.

<400> SEQUENCE: 36

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
            35                  40                  45

Glu Asp Arg Arg Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65              70                  75                  80

Asp Glu Ala Asp Tyr Tyr Cys Tyr Ser Arg Asp Arg Ala Gly Asn Gln
                85                  90                  95

Arg Val Phe Gly Gly Gly Thr Gln Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
                195                 200                 205

Ala Pro Thr Glu Cys Ser
    210
```

<210> SEQ ID NO 37
<211> LENGTH: 214
<212> TYPE: PRT
<213> ORGANISM: Artificial Sequence
<220> FEATURE:
<223> OTHER INFORMATION: Synthetic antibody sequence.

<400> SEQUENCE: 37

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Thr Ser Lys Tyr Val
            20                  25                  30

Ala Trp Tyr Gln Gln Lys Ser Gly Leu Ala Pro Leu Leu Val Ile Tyr
            35                  40                  45

Glu Asp Thr Arg Arg Pro Ser Gly Ile Pro Ala Lys Phe Ser Gly Ser
    50                  55                  60

Ser Ser Gly Ser Val Ala Thr Leu Thr Ile Ser Gly Ala His Gly Asp
65              70                  75                  80

Asp Glu Ala Asp Tyr Tyr Cys Tyr Ser Thr Asp Ala Ser Gly His Gln
                85                  90                  95

Arg Val Phe Gly Gly Gly Thr Lys Leu Thr Val Leu Ser Gln Pro Lys
                100                 105                 110

Ala Ala Pro Ser Val Thr Leu Phe Pro Pro Ser Ser Glu Glu Leu Gln
            115                 120                 125
```

Ala Asn Lys Ala Thr Leu Val Cys Leu Ile Ser Asp Phe Tyr Pro Gly
    130             135             140

Ala Val Thr Val Ala Trp Lys Ala Asp Gly Ser Pro Val Lys Ala Gly
145             150             155             160

Val Glu Thr Thr Lys Pro Ser Lys Gln Ser Asn Asn Lys Tyr Ala Ala
            165             170             175

Ser Ser Tyr Leu Ser Leu Thr Pro Glu Gln Trp Lys Ser His Arg Ser
            180             185             190

Tyr Ser Cys Gln Val Thr His Glu Gly Ser Thr Val Glu Lys Thr Val
        195             200             205

Ala Pro Thr Glu Cys Ser
    210

<210> SEQ ID NO 38
<211> LENGTH: 212
<212> TYPE: PRT
<213> ORGANISM: Artificial Sequence
<220> FEATURE:
<223> OTHER INFORMATION: Synthetic antibody sequence.

<400> SEQUENCE: 38

Gln Ser Ala Leu Thr Gln Pro Pro Ser Val Ser Val Ser Pro Gly Gln
1               5               10              15

Thr Ala Ser Ile Thr Cys Ser Gly Asp Lys Leu Gly Glu Lys Tyr Ala
            20              25              30

Ser Trp Tyr Gln Gln Lys Ala Gly Gln Ser Pro Val Met Val Ile Tyr
        35              40              45

Gln Asp Arg Lys Arg Pro Ser Gly Ile Pro Glu Arg Phe Ser Gly Ser
    50              55              60

Asn Ser Gly Asn Thr Ala Thr Leu Thr Ile Ser Gly Thr Gln Ala Met
65              70              75              80

Asp Glu Ala Asp Tyr Tyr Cys Gln Ala Trp Asp Thr Arg Ala Val Val
            85              90              95

Phe Gly Gly Gly Thr Lys Leu Thr Val Leu Gly Gln Pro Lys Ala Ala
            100             105             110

Pro Ser Val Thr Leu Phe Pro Pro Ser Ser Glu Glu Leu Gln Ala Asn
        115             120             125

Lys Ala Thr Leu Val Cys Leu Ile Ser Asp Phe Tyr Pro Gly Ala Val
    130             135             140

Thr Val Ala Trp Lys Ala Asp Gly Ser Pro Val Lys Ala Gly Val Glu
145             150             155             160

Thr Thr Ile Pro Ser Lys Gln Ser Asn Asn Lys Tyr Ala Ala Ser Ser
            165             170             175

Tyr Leu Ser Leu Thr Pro Glu Gln Trp Lys Ser His Arg Ser Tyr Ser
            180             185             190

Cys Gln Val Thr His Glu Gly Ser Thr Val Glu Lys Thr Val Ala Pro
        195             200             205

Thr Glu Cys Ser
    210

<210> SEQ ID NO 39
<211> LENGTH: 214
<212> TYPE: PRT
<213> ORGANISM: Artificial Sequence
<220> FEATURE:
<223> OTHER INFORMATION: Synthetic antibody sequence.

<400> SEQUENCE: 39

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
                20                  25                  30

Tyr Trp Tyr His Gln Lys Ser Gly Gln Ala Pro Val Leu Val Ile Tyr
            35                  40                  45

Glu Asp Arg Arg Arg Pro Ser Glu Ile Pro Glu Arg Phe Ser Gly Ser
    50                  55                  60

Ser Ser Gly Thr Met Ala Thr Leu Thr Ile Thr Gly Ala Gln Val Glu
65                  70                  75                  80

Asp Glu Gly Val Tyr Phe Cys Tyr Ser Arg Asp Arg Ala Gly Asn Gln
                85                  90                  95

Arg Val Phe Gly Gly Gly Thr Gln Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
    210

<210> SEQ ID NO 40
<211> LENGTH: 5
<212> TYPE: PRT
<213> ORGANISM: Artificial Sequence
<220> FEATURE:
<223> OTHER INFORMATION: Synthetic antibody sequence.
<220> FEATURE:
<221> NAME/KEY: X1
<222> LOCATION: (1)..(1)
<223> OTHER INFORMATION: Xaa is Ser or Trp
<220> FEATURE:
<221> NAME/KEY: X3
<222> LOCATION: (3)..(3)
<223> OTHER INFORMATION: Xaa is Trp or Gln
<220> FEATURE:
<221> NAME/KEY: X4
<222> LOCATION: (4)..(4)
<223> OTHER INFORMATION: Xaa is Ile or Met
<220> FEATURE:
<221> NAME/KEY: X5
<222> LOCATION: (5)..(5)
<223> OTHER INFORMATION: Xaa is Gly or Met

<400> SEQUENCE: 40

Xaa Tyr Xaa Xaa Xaa
1               5

<210> SEQ ID NO 41
<211> LENGTH: 17
<212> TYPE: PRT
<213> ORGANISM: Artificial Sequence
<220> FEATURE:

```
<223> OTHER INFORMATION: Synthetic antibody sequence.
<220> FEATURE:
<221> NAME/KEY: X1
<222> LOCATION: (1)..(1)
<223> OTHER INFORMATION: Xaa is Ile or Arg.
<220> FEATURE:
<221> NAME/KEY: X5
<222> LOCATION: (5)..(5)
<223> OTHER INFORMATION: Xaa is Gly or Ser.
<220> FEATURE:
<221> NAME/KEY: X6
<222> LOCATION: (6)..(6)
<223> OTHER INFORMATION: Xaa is Asp or Gly.
<220> FEATURE:
<221> NAME/KEY: X7
<222> LOCATION: (7)..(7)
<223> OTHER INFORMATION: Xaa is Ser or Gly.
<220> FEATURE:
<221> NAME/KEY: X8
<222> LOCATION: (8)..(8)
<223> OTHER INFORMATION: Xaa is Asp or Gly.
<220> FEATURE:
<221> NAME/KEY: X10
<222> LOCATION: (10)..(10)
<223> OTHER INFORMATION: Xaa is Arg or Ala.
<220> FEATURE:
<221> NAME/KEY: X12
<222> LOCATION: (12)..(12)
<223> OTHER INFORMATION: Xaa is Ser or Ala.
<220> FEATURE:
<221> NAME/KEY: X13
<222> LOCATION: (13)..(13)
<223> OTHER INFORMATION: Xaa is Pro or Asp.
<220> FEATURE:
<221> NAME/KEY: X15
<222> LOCATION: (15)..(15)
<223> OTHER INFORMATION: Xaa is Phe or Val.
<220> FEATURE:
<221> NAME/KEY: X16
<222> LOCATION: (16)..(16)
<223> OTHER INFORMATION: Xaa is Gln or Lys.

<400> SEQUENCE: 41

Xaa Ile Tyr Pro Xaa Xaa Xaa Xaa Thr Xaa Tyr Xaa Xaa Ser Xaa Xaa
1               5                   10                  15

Gly

<210> SEQ ID NO 42
<211> LENGTH: 10
<212> TYPE: PRT
<213> ORGANISM: Artificial Sequence
<220> FEATURE:
<223> OTHER INFORMATION: Synthetic antibody sequence.
<220> FEATURE:
<221> NAME/KEY: X1
<222> LOCATION: (1)..(1)
<223> OTHER INFORMATION: Xaa is Arg or Asp.
<220> FEATURE:
<221> NAME/KEY: X2
<222> LOCATION: (2)..(2)
<223> OTHER INFORMATION: Xaa is Phe or Gly or Ala.
<220> FEATURE:
<221> NAME/KEY: X3
<222> LOCATION: (3)..(3)
<223> OTHER INFORMATION: Xaa is Ser or His or Gly.
<220> FEATURE:
<221> NAME/KEY: X5
<222> LOCATION: (5)..(5)
<223> OTHER INFORMATION: Xaa is Ser or Gly.
<220> FEATURE:
<221> NAME/KEY: X6
<222> LOCATION: (6)..(6)
<223> OTHER INFORMATION: Xaa is Ser or Asp.
<220> FEATURE:
<221> NAME/KEY: X7
<222> LOCATION: (7)..(7)
```

```
<223> OTHER INFORMATION: Xaa is Gly or Tyr or is absent.
<220> FEATURE:
<221> NAME/KEY: X8
<222> LOCATION: (8)..(8)
<223> OTHER INFORMATION: Xaa is Trp or Phe or is absent.
<220> FEATURE:
<221> NAME/KEY: X9
<222> LOCATION: (9)..(9)
<223> OTHER INFORMATION: Xaa is Asp or is absent.
<220> FEATURE:
<221> NAME/KEY: X10
<222> LOCATION: (10)..(10)
<223> OTHER INFORMATION: Xaa is Met or Tyr or Asn.

<400> SEQUENCE: 42

Xaa Xaa Xaa Tyr Xaa Xaa Xaa Xaa Xaa Xaa
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic antibody sequence.
<220> FEATURE:
<221> NAME/KEY: X4
<222> LOCATION: (4)..(4)
<223> OTHER INFORMATION: Xaa is Ala or Lys.
<220> FEATURE:
<221> NAME/KEY: X6
<222> LOCATION: (6)..(6)
<223> OTHER INFORMATION: Xaa is Thr or Pro or Gly.
<220> FEATURE:
<221> NAME/KEY: X7
<222> LOCATION: (7)..(7)
<223> OTHER INFORMATION: Xaa is Ser or Lys or Glu.
<220> FEATURE:
<221> NAME/KEY: X10
<222> LOCATION: (10)..(10)
<223> OTHER INFORMATION: Xaa is Val or Ala.
<220> FEATURE:
<221> NAME/KEY: X11
<222> LOCATION: (11)..(11)
<223> OTHER INFORMATION: Xaa is Ala or Tyr or Ser.

<400> SEQUENCE: 43

Ser Gly Asp Xaa Leu Xaa Xaa Lys Tyr Xaa Xaa
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Synthetic antibody sequence.
<220> FEATURE:
<221> NAME/KEY: X1
<222> LOCATION: (1)..(1)
<223> OTHER INFORMATION: Xaa is Glu or Gln.
<220> FEATURE:
<221> NAME/KEY: X3
<222> LOCATION: (3)..(3)
<223> OTHER INFORMATION: Xaa is Thr or Arg.
<220> FEATURE:
<221> NAME/KEY: X4
<222> LOCATION: (4)..(4)
<223> OTHER INFORMATION: Xaa is Arg or Lys.

<400> SEQUENCE: 44

Xaa Asp Xaa Xaa Arg Pro Ser
1               5

<210> SEQ ID NO 45
```

```
<211> LENGTH: 11
<212> TYPE: PRT
<213> ORGANISM: Artificial Sequence
<220> FEATURE:
<223> OTHER INFORMATION: Synthetic antibody sequence.
<220> FEATURE:
<221> NAME/KEY: X1
<222> LOCATION: (1)..(1)
<223> OTHER INFORMATION: Xaa is Tyr or Gln.
<220> FEATURE:
<221> NAME/KEY: X2
<222> LOCATION: (2)..(2)
<223> OTHER INFORMATION: Xaa is Ser or Ala.
<220> FEATURE:
<221> NAME/KEY: X3
<222> LOCATION: (3)..(3)
<223> OTHER INFORMATION: Xaa is Thr or Arg or Trp.
<220> FEATURE:
<221> NAME/KEY: X5
<222> LOCATION: (5)..(5)
<223> OTHER INFORMATION: Xaa is Ala or Arg or Thr.
<220> FEATURE:
<221> NAME/KEY: X6
<222> LOCATION: (6)..(6)
<223> OTHER INFORMATION: Xaa is Ser or Ala or is absent.
<220> FEATURE:
<221> NAME/KEY: X7
<222> LOCATION: (7)..(7)
<223> OTHER INFORMATION: Xaa is Gly or is absent.
<220> FEATURE:
<221> NAME/KEY: X8
<222> LOCATION: (8)..(8)
<223> OTHER INFORMATION: Xaa is His or Asn or Arg.
<220> FEATURE:
<221> NAME/KEY: X9
<222> LOCATION: (9)..(9)
<223> OTHER INFORMATION: Xaa is Gln or Ala.
<220> FEATURE:
<221> NAME/KEY: X10
<222> LOCATION: (10)..(10)
<223> OTHER INFORMATION: Xaa is Arg or Val.

<400> SEQUENCE: 45

Xaa Xaa Xaa Asp Xaa Xaa Xaa Xaa Xaa Xaa Val
1               5                   10

<210> SEQ ID NO 46
<211> LENGTH: 124
<212> TYPE: PRT
<213> ORGANISM: Artificial Sequence
<220> FEATURE:
<223> OTHER INFORMATION: Synthetic antibody sequence.

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Trp Met Gly Trp Val Arg Gln Ala Thr Gly Lys Gly Leu Glu Trp Val
        35                  40                  45

Ser Ser Ile Tyr Ser Ser Gly Gly Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Pro Arg Ser Phe Ser Gly Ser Tyr Tyr Arg Ala Phe Asp
            100                 105                 110

Ile Trp Gly Gln Gly Thr Met Val Thr Val Ser Ser
```

-continued

```
             115                 120

<210> SEQ ID NO 47
<211> LENGTH: 119
<212> TYPE: PRT
<213> ORGANISM: Artificial Sequence
<220> FEATURE:
<223> OTHER INFORMATION: Synthetic antibody sequence.

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Tyr Met Met Trp Val Arg Gln Ala Pro Gly Lys Gly Leu Glu Trp Val
        35                  40                  45

Ser Ser Ile Gly Ser Ser Gly Gly Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Lys Gly Gly Met Val Leu Gly Val Val Asn Ile Trp Gly Gln Gly
            100                 105                 110

Thr Leu Val Thr Val Ser Ser
        115

<210> SEQ ID NO 48
<211> LENGTH: 124
<212> TYPE: PRT
<213> ORGANISM: Artificial Sequence
<220> FEATURE:
<223> OTHER INFORMATION: Synthetic antibody sequence.

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Trp Met Gly Trp Val Arg Gln Ala Pro Gly Lys Gly Leu Glu Trp Val
        35                  40                  45

Ser Ser Ile Tyr Ser Ser Gly Gly Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Pro Arg Ser Phe Ser Gly Ser Tyr Tyr Arg Ala Phe Asp
            100                 105                 110

Ile Trp Gly Gln Gly Thr Met Val Thr Val Ser Ser
        115                 120

<210> SEQ ID NO 49
<211> LENGTH: 119
<212> TYPE: PRT
<213> ORGANISM: Artificial Sequence
<220> FEATURE:
<223> OTHER INFORMATION: Synthetic antibody sequence.

<400> SEQUENCE: 49
```

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Tyr Met Met Trp Val Arg Gln Ala Pro Gly Lys Gly Leu Glu Trp Val
        35                  40                  45

Ser Ser Ile Gly Ser Ser Gly Gly Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Met Val Leu Gly Val Val Asn Ile Trp Gly Gln Gly
            100                 105                 110

Thr Leu Val Thr Val Ser Ser
        115
```

```
<210> SEQ ID NO 50
<211> LENGTH: 109
<212> TYPE: PRT
<213> ORGANISM: Artificial Sequence
<220> FEATURE:
<223> OTHER INFORMATION: Synthetic antibody sequence.

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Asp Tyr
            20                  25                  30

Leu Asn Trp Tyr Gln Gln Arg Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Ser Tyr Ser Ser Ser Ile
                85                  90                  95

Thr Phe Gly Gln Gly Thr Arg Leu Asp Leu Lys Arg Thr
            100                 105
```

```
<210> SEQ ID NO 51
<211> LENGTH: 110
<212> TYPE: PRT
<213> ORGANISM: Artificial Sequence
<220> FEATURE:
<223> OTHER INFORMATION: Synthetic antibody sequence.

<400> SEQUENCE: 51

Gln Ser Ala Leu Thr Gln Pro Pro Ser Val Ser Val Ser Pro Gly Gln
1               5                   10                  15

Thr Ala Thr Ile Thr Cys Ser Gly Asp Lys Leu Gly Glu Lys Tyr Val
            20                  25                  30

Ser Trp Tyr Gln Gln Lys Pro Gly Gln Ser Pro Val Val Val Ile Phe
        35                  40                  45

Gln Asp Ile Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
```

```
65              70              75              80

Asp Glu Ala Asp Tyr Tyr Cys Gln Thr Trp Gly Thr Gly Gly Ile Gln
            85              90              95

Val Phe Gly Gly Gly Thr Lys Leu Thr Val Leu Arg Gln Pro
            100             105             110

<210> SEQ ID NO 52
<211> LENGTH: 109
<212> TYPE: PRT
<213> ORGANISM: Artificial Sequence
<220> FEATURE:
<223> OTHER INFORMATION: Synthetic antibody sequence.

<400> SEQUENCE: 52

Asp Ile Gln Met Thr Gln Ser Pro Ser Ser Leu Ser Ala Ser Val Gly
1               5               10              15

Asp Arg Val Thr Ile Thr Cys Arg Ala Ser Gln Ser Ile Thr Asp Tyr
            20              25              30

Leu Asn Trp Tyr Gln Gln Lys Pro Gly Lys Ala Pro Lys Leu Leu Ile
        35              40              45

Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Ser Ser Ser Ile
            85              90              95

Thr Phe Gly Gln Gly Thr Arg Leu Asp Leu Lys Arg Thr
            100             105

<210> SEQ ID NO 53
<211> LENGTH: 110
<212> TYPE: PRT
<213> ORGANISM: Artificial Sequence
<220> FEATURE:
<223> OTHER INFORMATION: Synthetic antibody sequence.

<400> SEQUENCE: 53

Ser Tyr Glu Leu Thr Gln Pro Pro Ser Val Ser Val Ser Pro Gly Gln
1               5               10              15

Thr Ala Ser Ile Thr Cys Ser Gly Asp Lys Leu Gly Glu Lys Tyr Val
            20              25              30

Ser Trp Tyr Gln Gln Lys Pro Gly Gln Ser Pro Val Leu Val Ile Tyr
        35              40              45

Gln Asp Ile Lys Arg Pro Ser Gly Ile Pro Glu Arg Phe Ser Gly Ser
    50              55              60

Asn Ser Gly Asn Thr Ala Thr Leu Thr Ile Ser Gly Thr Gln Ala Met
65              70              75              80

Asp Glu Ala Asp Tyr Tyr Cys Gln Thr Trp Gly Thr Gly Gly Ile Gln
            85              90              95

Val Phe Gly Gly Gly Thr Lys Leu Thr Val Leu Gly Gln Pro
            100             105             110

<210> SEQ ID NO 54
<211> LENGTH: 5
<212> TYPE: PRT
<213> ORGANISM: Artificial Sequence
<220> FEATURE:
<223> OTHER INFORMATION: Synthetic antibody sequence.

<400> SEQUENCE: 54
```

Lys Tyr Trp Met Gly
1               5

<210> SEQ ID NO 55
<211> LENGTH: 16
<212> TYPE: PRT
<213> ORGANISM: Artificial Sequence
<220> FEATURE:
<223> OTHER INFORMATION: Synthetic antibody sequence.

<400> SEQUENCE: 55

Ser Ile Tyr Ser Ser Gly Gly Trp Thr Tyr Tyr Ala Asp Ser Val Lys
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic antibody sequence.

<400> SEQUENCE: 56

Arg Pro Arg Ser Phe Ser Gly Ser Tyr Tyr Arg Ala Phe Asp Ile
1               5                   10                  15

<210> SEQ ID NO 57
<211> LENGTH: 11
<212> TYPE: PRT
<213> ORGANISM: Artificial Sequence
<220> FEATURE:
<223> OTHER INFORMATION: Synthetic antibody sequence.

<400> SEQUENCE: 57

Arg Ala Ser Gln Ser Ile Thr Asp Tyr Leu Asn
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Synthetic antibody sequence.

<400> SEQUENCE: 58

Ala Ala Ser Ser Leu Gln Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic antibody sequence.

<400> SEQUENCE: 59

Gln Gln Ser Tyr Ser Ser Ser Ile Thr
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic antibody sequence.

<400> SEQUENCE: 60

```
Arg Tyr Tyr Met Met
1               5

<210> SEQ ID NO 61
<211> LENGTH: 17
<212> TYPE: PRT
<213> ORGANISM: Artificial Sequence
<220> FEATURE:
<223> OTHER INFORMATION: Synthetic antibody sequence.

<400> SEQUENCE: 61

Ser Ile Gly Ser Ser Gly Gly Thr Thr Asn Tyr Ala Asp Ser Val Lys
1               5                   10                  15

Gly

<210> SEQ ID NO 62
<211> LENGTH: 10
<212> TYPE: PRT
<213> ORGANISM: Artificial Sequence
<220> FEATURE:
<223> OTHER INFORMATION: Synthetic antibody sequence.

<400> SEQUENCE: 62

Gly Gly Met Val Leu Gly Val Val Asn Ile
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic antibody sequence.

<400> SEQUENCE: 63

Ser Gly Asp Lys Leu Gly Glu Lys Tyr Val Ser
1               5                   10

<210> SEQ ID NO 64
<211> LENGTH: 7
<212> TYPE: PRT
<213> ORGANISM: Artificial Sequence
<220> FEATURE:
<223> OTHER INFORMATION: Synthetic antibody sequence.

<400> SEQUENCE: 64

Gln Asp Ile Lys Arg Pro Ser
1               5

<210> SEQ ID NO 65
<211> LENGTH: 10
<212> TYPE: PRT
<213> ORGANISM: Artificial Sequence
<220> FEATURE:
<223> OTHER INFORMATION: Synthetic antibody sequence.

<400> SEQUENCE: 65

Gln Thr Trp Gly Thr Gly Gly Ile Gln Val
1               5                   10

<210> SEQ ID NO 66
<211> LENGTH: 5
<212> TYPE: PRT
<213> ORGANISM: Artificial Sequence
<220> FEATURE:
<223> OTHER INFORMATION: Synthetic antibody sequence.
<220> FEATURE:
<221> NAME/KEY: X1
```

```
<222> LOCATION: (1)..(1)
<223> OTHER INFORMATION: Xaa is Ser or Arg or Lys or Trp.
<220> FEATURE:
<221> NAME/KEY: X3
<222> LOCATION: (3)..(3)
<223> OTHER INFORMATION: Xaa is Trp or Tyr or Gln.
<220> FEATURE:
<221> NAME/KEY: X4
<222> LOCATION: (4)..(4)
<223> OTHER INFORMATION: Xaa is Ile or Met.
<220> FEATURE:
<221> NAME/KEY: X5
<222> LOCATION: (5)..(5)
<223> OTHER INFORMATION: Xaa is Gly or Met.

<400> SEQUENCE: 66

Xaa Tyr Xaa Xaa Xaa
1               5

<210> SEQ ID NO 67
<211> LENGTH: 17
<212> TYPE: PRT
<213> ORGANISM: Artificial Sequence
<220> FEATURE:
<223> OTHER INFORMATION: Synthetic antibody sequence.
<220> FEATURE:
<221> NAME/KEY: X1
<222> LOCATION: (1)..(1)
<223> OTHER INFORMATION: Xaa is Ile or Ser or Arg.
<220> FEATURE:
<221> NAME/KEY: X3
<222> LOCATION: (3)..(3)
<223> OTHER INFORMATION: Xaa is Tyr or Gly.
<220> FEATURE:
<221> NAME/KEY: X4
<222> LOCATION: (4)..(4)
<223> OTHER INFORMATION: Xaa is Pro or Ser.
<220> FEATURE:
<221> NAME/KEY: X5
<222> LOCATION: (5)..(5)
<223> OTHER INFORMATION: Xaa is Gly or Ser.
<220> FEATURE:
<221> NAME/KEY: X6
<222> LOCATION: (6)..(6)
<223> OTHER INFORMATION: Xaa is Asp or Gly.
<220> FEATURE:
<221> NAME/KEY: X7
<222> LOCATION: (7)..(7)
<223> OTHER INFORMATION: Xaa is Ser or Gly.
<220> FEATURE:
<221> NAME/KEY: X8
<222> LOCATION: (8)..(8)
<223> OTHER INFORMATION: Xaa is Asp or Thr or Trp or Gly.
<220> FEATURE:
<221> NAME/KEY: X10
<222> LOCATION: (10)..(10)
<223> OTHER INFORMATION: Xaa is Arg or Asn or Tyr or Ala.
<220> FEATURE:
<221> NAME/KEY: X12
<222> LOCATION: (12)..(12)
<223> OTHER INFORMATION: Xaa is Ser or Ala.
<220> FEATURE:
<221> NAME/KEY: X13
<222> LOCATION: (13)..(13)
<223> OTHER INFORMATION: Xaa is Pro or Asp.
<220> FEATURE:
<221> NAME/KEY: X15
<222> LOCATION: (15)..(15)
<223> OTHER INFORMATION: Xaa is Phe or Val.
<220> FEATURE:
<221> NAME/KEY: X16
<222> LOCATION: (16)..(16)
<223> OTHER INFORMATION: Xaa is Gln or Lys.

<400> SEQUENCE: 67

Xaa Ile Xaa Xaa Xaa Xaa Xaa Xaa Thr Xaa Tyr Xaa Xaa Ser Xaa Xaa
```

-continued

```
1               5               10              15

Gly

<210> SEQ ID NO 68
<211> LENGTH: 15
<212> TYPE: PRT
<213> ORGANISM: Artificial Sequence
<220> FEATURE:
<223> OTHER INFORMATION: Synthetic antibody sequence.
<220> FEATURE:
<221> NAME/KEY: X1
<222> LOCATION: (1)..(1)
<223> OTHER INFORMATION: Xaa is Arg or Gly or Asp.
<220> FEATURE:
<221> NAME/KEY: X2
<222> LOCATION: (2)..(2)
<223> OTHER INFORMATION: Xaa is Phe or Gly or Pro or Ala.
<220> FEATURE:
<221> NAME/KEY: X3
<222> LOCATION: (3)..(3)
<223> OTHER INFORMATION: Xaa is Ser or His or Met or Arg or Gly.
<220> FEATURE:
<221> NAME/KEY: X4
<222> LOCATION: (4)..(4)
<223> OTHER INFORMATION: Xaa is Ser or is absent.
<220> FEATURE:
<221> NAME/KEY: X5
<222> LOCATION: (5)..(5)
<223> OTHER INFORMATION: Xaa is Phe or is absent.
<220> FEATURE:
<221> NAME/KEY: X6
<222> LOCATION: (6)..(6)
<223> OTHER INFORMATION: Xaa is Ser or is absent.
<220> FEATURE:
<221> NAME/KEY: X7
<222> LOCATION: (7)..(7)
<223> OTHER INFORMATION: Xaa is Gly or is absent.
<220> FEATURE:
<221> NAME/KEY: X8
<222> LOCATION: (8)..(8)
<223> OTHER INFORMATION: Xaa is Ser or is absent.
<220> FEATURE:
<221> NAME/KEY: X9
<222> LOCATION: (9)..(9)
<223> OTHER INFORMATION: Xaa is Tyr or Val or is absent.
<220> FEATURE:
<221> NAME/KEY: X10
<222> LOCATION: (10)..(10)
<223> OTHER INFORMATION: Xaa is Ser or Gly or Leu or Tyr or is absent.
<220> FEATURE:
<221> NAME/KEY: X11
<222> LOCATION: (11)..(11)
<223> OTHER INFORMATION: Xaa is Ser or Asp or Gly or Arg or is absent.
<220> FEATURE:
<221> NAME/KEY: X12
<222> LOCATION: (12)..(12)
<223> OTHER INFORMATION: Xaa is Gly or Tyr or Val or Ala.
<220> FEATURE:
<221> NAME/KEY: X13
<222> LOCATION: (13)..(13)
<223> OTHER INFORMATION: Xaa is Trp or Phe or Val or Gly.
<220> FEATURE:
<221> NAME/KEY: X14
<222> LOCATION: (14)..(14)
<223> OTHER INFORMATION: Xaa is Asp or Asn.
<220> FEATURE:
<221> NAME/KEY: X15
<222> LOCATION: (15)..(15)
<223> OTHER INFORMATION: Xaa is Met or Tyr or Ile or Asn.

<400> SEQUENCE: 68

Xaa Xaa Xaa Xaa Xaa Xaa Xaa Xaa Xaa Xaa Xaa Xaa Xaa Xaa Xaa
1               5               10              15

<210> SEQ ID NO 69
```

```
<211> LENGTH: 11
<212> TYPE: PRT
<213> ORGANISM: Artificial Sequence
<220> FEATURE:
<223> OTHER INFORMATION: Synthetic antibody sequence.
<220> FEATURE:
<221> NAME/KEY: X1
<222> LOCATION: (1)..(1)
<223> OTHER INFORMATION: Xaa is Arg or Ser.
<220> FEATURE:
<221> NAME/KEY: X2
<222> LOCATION: (2)..(2)
<223> OTHER INFORMATION: Xaa is Ala or Gly.
<220> FEATURE:
<221> NAME/KEY: X3
<222> LOCATION: (3)..(3)
<223> OTHER INFORMATION: Xaa is Ser or Asp.
<220> FEATURE:
<221> NAME/KEY: X4
<222> LOCATION: (4)..(4)
<223> OTHER INFORMATION: Xaa is Gln or Lys or Ala.
<220> FEATURE:
<221> NAME/KEY: X5
<222> LOCATION: (5)..(5)
<223> OTHER INFORMATION: Xaa is Ser or Leu.
<220> FEATURE:
<221> NAME/KEY: X6
<222> LOCATION: (6)..(6)
<223> OTHER INFORMATION: Xaa is Ile or Gly or Thr or Pro.
<220> FEATURE:
<221> NAME/KEY: X7
<222> LOCATION: (7)..(7)
<223> OTHER INFORMATION: Xaa is Thr or Glu or Ser or Lys.
<220> FEATURE:
<221> NAME/KEY: X8
<222> LOCATION: (8)..(8)
<223> OTHER INFORMATION: Xaa is Asp or Lys.
<220> FEATURE:
<221> NAME/KEY: X10
<222> LOCATION: (10)..(10)
<223> OTHER INFORMATION: Xaa is Leu or Val or Ala.
<220> FEATURE:
<221> NAME/KEY: X11
<222> LOCATION: (11)..(11)
<223> OTHER INFORMATION: Xaa is Asn or Ser or Ala or Tyr.

<400> SEQUENCE: 69

Xaa Xaa Xaa Xaa Xaa Xaa Xaa Xaa Tyr Xaa Xaa
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Synthetic antibody sequence.
<220> FEATURE:
<221> NAME/KEY: X1
<222> LOCATION: (1)..(1)
<223> OTHER INFORMATION: Xaa is Ala or Gln or Glu.
<220> FEATURE:
<221> NAME/KEY: X2
<222> LOCATION: (2)..(2)
<223> OTHER INFORMATION: Xaa is Ala or Asp.
<220> FEATURE:
<221> NAME/KEY: X3
<222> LOCATION: (3)..(3)
<223> OTHER INFORMATION: Xaa is Ser or Ile or Arg or Thr.
<220> FEATURE:
<221> NAME/KEY: X4
<222> LOCATION: (4)..(4)
<223> OTHER INFORMATION: Xaa is Ser or Lys or Arg.
<220> FEATURE:
<221> NAME/KEY: X5
<222> LOCATION: (5)..(5)
<223> OTHER INFORMATION: Xaa is Leu or Arg.
<220> FEATURE:
```

```
<221> NAME/KEY: X6
<222> LOCATION: (6)..(6)
<223> OTHER INFORMATION: Xaa is Gln or Pro.

<400> SEQUENCE: 70

Xaa Xaa Xaa Xaa Xaa Xaa Ser
1               5

<210> SEQ ID NO 71
<211> LENGTH: 11
<212> TYPE: PRT
<213> ORGANISM: Artificial Sequence
<220> FEATURE:
<223> OTHER INFORMATION: Synthetic antibody sequence.
<220> FEATURE:
<221> NAME/KEY: X1
<222> LOCATION: (1)..(1)
<223> OTHER INFORMATION: Xaa is Gln or Tyr.
<220> FEATURE:
<221> NAME/KEY: X2
<222> LOCATION: (2)..(2)
<223> OTHER INFORMATION: Xaa is Gln or Thr or Ala or Ser.
<220> FEATURE:
<221> NAME/KEY: X3
<222> LOCATION: (3)..(3)
<223> OTHER INFORMATION: Xaa is Ser or Trp or Thr or Arg.
<220> FEATURE:
<221> NAME/KEY: X4
<222> LOCATION: (4)..(4)
<223> OTHER INFORMATION: Xaa is Tyr or Gly or Asp.
<220> FEATURE:
<221> NAME/KEY: X5
<222> LOCATION: (5)..(5)
<223> OTHER INFORMATION: Xaa is Ser or Thr or Ala or Arg.
<220> FEATURE:
<221> NAME/KEY: X6
<222> LOCATION: (6)..(6)
<223> OTHER INFORMATION: Xaa is Ser or Gly or Arg or Ala.
<220> FEATURE:
<221> NAME/KEY: X7
<222> LOCATION: (7)..(7)
<223> OTHER INFORMATION: Xaa is Gly or is absent.
<220> FEATURE:
<221> NAME/KEY: X8
<222> LOCATION: (8)..(8)
<223> OTHER INFORMATION: Xaa is Gly or Ala or His or Asn or is absent.
<220> FEATURE:
<221> NAME/KEY: X9
<222> LOCATION: (9)..(9)
<223> OTHER INFORMATION: Xaa is Ser or Ile or Gln or is absent.
<220> FEATURE:
<221> NAME/KEY: X10
<222> LOCATION: (10)..(10)
<223> OTHER INFORMATION: Xaa is Ile or Gln or Val or Arg.
<220> FEATURE:
<221> NAME/KEY: X11
<222> LOCATION: (11)..(11)
<223> OTHER INFORMATION: Xaa is Thr or Val.

<400> SEQUENCE: 71

Xaa Xaa Xaa Xaa Xaa Xaa Xaa Xaa Xaa Xaa Xaa
1               5                   10
```